US012419950B2

(12) United States Patent
Wang

(10) Patent No.: US 12,419,950 B2
(45) Date of Patent: *Sep. 23, 2025

(54) SAPONIN-BASED VACCINE ADJUVANTS

(71) Applicant: THE UAB RESEARCH FOUNDATION, Birmingham, AL (US)

(72) Inventor: Pengfei Wang, Hoover, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 918 days.

This patent is subject to a terminal disclaimer.

(21) Appl. No.: 17/440,009

(22) PCT Filed: Mar. 17, 2020

(86) PCT No.: PCT/US2020/023185
§ 371 (c)(1),
(2) Date: Sep. 16, 2021

(87) PCT Pub. No.: WO2020/190959
PCT Pub. Date: Sep. 24, 2020

(65) Prior Publication Data
US 2022/0152196 A1 May 19, 2022

Related U.S. Application Data

(60) Provisional application No. 62/820,477, filed on Mar. 19, 2019.

(51) Int. Cl.
A61K 39/39 (2006.01)
A61K 39/00 (2006.01)
A61K 45/06 (2006.01)
A61K 47/26 (2006.01)

(52) U.S. Cl.
CPC .............. *A61K 39/39* (2013.01); *A61K 45/06* (2013.01); *A61K 47/26* (2013.01); *A61K 2039/55577* (2013.01)

(58) Field of Classification Search
None
See application file for complete search history.

(56) References Cited

U.S. PATENT DOCUMENTS 6,080,725 A * 6/2000 Marciani .............. A61K 47/542
514/25

FOREIGN PATENT DOCUMENTS

WO 2013/142142 A1 9/2013
WO 2019/183159 A1 9/2019

OTHER PUBLICATIONS

Higuchi, Ryuichi, et al. "Structure of desacylsaponins obtained from the bark of Quillaja saponaria." Phytochemistry 26.1 (1987): 229-235. (Year: 1987).*
Wang, Pengfei, et al. "Synthesis and evaluation of QS-21-based immunoadjuvants with a terminal-functionalized side chain incorporated in the west wing trisaccharide." The Journal of organic chemistry 81.20 (2016): 9560-9566 and S1-S18. (Year: 2016).*
Brunner, Richard et al. "The ABC of clinical and experimental adjuvants—a brief overview." Immunology letters vol. 128, 1 (2010): 29-35. doi:10.1016/j.imlet.2009.10.005.
Kensil, Charlotte Read et al. "Current vaccine adjuvants: an overview of a diverse class." Frontiers in bioscience : a journal and virtual library vol. 9 2972-88. Sep. 1, 2004, doi:10.2741/1452.
Leroux-Roels, Geert. "Unmet needs in modern vaccinology: adjuvants to improve the immune response." Vaccine vol. 28 Suppl 3 (2010): C25-36. doi: 10.1016/j.vaccine.2010.07.021.
Sharp, Fiona A. et al., "Discovery of Vaccine Adjuvants", Development of Therapeutic Agents Handbook, First Edition, Edited by Shayne Cox Gad. © 2012 John Wiley & Sons, Inc. Published 2012 by John Wiley & Sons, Inc., pp. 533-546.
Wang W. et al., "Selection of Adjuvants for Enhanced Vaccine Potency", World Journal of Vaccines, 2011, 1, 33-78.
Weeratna Risni D. et al, "Recent Advances in Vaccine Adjuvants", pp. 303-322.
Cox, J C, et al., "Adjuvants—a classification and review of their modes of action." Vaccine vol. 15,3 (1997): 248-56. doi:10.1016/s0264-410x(96)00183-1.
Klebanoff, Christopher A et al. "Therapeutic cancer vaccines: are we there yet?." Immunological reviews vol. 239,1 (2011): 27-44. doi:10.1111/j.1600-065X.2010.00979.x.
Plotkin SA., Vaccines: past, present and future:. Nat Med. Apr. 2005;11(4 Suppl):S5-11. doi: 10.1038/nm1209. PMID: 15812490; PMCID: PMC7095920.
Rappuoli R, Aderem A., "A 2020 vision for vaccines against HIV, tuberculosis and malaria"., Nature. May 26, 2011;473 (7348):463-9. doi: 10.1038/nature10124. PMID: 21614073.
Kensil et al., "Effects of QS-21 on Innate and Adaptive Immune Responses", Vaccine Adjuvants: Immunological and Clinical Principles, 2005, pp. 221-234.
Ragupathi, Govind et al. "Natural and synthetic saponin adjuvant QS-21 for vaccines against cancer." Expert review of vaccines vol. 10,4 (2011): 463-70. doi:10.1586/erv.11.18.
Deng, Kai et al. "Synthesis of QS-21-xylose: establishment of the immunopotentiating activity of synthetic QS-21 adjuvant with a melanoma vaccine." Angewandte Chemie (International ed. in English) vol. 47,34 (2008): 6395-8. doi:10.1002/anie.200801885.

(Continued)

Primary Examiner — Bethany P Barham
Assistant Examiner — Peter Anthopolos
(74) Attorney, Agent, or Firm — THOMAS | HORSTEMEYER, LLP

(57) ABSTRACT

A number of MS- and natural-saponin-based vaccine adjuvant candidates have been prepared. The MS derivatives were prepared by incorporating a terminal-functionalized side chain into the C3 glucuronic acid unit of the natural saponins MS I and II through amide formation reaction; and the QS analogs were prepared via multi-step organic synthesis. These unnatural saponins showed significantly different immunostimulant activity profiles, suggesting that the structure of side chain, triterpenoid core, and oligosaccharide domain together orchestrate each saponin's characteristic potentiation of immune responses.

26 Claims, 24 Drawing Sheets

(56) References Cited

OTHER PUBLICATIONS

Kensil, C R. "Saponins as vaccine adjuvants." Critical reviews in therapeutic drug carrier systems vol. 13,1-2 (1996): 1-55.
Kensil, C R et al. "Separation and characterization of saponins with adjuvant activity from Quillaja saponaria Molina cortex." Journal of immunology (Baltimore, Md. : 1950) vol. 146,2 (1991): 431-7.
Ragupathi, Govind et al. "Preclinical evaluation of the synthetic adjuvant SQS-21 and its constituent isomeric saponins." Vaccine vol. 28,26 (2010): 4260-7. doi: 10.1016/j.vaccine.2010.04.034.
Wang, Pengfei et al. "Synthesis of the potent immunostimulatory adjuvant QS-21A." Journal of the American Chemical Society vol. 127,10 (2005): 3256-7. doi:10.1021/ja0422007.
Adams, Michelle M et al. "Design and synthesis of potent Quillaja saponin vaccine adjuvants." Journal of the American Chemical Society vol. 132,6 (2010): 1939-45. doi:10.1021/ja9082842.
Chea, Eric K et al. "Synthesis and preclinical evaluation of QS-21 variants leading to simplified vaccine adjuvants and mechanistic probes." Journal of the American Chemical Society vol. 134,32 (2012): 13448-57. doi: 10.1021/ja305121q.
Fernández-Tejada, Alberto et al. "Development of a minimal saponin vaccine adjuvant based on QS-21." Nature chemistry vol. 6,7 (2014): 635-43. doi: 10.1038/nchem.1963.
Wang, Pengfei, et al. "Synthesis of QS-21-Based Immunoadjuvants", 2013 American Chemical Society, J. Org. Chem. 2013, 78, 11525-11534.
Slovin, Susan F et al. "A bivalent conjugate vaccine in the treatment of biochemically relapsed prostate cancer: a study of glycosylated MUC-2-KLH and Globo H-KLH conjugate vaccines given with the new semi-synthetic saponin immunological adjuvant GPI-0100 or QS-21." Vaccine vol. 23,24 (2005): 3114-22. doi:10.1016/j.vaccine. 2005.01.072.
Lieberman MM, et al., "Immunogenicity and protective efficacy of a recombinant subunit West Nile virus vaccine in rhesus monkeys"., Clin Vaccine Immunol. Sep. 2009;16(9):1332-7. doi: 10.1128/CVI. 00119-09. Epub Jul. 29, 2009. PMID: 19641099; PMCID: PMC2745014.
Liu, Heng et al. "Preclinical evaluation of the saponin derivative GPI-0100 as an immunostimulating and dose-sparing adjuvant for pandemic influenza vaccines." Vaccine vol. 29,11 (2011): 2037-43. doi: 10.1016/j.vaccine.2011.01.012.
Quenelle, Debra C et al. "Effect of immunization with herpes simplex virus type-1 (HSV-1) glycoprotein D (gD) plus the immune enhancer GPI-0100 on infection with HSV-1 or HSV-2." Vaccine vol. 24, 10 (2006): 1515-22. doi: 10.1016/j.vaccine.2005.10.017.
Zhang, Ping et al. "Effectiveness of the quillaja saponin semi-synthetic analog GPI-0100 in potentiating mucosal and systemic responses to recombinant HagB from Porphyromonas gingivalis." Vaccine vol. 21,27-30 (2003): 4459-71. doi:10.1016/s0264-410x(03)00438-9.
Marciani, Dante J et al. "Fractionation, structural studies, and immunological characterization of the semi-synthetic Quillaja saponins derivative GPI-0100." Vaccine vol. 21,25-26 (2003): 3961-71. doi: 10.1016/s0264-410x(03)00298-6.
Wang, Pengfei et al. "Simple glycosylation reaction of allyl glycosides." The Journal of organic chemistry vol. 72,15 (2007): 5870-5873. doi:10.1021/jo070512x.
Wang, Yun et al., "Concise synthesis of Bacillus anthracis exosporium tetrasaccharide via two-stage activation of allyl glycosyl donor strategy", Tetrahedron Letters 52 (2011) 3912-3915, Department of Chemistry, University of Alabama at Birmingham, Birmingham, AL 35294, USA.
Wang, Yun et al. "Facile glycosylation strategy with two-stage activation of allyl glycosyl donors. Application to concise synthesis of Shigella flexneri serotype Y O-antigen." Organic & biomolecular chemistry vol. 8, 19 (2010): 4322-8. doi:10.1039/c002865g.
Yang, Haishen, and Pengfei Wang. "Mechanistic study of glycosylation using a prop-1-enyl donor." The Journal of organic chemistry vol. 78,5 (2013): 1858-63. doi:10.1021/jo301664c.
Marciani, D J et al. "Development of semisynthetic triterpenoid saponin derivatives with immune stimulating activity." Vaccine vol. 18,27 (2000): 3141-3151. doi:10.1016/s0264-410x(00)00118-3.
Marciani, D J et al. "Altered immunomodulating and toxicological properties of degraded Quillaja saponaria Molina saponins." International immunopharmacology vol. 1,4 (2001): 813-8. doi:10.1016/s1567-5769(01)00016-9.
Marciani, Dante J et al. "Degradation of Quillaja saponaria Molina saponins: loss of the protective effects of a herpes simplex virus 1 subunit vaccine." International immunopharmacology vol. 2,12 (2002): 1703-11. doi: 10.1016/s1567-5769(02)00192-3.
Soltysik, S et al. "Structure/function studies of QS-21 adjuvant: assessment of triterpene aldehyde and glucuronic acid roles in adjuvant function." Vaccine vol. 13,15 (1995): 1403-10. doi: 10.1016/0264-410x(95)00077-e.
Liu, Gui et al. "QS-21 structure/function studies: effect of acylation on adjuvant activity." Vaccine vol. 20,21-22 (2002): 2808-15. doi:10.1016/s0264-410x(02)00209-8.
Marciani, Dante J et al. "Quillaja saponin adjuvants: derivatives formed under sub-optimal conditions." Vaccine vol. 20,27-28 (2002): 3237-8. doi:10.1016/s0264-410x(02)00298-0.
Gaddis, Dalia E et al. "Role of TLR2-dependent IL-10 production in the inhibition of the initial IFN-γ T cell response to Porphyromonas gingivalis." Journal of leukocyte biology vol. 93,1 (2013): 21-31. doi:10.1189/jlb.0512220.
Gaddis, Dalia E et al. "Requirement of TLR4 and CD14 in dendritic cell activation by Hemagglutinin B from Porphyromonas gingivalis." Molecular immunology vol. 46,13 (2009): 2493-504. doi:10.1016/j.molimm.2009.05.022.
Gaddis, Dalia E et al. "TLR4 signaling via MyD88 and TRIF differentially shape the CD4+ T cell response to Porphyromonas gingivalis hemagglutinin B." Journal of immunology (Baltimore, Md. : 1950) vol. 186,10 (2011): 5772-83. doi: 10.4049/jimmunol.1003192.
Katz, J et al. "Host responses to recombinant hemagglutinin B of Porphyromonas gingivalis in an experimental rat model." Infection and immunity vol. 67,9 (1999): 4352-9. doi:10.1128/IAI.67.9.4352-4359.1999.
Yang, Qiu-Bo et al. "Mechanisms of monophosphoryl lipid A augmentation of host responses to recombinant HagB from Porphyromonas gingivalis." Infection and immunity vol. 70,7 (2002): 3557-65. doi: 10.1128/IAI.70.7.3557-3565.2002.
Zhang, Ping et al. "Role of CD80 and CD86 in host immune responses to the recombinant hemagglutinin domain of Porphyromonas gingivalis gingipain and in the adjuvanticity of cholera toxin B and monophosphoryl lipid A." Vaccine vol. 25,33 (2007): 6201-10. doi:10.1016/j.vaccine.2007.05.066.
Zhang, Ping et al. "Role of mitogen-activated protein kinases and NF-kappaB in the regulation of proinflammatory and anti-inflammatory cytokines by Porphyromonas gingivalis hemagglutinin B." Infection and immunity vol. 73,7 (2005): 3990-8. doi:10.1128/IAI.73.7.3990-3998.2005.
Zhang, Ping et al. "Role of B7 costimulatory molecules in immune responses and T-helper cell differentiation in response to recombinant HagB from Porphyromonas gingivalis." Infection and immunity vol. 72,2 (2004): 637-44. doi:10.1128/IAI.72.2.637-644.2004.
Deng, Kai et al. "Synthesis and structure verification of the vaccine adjuvant QS-7-Api. Synthetic access to homogeneous Quillaja saponaria immunostimulants." Journal of the American Chemical Society vol. 130, 18 (2008): 5860-1. doi: 10.1021/ja801008m.
Higuchi R et al., "Structure of Desacylsaponins Obtained From the Bark of Quillaja Saponaria", Phytochemistry, vol. 26, No. I. pp. 229 235. 1987. Printed in Great Bntain.
Kite, Geoffrey C et al. "Metabolomic analysis of saponins in crude extracts of Quillaja saponaria by liquid chromatography/mass spectrometry for product authentication." Rapid communications in mass spectrometry : RCM vol. 18,23 (2004): 2859-70. doi:10.1002/rcm.1698.
Rhodes, J. "Covalent chemical events in immune induction: fundamental and therapeutic aspects." Immunology today vol. 17,9 (1996): 436-41. doi: 10.1016/0167-5699(96)10050-5.

(56) References Cited

OTHER PUBLICATIONS

Ashtekar, Amit R et al. "TLR4-mediated activation of dendritic cells by the heat shock protein DnaK from Francisella tularensis." Journal of leukocyte biology vol. 84,6 (2008): 1434-46. doi:10.1189/jlb.0308215.

European Search Report, EP Patent Application No. 20772529.2, mailed Nov. 23, 2022 (18 pages).

Wang, Pengfei, et al., "Synthesis and Evaluation of QS-21-Based Immunoadjuvants with a Terminal-Functionalized Side Chain Incorporated in the West Wing Trisaccharide," The Journal of Organic Chemistry, vol. 81 (2016), pp. 9560-9566.

Wang, Pengfei, et al., "Synthesis of QS-21-Based Immunoadjuvants," The Journal of Organic Chemistry, vol. 78 (2013), pp. 11525-11534.

Chea, Eric K., et al., "Synthesis and Preclinical Evaluation of QS-21 Variants Leading to Simplified Vaccine Adjuvants and Mechanistic Probes," Journal of the American Chemical Society, vol. 134 (2012), pp. 13448-13457.

Zheng, Quan, et al, "Pancreatic Lipase-Inhibiting Triterpenoid Saponins from Gypsophila oldhamiana," Chem. Pahrm. Bull., vol. 55, No. 4 (2007), pp. 646-650.

Nagao, Tsuneatsu, et al., "Studies on the Constituents of Thladiantha dubia Bunge. I. The Structures of Dubiosides A, B and C, the Quillaic Acid Glucuronide Saponins Isolated from the Tuber," Chem. Pharm. Bull., vol. 37, No. 4 (1989), pp. 925-929.

Wang, Pengfei, et al., "Vaccine Adjuvants Derivatized from Momordica Saponins I and II," J. Med. Chem., vol. 62 (2019), pp. 9976-9982.

Wang, Pengfei, et al., "Structural Effect on Adjuvanticity of Saponins," Journal of Medical Chemistry, vol. 63 (2020). pp. 3290-3297.

International Search Report and Written Opinion for PCT/US2020/023185 mailed on Jul. 28, 2020.

Iwamoto et al. "Studies on the Constituents of Momordica cochinchinensis Spreng. II. Isolation and Characterization of the Root Saponins, Momordins I, II and III", Chem. Pharm. Bull. 1985. vol. 33(1), pp. 1-7.

Fan et al. "Two New Oleanane-type Triterpenoids from Methanolyzed Saponins of Momordica cochinchinensis", Natural Product Communications. 2016. vol. 11 (6), pp. 725-728.

Iwamoto et al. "Studies on the Constituents of Momordica cochinchinensis Spreng. I. Isolation and Characterization of the Seed Saponins, Momordica Saponins I and 11", Chem. Pharm. Bull. 1985. vol. 33(2), pp. 464-478.

Takahashi et al. "Inhibition of human renin activity by saponins", Biomedical Research. 2010. vol. 31(2), pp. 155-159.

Song et al. "Adjuvant activities of saponins from traditional Chinese medicinal herbs", Vaccine. 2009. vol. 27, pp. 4883-4890.

Ashtekar, Amit R et al. "A mucosal subunit vaccine protects against lethal respiratory infection with Francisella tularensis LVS." PloS one vol. 7,11 (2012): e50460. doi:10.1371/journal.pone.0050460.

Wang, Pengfei et al. "Synthesis and Evaluation of QS-21-Based Immunoadjuvants with a Terminal-Functionalized Side Chain Incorporated in the West Wing Trisaccharide." The Journal of organic chemistry vol. 81,20 (2016): 9560-9566. doi:10.1021/acs.joc.6b00922.

* cited by examiner

|  | R1 | R2 | R3 | R4 |
|---|---|---|---|---|
| MS I (3) | H | xyl | H | rha |
| MS II (4) | H | xyl | OH | rha |

NMM, HOBt, EDC·HCl, CH₃(CH₂)₁₁NH₂
―――――――――――――――――――――
H₂O/EtOH, r.t.

5: R₁ = H
6: R₁ = OH

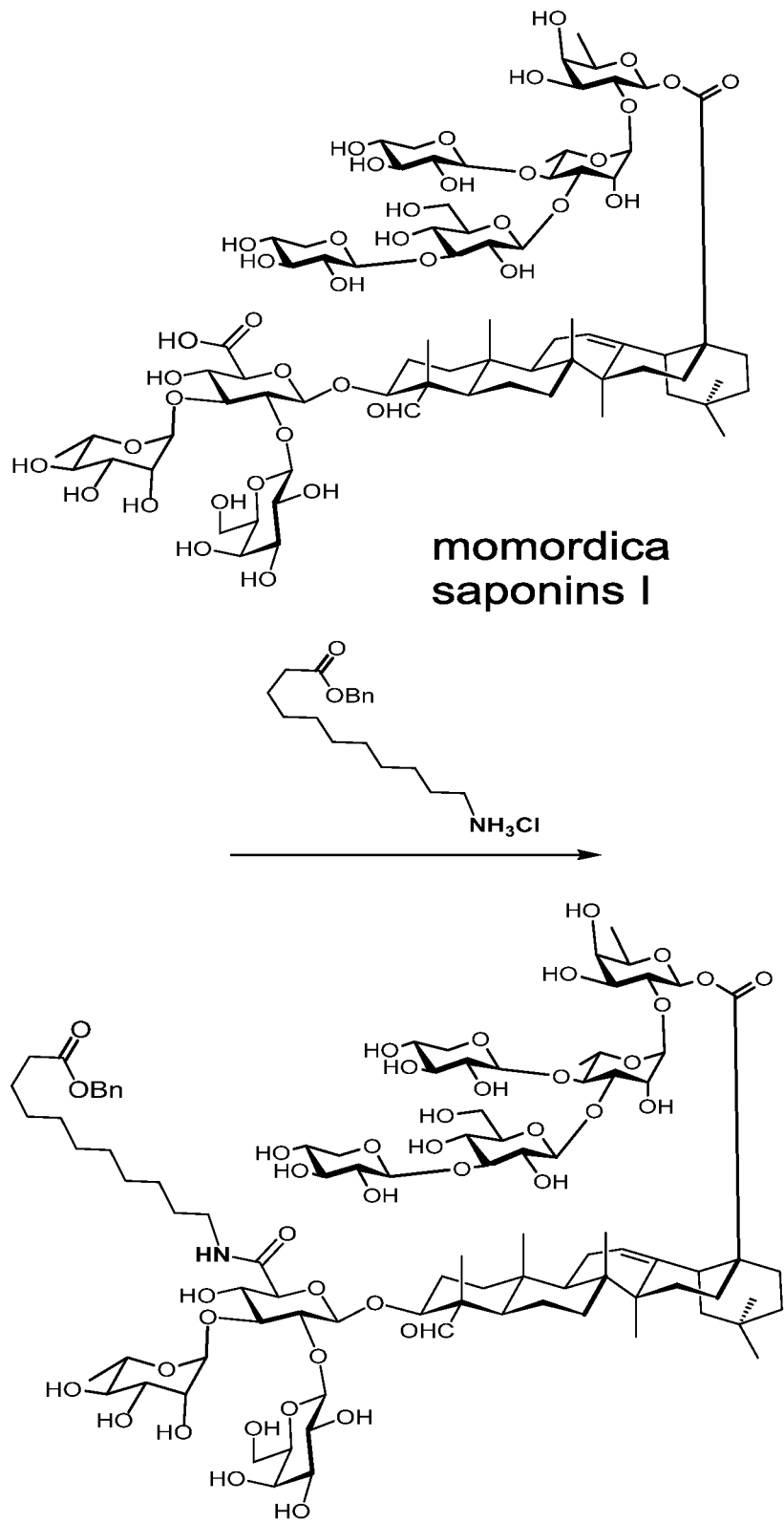
Fig. 4-cont'd a-c. $ROOC(CH_2)_nNH_2$, R = H, Me, Bn
d-f. $RCONH(CH_2)_nNH_2$, R = H, Me, Ph
g. $OH(CH_2)_nNH_2$ h. 
i. $OHC(CH_2)_nNH_2$ j.

k.

l.

n = 8-12

23d:
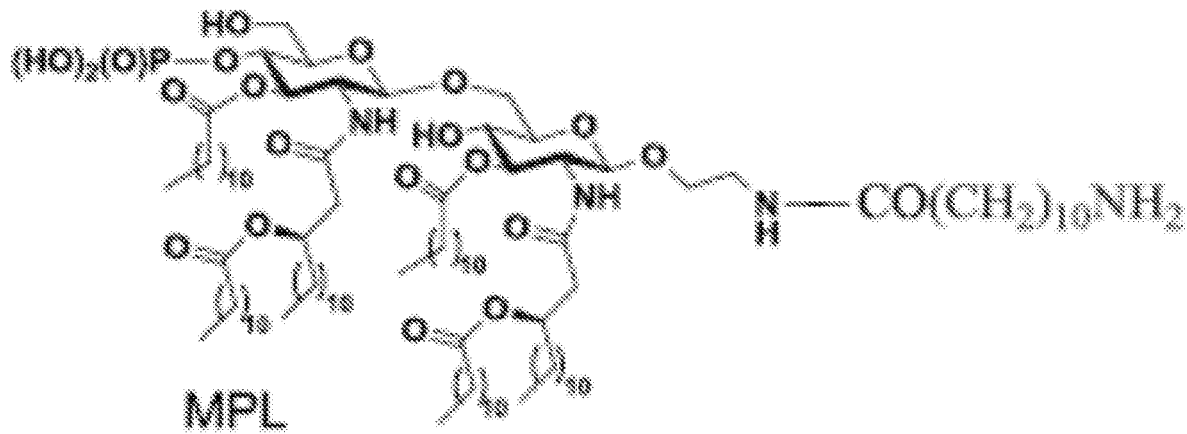
MPL
23b:
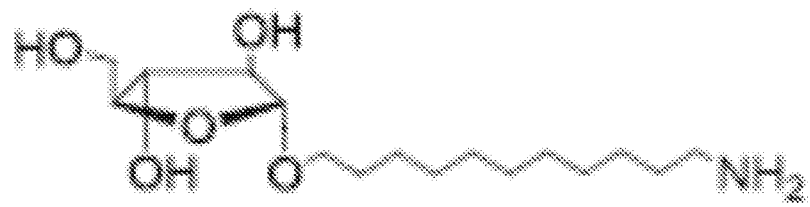
23e:
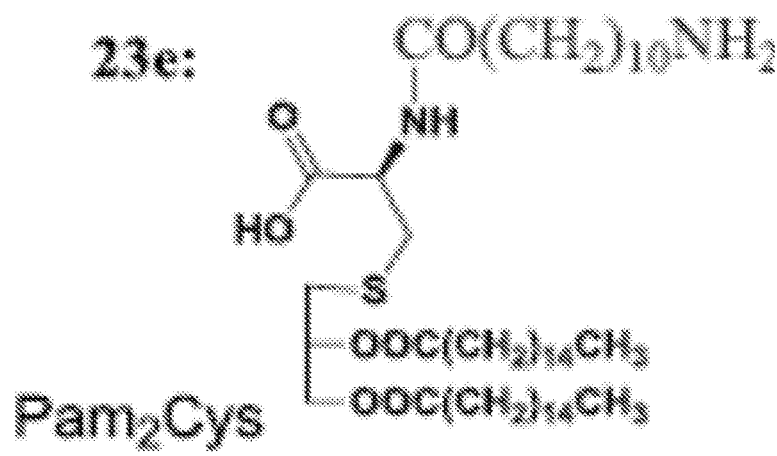
Pam₂Cys
*Fig. 5-cont'd* aReagents and conditions: (a) NMM, HOBt, EDC·HCl, NH$_2$(CH$_2$)$_{10}$COOBn, H$_2$O/EtOH, r.t., 78% for 4b and 72% for 5b; (b) Pd/C, H$_2$ (55 psi), 98% for 4c and 96% for 5c.

aReagents and conditions: (a) Pd/C, H$_2$ (55 psi); (b) NMM, HOBt, EDC·HCl, NH$_2$(CH$_2$)$_{10}$COOBn, H$_2$O/EtOH, r.t., 52% over two steps; (c) K$_2$CO$_3$, MeOH/H$_2$O, 57%; (d) Pd/C, H$_2$ (50 psi), 96%.

SAPONIN-BASED VACCINE ADJUVANTS

CROSS-REFERENCE TO RELATED APPLICATION

This application is the 35 U.S.C. § 371 national stage application of PCT Application No. PCT/US2020/023185, entitled "SAPONIN-BASED VACCINE ADJUVANTS", filed Mar. 17, 2020, where the PCT claims priority to U.S. Provisional Application No. 62/820,477, entitled "SAPONIN-BASED VACCINE ADJUVANTS" filed on Mar. 19, 2019, the entireties of which are herein incorporated by reference.

STATEMENT ON FUNDING PROVIDED BY THE U.S. GOVERNMENT

This invention was made with Government support under contract R01 GM120159 awarded by the National Institutes of Health. The Government has certain rights in the invention.

BACKGROUND

Vaccine adjuvants are the substances used with a vaccine to potentiate host's immune responses to the specific antigen(s) introduced by the vaccine (Brunner et al., (2010) Immunol. Lett. 128:29-35; Kensil et al., (2004) Frontiers Biosci. 9:2972-2988; Leroux-Roels G. (2010) Vaccine 28 (Suppl 3): C25-36; Sharp & Lavelle (2012) Development Therapeutic Agents Handbook John Wiley & Sons, Inc; pp. 533-546; Wang W. (2011) World J. Vaccines 1:33-78; Weeratna & McCluskie (2011) Recent Advan. Vaccine Adjuvants. pp. 303-322; Cox & Coulter (1997) Vaccine 15:248-256; Klebanoff et al., (2010) Immunol. Rev. 239:27-44; Plotkin SA. (2005) Nat. Med. 11: S5-S11; Rappuoli & Aderem (2011) Nature 473: 463-469; Kensil et al., (2005) Vaccine Adjuvants: Immunological and Clinical Principles Humana Press Inc. pp. 221-234).

Vaccine adjuvants also tune immune system to the desirable responses for certain pathogens. For example, QS-21, a mixture of two isomers, is an FDA-approved adjuvant known for its capacity of potentiating a balanced Th1/Th2 response with antigen-specific CTL production, which is valuable for vaccines against intracellular pathogens and cancers (Ragupathi et al., (2011) Expert Rev. Vaccines 10:463-470; Deng et al., (2008) Angew Chem. Int. 47:6395-6398; Kensil C R. (1996) Critical Revs. Therap. Drug Carrier Systs. 13:1-55; Kensil et al., (1991) J. Immun. 146:431-437). It has potential for a wide range of clinical applications and thus to be in high demand (Kensil et al., (1991) J. Immun. 146:431-437). Supplies of QS-21 are very limited. The natural products are isolated from the tree bark of Quillaja saponaria Molina (QS), an evergreen tree native to warm temperate central Chile. However, overexploitation of the natural source has resulted in ecological and economic consequences even under the current demand (Ragupathi et al., (2010) Vaccine 28:4260-4267). Moreover, the abundance of QS-21 in QS tree bark extracts is low and its isolation is laborious (Kensil et al., (1991) J. Immun. 146: 431-437; Ragupathi et al., (2010) Vaccine 28:4260-4267; Wang et al., (2005) J. Am. Chem. Soc. 127:3256-3257). QS-21 also has a chemical instability issue due to two hydrolytically unstable ester moieties that complicate its formulation; its dose-limiting toxicity also prevents it from reaching the full potency. QS-21 analogs bearing a plain dodecyl side chain or a side chain with a terminal carboxyl group have been shown to have different adjuvant activities (Adams et al., (2010) J. Am. Chem. Soc. 132:1939-1945; Chea et al., (2012) J. Am. Chem. Soc. 134:13448-13457).

Derivatization of Momordica saponin (MS) I (2) and II (3) has been shown to be a potentially viable way to achieve the goal of practical alternatives to QS-21 (Wang et al., (2019) J. Med. Chem. 62:9976-9982). MS I and II are isolated from the seeds of the perennial Momordica cochinchinensis Spreng (MC) that grows in China and Southeast Asia (Lieberman et al., (2009) Clin. Vaccine Immunol. 16:1332-1337). The seeds are widely available and inexpensive. Incorporation of an aliphatic dodecyl chain to MS I at the C3 glucuronic acid led to derivative VSA-1 (4a) with a significantly different adjuvant activity profile from the natural precursor (Slovin et al., (2005) Vaccine 23:3114-3122), in particular by enhancing antigen-specific IgG2a response. Another MS II derivative, 5a, did not have such a significant change in IgG1 and IgG2a responses and its natural saponin precursor 3 even though the two MS derivatives, 4a and 5a, only differ in their respective structure at C16 of the triterpenoid core of 4a versus the quillaic acid core of 5a.

SUMMARY

One aspect of the disclosure encompasses embodiments of a modified saponin having the formula:

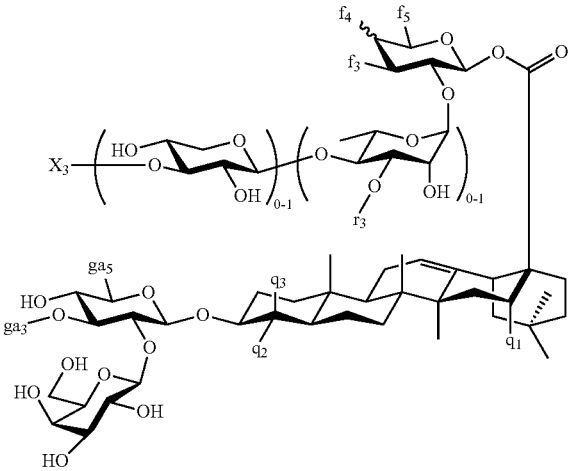

wherein: $q_1$ can be H or OH; $q_2$ and $q_3$ can be each independently selected from CHO, $CH_3$, $CH_2OH$, H, or a component of an acetal group; $f_3$ and $f_4$ can be each independently OH or an acetyl, or C3 and C4 of a fuocsyl unit wherein $f_3$, and $f_4$ can form a cyclic ketal ring or cyclic carbonate ester; $f_5$ and $ga_5$ can be each independently selected from the group consisting of H, a methyl group, a carboxyl group, $R_4$—$NR_5$—$C(O)$—, and $R_4$—O—, wherein $R_4$ and $R_5$ can be each independently a linear chain having the structure $R_6$ $(CH_2)_{0\text{-}20}$— or $R_6[(CH_2)_{0\text{-}20}O_{0\text{-}20}$ $(CH_2)_{0\text{-}20}]_{0\text{-}20}$, wherein $R_6$ can be H, OH, $COO(CH_2)_{0\text{-}6}H$, COOBn, $C(O)NR_7Bn$, $NR_7Bn$, OBn, a saccharide unit, a Momordica saponin I or II, a muramyldipeptide, a monophosphoryl lipid A (MPL) unit, an α-Galcer unit, a dipalmitoyl-S-glyceryl cysteine (PamCys) unit, or a functional group of a carrier; and wherein $R_7$ can be H or an alkyl group; r3 can be H, a monosaccharide, disaccharide, or a trisaccharide; x3 can be H, a monosaccharide (except xylose) or a disaccharide; and ga3 can be H, a monosaccharide or a disaccharide.

In some embodiments of this aspect of the disclosure, the carrier can be selected from the group consisting of a polyamine polymer, a polyethylene glycol amine, poly (ethyleneimine), a nanocarbon, and an amino-containing biological molecule.

In some embodiments of this aspect of the disclosure, the modified saponin can have

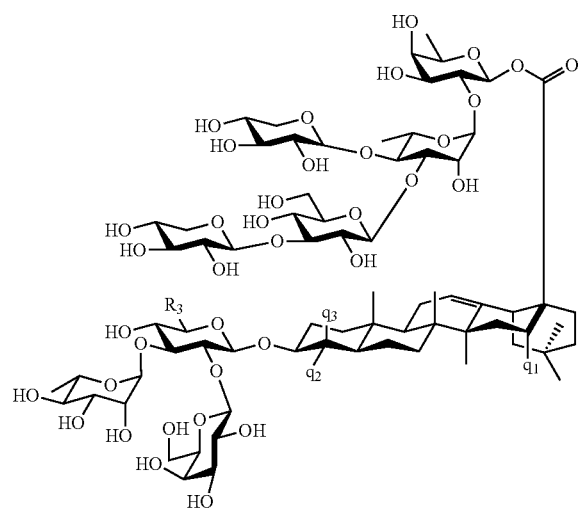

I wherein: $q_1$ can be H or OH; $q_2$ and $q_3$ can be each independently selected from CHO, $CH_3$, $CH_2OH$, H, or a component of an acetal group; and $R_3$ can be selected from the group consisting of H, a methyl group, a carboxyl group, $RA-NR_5-C(O)-$, and $R_4-O-$, wherein $R_4$ and $R_5$ can be each independently a linear chain having the structure $R_6(CH_2)_{0-20}-$ or $R_6[(CH_2)_{0-20}O_{0-20}(CH_2)_{0-20}]_{0-20}$, wherein Re can be H, OH, $COO(CH_2)_{0-6}H$, COOBn, $C(O)NR_7Bn$, $NR_7Bn$, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group of a carrier; and wherein Rz can be H or an alkyl group.

In some embodiments of this aspect of the disclosure, $R_3$ can be a carboxyl group.

In some embodiments of this aspect of the disclosure, $R_3$ can be $R_4-NH-C(O)-$, wherein $R_4$ can be a long-chain fatty acid having the structure $HOOC-(CH_2)_{6-20}-$.

In some embodiments of this aspect of the disclosure, $R_3$ can be an alkoxy group having the structure $H_3C-(CH_2)_{6-20}-O-CH_2$.

In some embodiments of this aspect of the disclosure, $R_3$ can be $R_4-NH-C(O)-$, wherein $R_4$ can be a long-chain alcohol having the structure $HO-(CH_2)_{6-20}-$.

In some embodiments of this aspect of the disclosure, $R_4$ can be a long-chain alkyl terminated with a functional group selected from an ester group, an ether group, an amino group, a cyano group, a carbonyl group, an azido group, and an aromatic group.

In some embodiments of this aspect of the disclosure, $R_3$ is $R_4-NH-C(O)-$, wherein $R_4$ can be a long-chain alkyl $R_6O(CH_2)_{6-20}-$, and wherein $R_6$ can be selected from a saccharide unit selected from the group consisting of a monosaccharide, a disaccharide, and trisaccharide.

In some embodiments of this aspect of the disclosure, $R_3$ can be $R_4-NH-C(O)-$, wherein $R_4$ can be a long-chain alkyl terminated with a monophosphoryl lipid A (MPL).

In some embodiments of this aspect of the disclosure, $R_3$ can be $R_4-NH-C(O)-$, and wherein $R_4$ can be a long-chain alkyl terminated with a dipalmitoyl-S-glyceryl cysteine ($Pam_2Cys$) or a tripalmitoyl-S-glyceryl cysteine ($Pam_3Cys$).

In some embodiments of this aspect of the disclosure, $R_3$ can be $R_4-NH-C(O)-$, wherein $R_4$ can be a long-chain alkyl terminated with a muramyldipeptide unit. In some embodiments of this aspect of the disclosure, $R_3$ can be $R_4-NH-C(O)-$, wherein $R_4$ can be a long-chain alkyl terminated with an α-Galcer unit.

In some embodiments of this aspect of the disclosure, $R_3$ can be $R_4-NH-C(O)-$, wherein $R_4$ can be a long-chain alkyl terminated with MS I unit.

In some embodiments of this aspect of the disclosure, $R_3$ can be $R_4-NH-C(O)-$, wherein $R_4$ can be a long-chain alkyl terminated with MS II unit.

In some embodiments of this aspect of the disclosure, the modified saponin can be selected from the group consisting of formulas A-E:

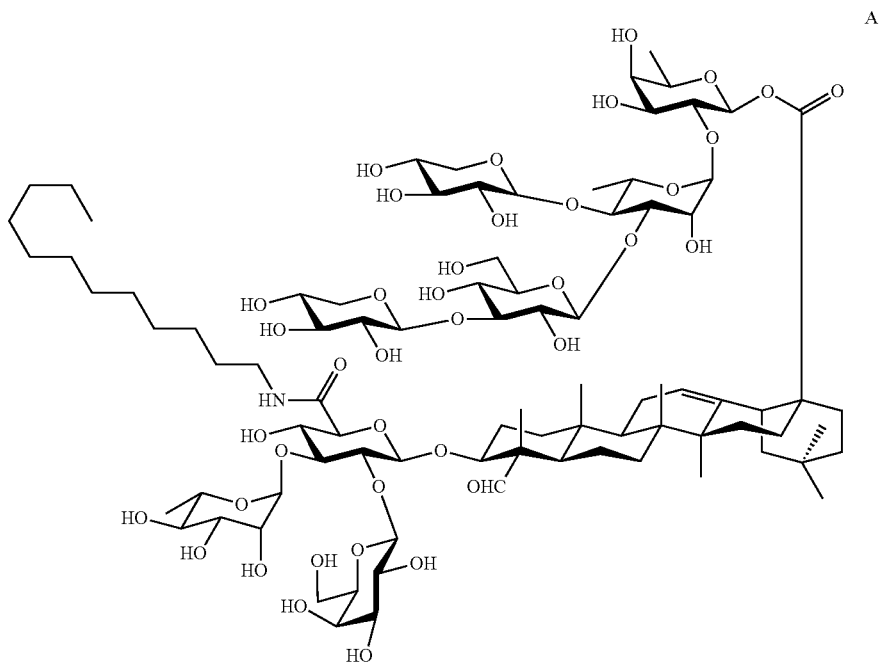

A

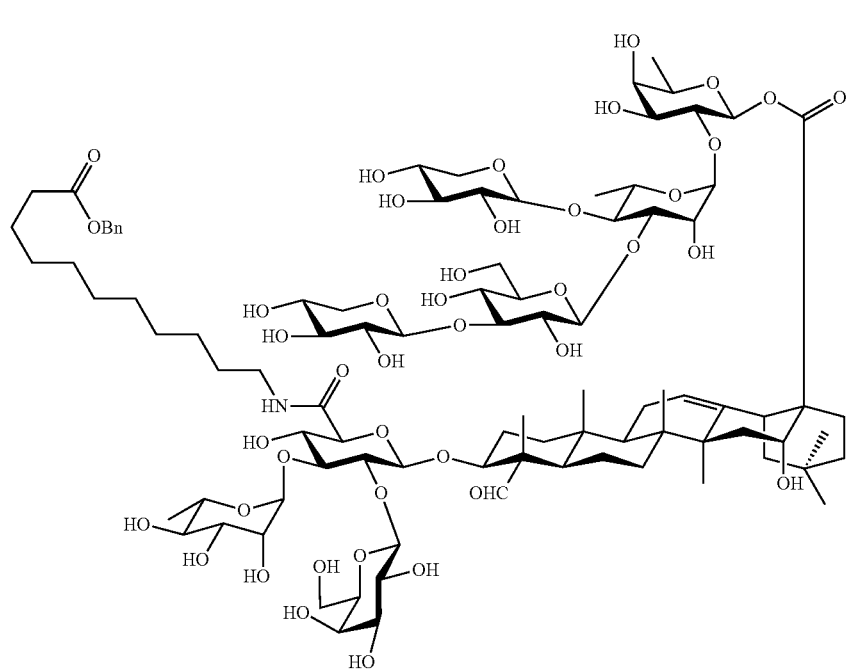
B
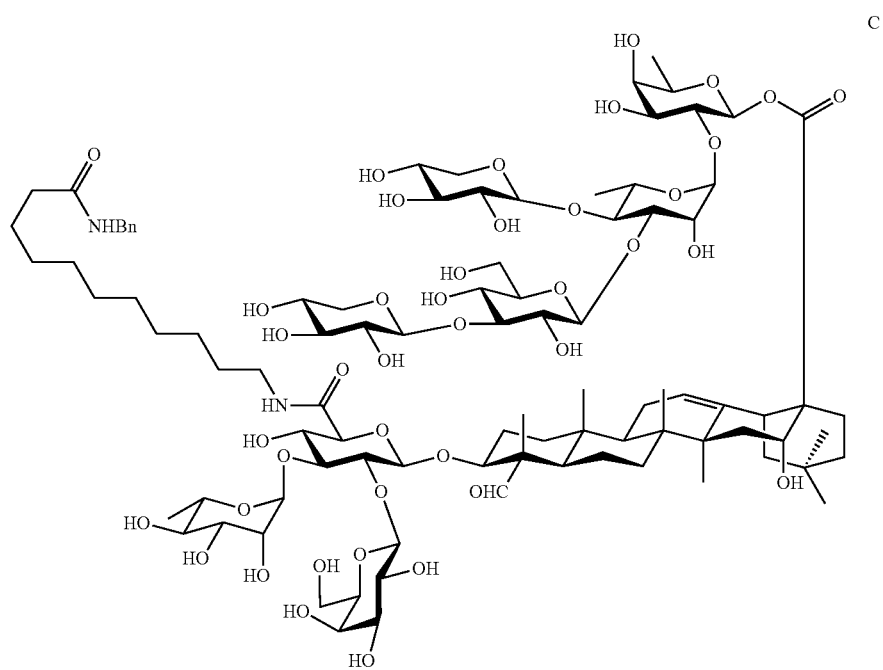
C

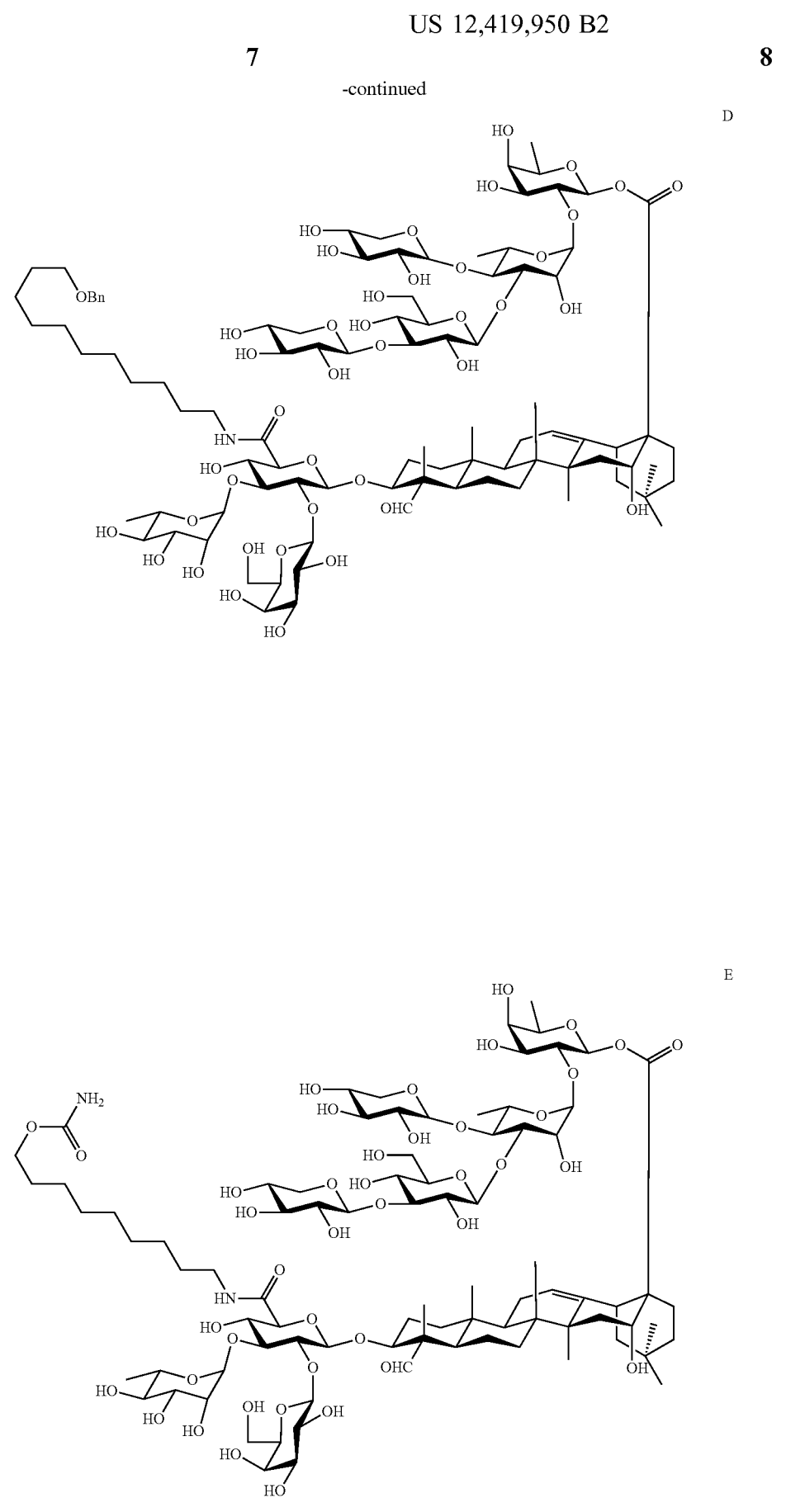

D

E

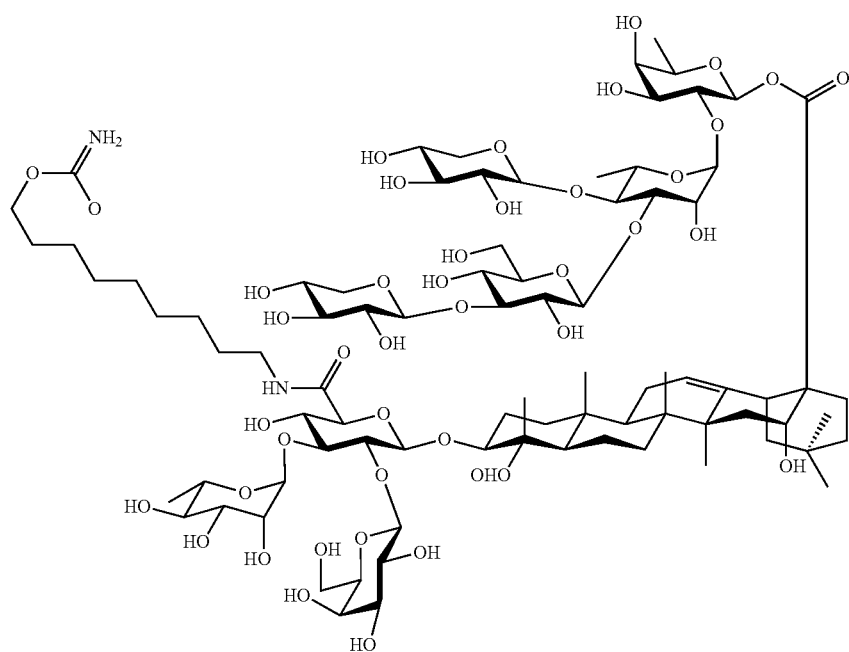

Another aspect of the disclosure encompasses embodiments of a pharmaceutical composition comprising a modified saponin having the formula:

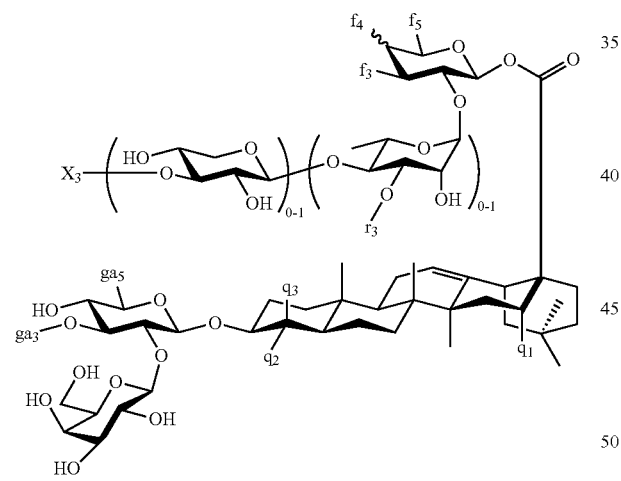

wherein: $q_1$ can be H or OH; $q_2$ and $q_3$ can be each independently selected from CHO, $CH_3$, $CH_2OH$, H, or a component of an acetal group; $f_3$ and $f_4$ can be each independently OH or an acetyl, or C3 and C4 of a fuocsyl unit wherein $f_3$, and $f_4$ can form a cyclic ketal ring or cyclic carbonate ester; $f_5$ and $ga_5$ can be each independently selected from the group consisting of H, a methyl group, a carboxyl group, $R_4$—$NR_5$—C(O)—, and $R_4$—O—, wherein $R_4$ and $R_5$ can be each independently a linear chain having the structure $R_6$($CH_2$)$_{0-20}$— or Re [($CH_2$)$_{0-20}$O$_{0-20}$ ($CH_2$)$_{0-20}$]$_{0-20}$, wherein $R_6$ can be H, OH, COO($CH_2$)$_{0-6}$H, COOBn, C(O)NR$_7$Bn, NR$_7$Bn, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group of a carrier; and wherein $R_7$ can be H or an alkyl group; r3 can be H, a monosaccharide, disaccharide, or a trisaccharide; x3 can be H, a monosaccharide (except xylose) or a disaccharide; and ga3 can be H, a monosaccharide or a disaccharide.

In some embodiments of this aspect of the disclosure, the carrier can be selected from the group consisting of a polyamine polymer, a polyethylene glycol amine, poly (ethyleneimine), a nanocarbon, and an amino-containing biological molecule.

In some embodiments of this aspect of the disclosure, the modified saponin can have the formula I:

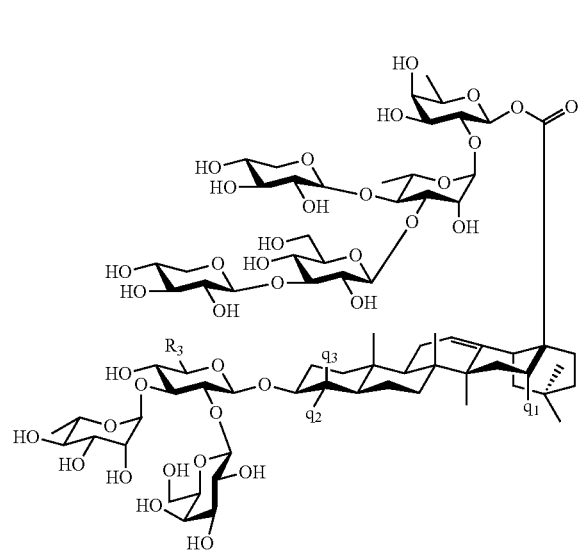

wherein: $q_1$ can be H or OH; $q_2$ and $q_3$ can be each independently selected from CHO, $CH_3$, $CH_2OH$, H, or a component of an acetal group; and $R_3$ can be selected from the group consisting of H, a methyl group, a carboxyl group, $R_4$—$NR_5$—C(O)—, and $R_4$—O—, wherein $R_4$ and $R_5$ can be each independently a linear chain having the structure $R_6(CH_2)_{0-20}$— or $R_6[(CH_2)_{0-20}O_{0-20}(CH_2)_{0-20}]_{0-20}$, wherein $R_6$ can be H, OH, $COO(CH_2)_{0-6}H$, COOBn, $C(O)NR_7Bn$, $NR_7Bn$, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group of a carrier; and wherein $R_7$ can be H or an alkyl group.

In some embodiments of this aspect of the disclosure, $R_3$ is a carboxyl group.

In some embodiments of this aspect of the disclosure, $R_3$ is $R_4$—NH—C(O)—, wherein $R_4$ is a long-chain fatty acid having the structure HOOC—$(CH_2)_{6-20}$—.

In some embodiments of this aspect of the disclosure, $R_3$ can be an alkoxy group having the structure $H_3C$—$(CH_2)_{6-20}$—O—.

In some embodiments of this aspect of the disclosure, $R_3$ can be $R_4$—NH—C(O)—, wherein $R_4$ can be a long-chain alcohol having the structure HO—$(CH_2)_{6-20}$—.

In some embodiments of this aspect of the disclosure, $R_4$ can be a long-chain alkyl terminated with a functional group selected from an ester group, an ether group, an amino group, a cyano group, a carbonyl group, an azido group, and an aromatic group.

In some embodiments of this aspect of the disclosure, $R_3$ can be an alkoxy group having the structure $H_3C$—$(CH_2)_{6-20}$—O—$CH_2$—.

In some embodiments of this aspect of the disclosure, $R_3$ can be $R_4$—NH—C(O)—, wherein $R_4$ is a long-chain alcohol having the structure HO—$(CH_2)_{6-20}$—.

In some embodiments of this aspect of the disclosure, $R_4$ can be a long-chain alkyl terminated with a functional group selected from an ester group, an ether group, an amino group, a cyano group, a carbonyl group, an azido group, and an aromatic group.

In some embodiments of this aspect of the disclosure, $R_3$ can be $R_4$—NH—C(O)—, wherein $R_4$ can be a long-chain alkyl $R_{60}$ $(CH_2)_{6-20}$— and Re can be selected from a saccharide unit selected from the group consisting of a monosaccharide, a disaccharide, and trisaccharide.

In some embodiments of this aspect of the disclosure, $R_3$ can be $R_4$—NH—C(O)—, wherein $R_4$ can be a long-chain alkyl terminated with a monophosphoryl lipid A (MPL).

In some embodiments of this aspect of the disclosure, $R_3$ is $R_4$—NH—C(O)—, wherein $R_4$ can be a long-chain alkyl terminated with a dipalmitoyl-S-glyceryl cysteine ($Pam_2Cys$) or a tripalmitoyl-S-glyceryl cysteine ($Pam_3Cys$).

In some embodiments of this aspect of the disclosure, $R_3$ can be $R_4$—NH—C(O)—, wherein $R_4$ can be a long-chain alkyl terminated with a muramyldipeptide unit.

In some embodiments of this aspect of the disclosure, $R_3$ can be $R_4$—NH—C(O)—, wherein $R_4$ can be a long-chain alkyl terminated with an α-Galcer unit.

In some embodiments of this aspect of the disclosure, $R_3$ can be $R_4$—NH—C(O)—, wherein $R_4$ can be a long-chain alkyl terminated with MS I unit.

In some embodiments of this aspect of the disclosure, $R_3$ can be $R_4$—NH—C(O)—, wherein $R_4$ can be a long-chain alkyl terminated with MS II unit.

In some embodiments of this aspect of the disclosure, the modified saponin can be selected from the group consisting of formulas A-E:

-continued
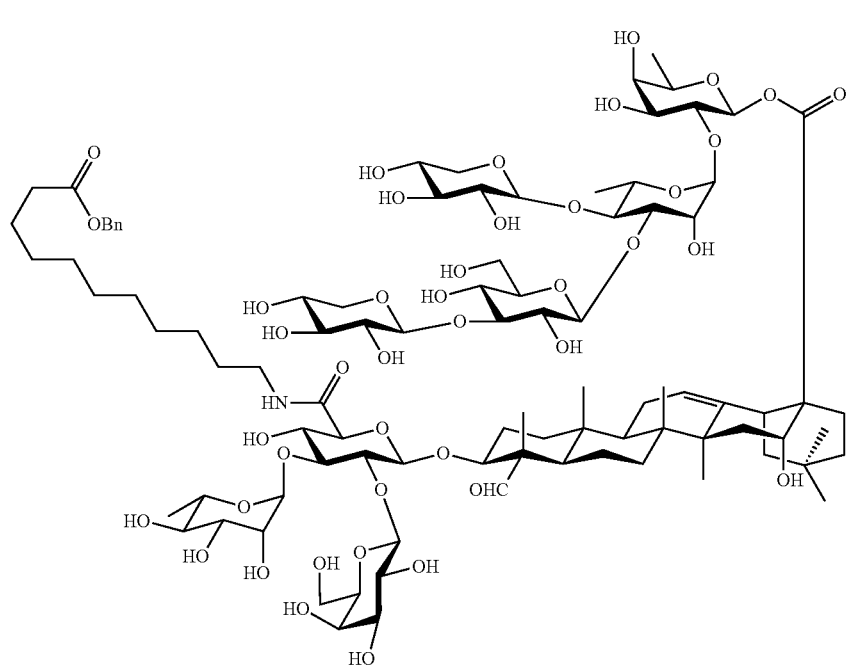
B
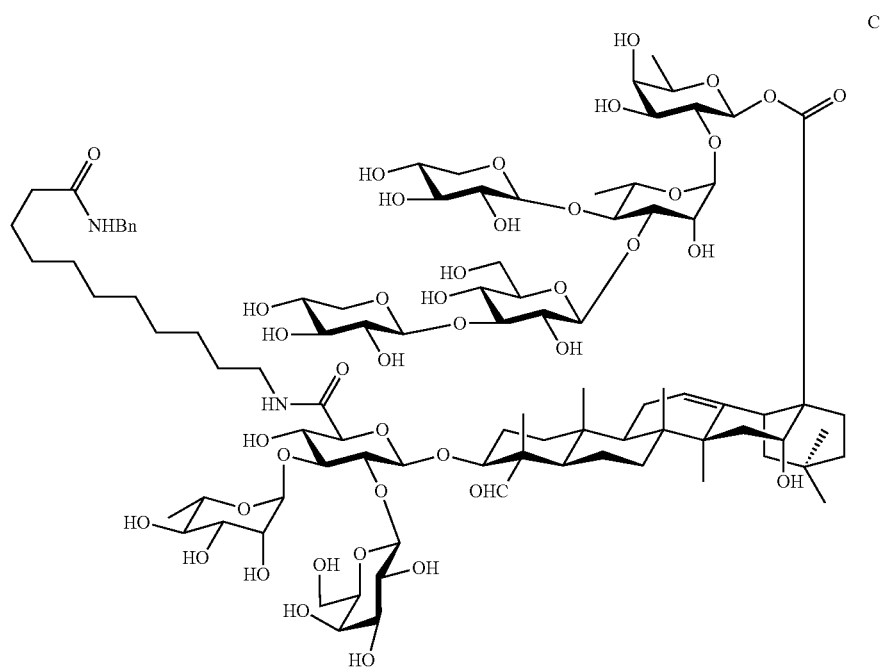
C

In some embodiments of this aspect of the disclosure, the pharmaceutical composition can further comprise at least one immunogen.

In some embodiments of this aspect of the disclosure, the pharmaceutical composition can further comprise a pharmaceutically acceptable carrier.

In some embodiments of this aspect of the disclosure, the pharmaceutical composition can be formulated for administering to an animal or human subject.

In some embodiments of this aspect of the disclosure, the pharmaceutical composition can further comprise at least one cancer therapeutic agent, wherein the at least one chemotherapeutic agent and the saponin derivative are admixed in a pharmaceutically acceptable formulation or covalently linked to each other, and a pharmaceutically acceptable carrier.

Yet another aspect of the disclosure encompasses embodiments of a method of increasing the immunogenicity of an immunogen when administered to an animal or human subject, the method comprising the step of administering to the subject a vaccine comprising at least a pharmaceutical composition according to the disclosure.

Still yet another aspect of the disclosure encompasses embodiments of a synthetic route for the synthesis of a saponin derivative, the synthetic route comprising coupling a natural saponin with a functionalized side chain molecule, wherein the functionalized side chain comprises an amino group or hydroxyl group.

In some embodiments of this aspect of the disclosure, the natural saponin can be obtained from *Momordica cochinchinensis* Spreng.

In some embodiments of this aspect of the disclosure, the natural saponin can be coupled to the functionalized side chain molecule via an amide formation reaction or an ester formation reaction.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 6A illustrates serum IgG anti-OVA responses in mice immunized by the subcutaneous route with ovalbumin (OVA) alone, with GPI-0100, and OVA with the natural saponins 3 or 4, or their respective derivatives 5 or 6.

FIG. 6B illustrates serum IgG1, and IgG2a anti-OVA responses in mice immunized by the subcutaneous route with ovalbumin (OVA) alone, with GPI-0100, and OVA with the natural saponins 3 or 4, or their respective derivatives 5 or 6.

FIG. 6C illustrate serum IgG2a anti-OVA responses in mice immunized by the subcutaneous route with ovalbumin (OVA) alone, with GPI-0100, and OVA with the natural saponins 3 or 4, or their respective derivatives 5 or 6.

FIG. 9A illustrates a serum IgG anti-OVA response in mice immunized by the s.c. route with OVA alone or with GPI-0100 or a MS derivative.

FIG. 9B illustrates a serum IgG1 anti-OVA response in mice immunized by the s.c. route with OVA alone or with GPI-0100 or a MS derivative.

FIG. 9C illustrates a serum IgG2a anti-OVA response in mice immunized by the s.c. route with OVA alone or with GPI-0100 or a MS derivative.

FIG. 9D illustrates exemplary MS derivatives.

FIG. 10A illustrates a serum IgG anti-rHagB response in mice immunized by the s.c. route with rHagB alone or with GPI-0100 or a saponin adjuvant.

FIG. 10B illustrates a serum IgG1 anti-anti-rHagB response in mice immunized by the s.c. route with rHagB alone or with GPI-0100 or a saponin adjuvant.

FIG. 10C illustrates a serum IgG2a anti-anti-rHagB response in mice immunized by the s.c. route with rHagB alone or with GPI-0100 or a saponin adjuvant.

FIG. 10D illustrates saponin derivatives 5b, 5c, 9b, and 9c.

DETAILED DESCRIPTION

Figure 1:
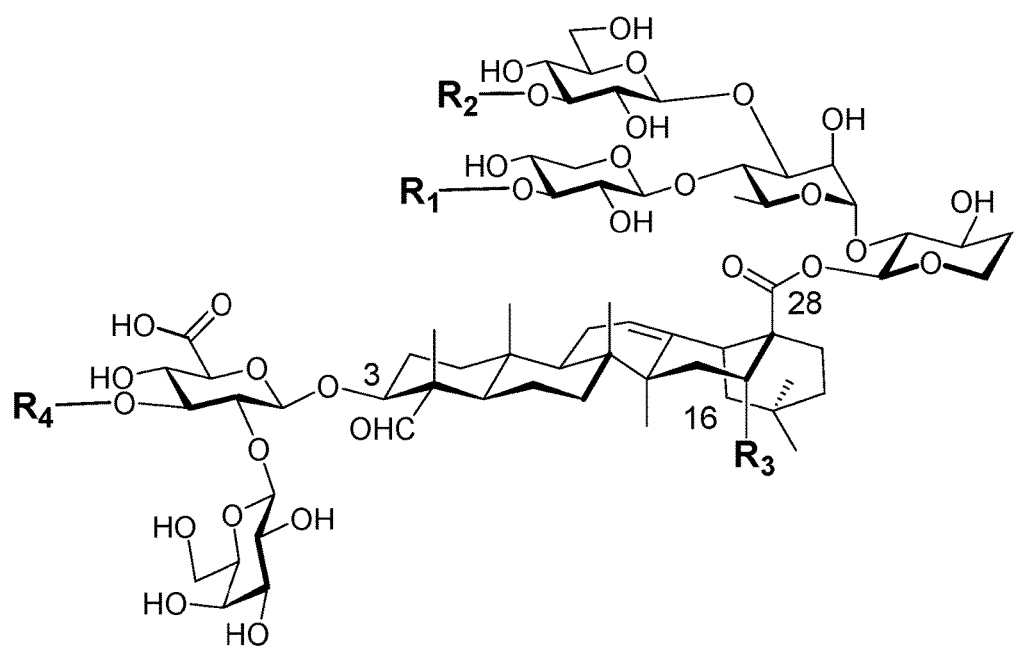
FIG. 1 illustrates natural saponin MS I and MS II and derivatives thereof.
Figure 2:
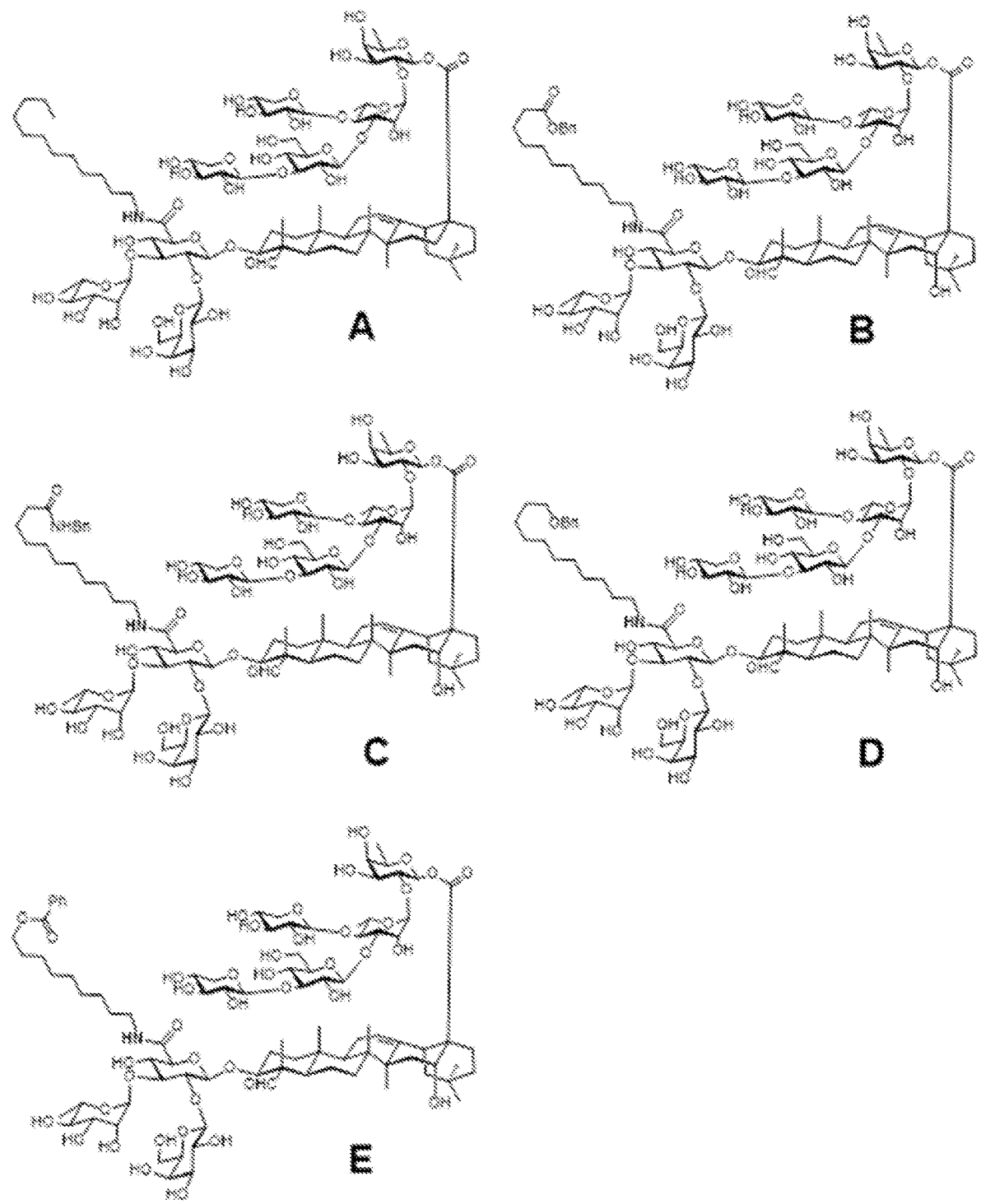
FIG. 2 illustrates derivatives A-E of the disclosure.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions

The term "acyl" as used herein, alone or in combination, means a carbonyl or thiocarbonyl group bonded to a radical selected from, for example, optionally substituted, hydrido, alkyl (e.g. haloalkyl), alkenyl, alkynyl, alkoxy ("acyloxy" including acetyloxy, butyryloxy, iso-valeryloxy, phenylacetyloxy, berizoyloxy, p-methoxybenzoyloxy, and substituted acyloxy such as alkoxyalkyl and haloalkoxy), aryl, halo, heterocyclyl, heteroaryl, sulfonyl (e.g. allylsulfinylalkyl), sulfonyl (e.g. alkylsulfonylalkyl), cycloalkyl, cycloalkenyl, thioalkyl, thioaryl, amino (e.g alkylamino or dialkylamino), and aralkoxy. Illustrative examples of "acyl" radicals are formyl, acetyl, 2-chloroacetyl, 2-bromacetyl, benzoyl, trifluoroacetyl, phthaloyl, malonyl, nicotinyl, and the like. The term "acyl" as used herein refers to a group-C(O) $R_{26}$, where $R_{26}$ is hydrogen, alkyl, cycloalkyl, cyclo-heteroalkyl, aryl, arylalkyl, heteroalkyl, heteroaryl, and heteroarylalkyl. Examples include, but are not limited to formyl, acetyl, cyclohexylcarbonyl, cyclohexylmethylcarbonyl, benzoyl, beozylcarbonyl and the like.

The term "adjuvant molecule" as used herein refers to surface proteins capable of eliciting an immune response in a host. In particular embodiments, the adjuvant molecule is a "membrane-anchored form" of the adjuvant molecule which indicates that the adjuvant molecule has been engineered to include a signal peptide (SP) and a membrane anchor sequence to direct the transport and membrane orientation of the protein. Thus, in embodiments, a membrane-anchored form of an adjuvant molecule is a recombinant protein including a portion of a protein fused to a SP and membrane anchor sequence.

The terms "administering" and "administration" as used herein refer to introducing a composition (e.g., a vaccine, adjuvant, or immunogenic composition) of the present disclosure into a subject. A preferred route of administration of the vaccine composition is intravenous.

The terms "alkoxyl" or "alkoxyalkyl" as used herein refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkyl", either alone or within other terms such as "thioalkyl" and "arylalkyl", as used herein, means a monovalent, saturated hydrocarbon radical which may be a straight chain (i.e. linear) or a branched chain. An alkyl radical for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-actyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl radical is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the disclosure and do not significantly reduce the efficacy of the compounds. In certain aspects of the disclosure, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

The term "antibody" as used herein refers to polyclonal and monoclonal antibody preparations, as well as preparations including hybrid antibodies, altered antibodies, F (ab')$_2$ fragments, F (ab) fragments, Fv fragments, single domain antibodies, chimeric antibodies, humanized antibodies, and functional fragments thereof which exhibit immunological binding properties of the parent antibody molecule.

The term "antibody" as used herein further refers to an immunoglobulin which specifically binds to and is thereby defined as complementary with a particular spatial and polar organization of another molecule. The antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, IgY, etc. Fragments thereof may include Fab, Fv and F(ab')$_2$, Fab', scFv, and the like. In addition, aggregates, polymers, and conjugates of immunoglobulins or their fragments can be used where appropriate so long as binding affinity for a particular molecule is maintained.

The term "antigen" as used herein refers to a molecule with one or more epitopes that stimulate a host's immune system to make a secretory, humoral and/or cellular antigen-specific response, or to a DNA molecule that is capable of producing such an antigen in a vertebrate. The term is also used interchangeably with "immunogen." For example, a specific antigen can be complete protein, portions of a protein, peptides, fusion proteins, glycosylated proteins and combinations thereof. For use with the compositions of the present disclosure, one or more PvDBPII antigens (native protein or protein fragment), may be provided directly or as part of a recombinant nucleic acid expression system to provide an antigenic PvDBPII product to trigger a host immune response.

The term "antigenic component" as used herein refers to a component derived from an organism capable of stimulating an immune response in an animal, preferably a mammal including mouse and human. An antigenic component may be an immunogenic agent. The antigenic component may comprise sub-cellular components including, organelles, membranes, proteins, lipids, glycoproteins and other components derived from the organism. The antigenic component may be derived from a whole organism, for example a whole parasite, or a part of an organism, for example a cell or tissue of an organism. Also, a sub-set of proteins may be purified, for example by size fractionation or affinity purification, and recombined.

The terms "sugar" and "saccharide" as used herein refers to a polyhydroxyaldehyde, polyhydroxyketone and derivatives thereof. The term includes monosaccharides such as erythrose, arabinose, allose, altrose, glucose, mannose, threose, xylose, gulose, idose, galactose, talose, aldohexose, fructose, ketohexose, ribose, and aldopentose. The term also includes carbohydrates composed of monosaccharide units, including disaccharides, oligosaccharides, or polysaccharides. Examples of disaccharides are sucrose, lactose, and maltose. Oligosaccharides generally contain between 3 and 9 monosaccharide its and polysaccharides contain greater than 10 monosaccharide units. A sugar may be a member of the D or L series and can include amino sugars, deoxy sugars, and their uronic acid derivatives. In embodiments of the disclosure where the carbohydrate is a hexose, the hexose is glucose, galactose, or mannose, or substituted hexose sugar residues such as an amino sugar residue such as hexosamine, galactosamine; glucosamine, in particular D-glucosamine (2-amino-2-doexy-D-gluoose) or D-galactosamine (2-amino-2-deoxy-D-galactose). Illustrative pentose sugars include arabinose, fucose, and ribose. A sugar residue may be linked to a compound of the disclosure from a 1,1 linkage, 1,2 linkage, 1,3 linkage, 1,4 linkage, 1,5 linkage, or 1,6 linkage. A linkage may be via an oxygen atom of a compound of the disclosure. An oxygen atom can be replaced one or more times by —$CH_2$— or —S— groups.

The term "carboxyl" as used herein, alone or in combination, refers to —C(O)OR$_{25}$— or —C(—O)OR$_{25}$ wherein R$_{25}$ is hydrogen, alkyl, alkenyl, alkynyl, cycloalkyl, cycloalkenyl, amino, thiol, aryl, heteroaryl, thioalkyl, thioaryl, thioalkoxy, a heteroaryl, or a heterocyclic, which may optionally be substituted. In aspects of the disclosure, the carboxyl groups are in an esterified form and may contain as an esterifying group lower alkyl groups. In particular aspects of the disclosure, —C(O)OR$_{25}$ provides an ester or an amino acid derivative. An esterified form is also particularly referred to herein as a "carboxylic ester". In aspects of the disclosure a "carboxyl" may be substituted, in particular substituted with allyl which is optionally substituted with one or more of amino, amine, halo, alkylamino, aryl, carboxyl, or a heterocyclic. Examples of carboxyl groups are methoxycarbonyl, butoxycarbonyl, tert.alkoxycarbonyl such as tert.butoxycarbonyl, arylmethyoxycarbonyl having one or two aryl radicals including without limitation phenyl optionally substituted by for example lower alkyl, lower alkoxy, hydroxyl, halo, and/or nitro, such as benzyloxycarbonyl, methoxybenzyloxycarbonyl, diphenylmethoxycarbonyl, 2-bromoethoxycarbonyl, 2-iodoethoxycarbonyltert.butylcarborlyl, 4-nitrobenzyloxycarbonyl, diphenylmethoxycarbonyl, benzhydroxycarbonyl, di-(4-methoxyphenyl-methoxycarbonyl, 2-bromoethoxycarbonyl, 2-iodoethoxycarbonyl, 2-trimethylsilylethoxycarbonyl, or 2-triphenylsilylethoxycarbonyl. Additional carboxyl groups in esterified form are silyloxycarbonyl groups including organic silyloxycarbonyl. The silicon substituent in such compounds may be substituted with lower alkyl (e.g. methyl), alkoxy (e.g. methoxy), and/or halo (e.g. chlorine). Examples of silicon substituents include trimethylsilyi and dimethyltert.butylsilyl. In aspects of the disclosure, the carboxyl group may be an alkoxy carbonyl, in particular methoxy carbonyl, ethoxy carbonyl, isopropoxy carbonyl, t-butoxycarbonyl, t-pentyloxycarbonyl, sir heptyloxy carbonyl, especially methoxy carbonyl or ethoxy carbonyl.

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

When a compound of the present disclosure is used contemporaneously with one or more other drugs, a pharmaceutical composition containing such other drugs in addition to the compound of the present disclosure is contemplated. Accordingly, the pharmaceutical compositions of the present disclosure include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used. Thus, for example, but not intended to be limiting, when a compound of the present disclosure is combined with another agent, the weight ratio of the compound of the present disclosure to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used. In such combinations the compound of the present disclosure and other active agents may be administered separately or in conjunction. In addition, the administration of one element may be prior to, concurrent to, or subsequent to the administration of other agent(s).

A composition of the disclosure can be a liquid solution, suspension, emulsion, tablet, pill, capsule, sustained release formulation, or powder. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Various delivery systems are known and can be used to administer a composition of the disclosure, e.g. encapsulation in liposomes, microparticles, microcapsules, and the like.

A therapeutic composition of the disclosure may comprise a carrier, such as one or more of a polymer, carbohydrate, peptide or derivative thereof, which may be directly or indirectly covalently attached to the compound. A carrier may be substituted with substituents described herein including without limitation one or more alkyl, amino, nitro, halogen, thiol, thioalkyl, sulfate, sulfonyl, sulfinyl, sulfoxide, hydroxyl groups. In aspects of the disclosure the carrier is an amino acid including alanine, glycine, praline, methionine, serine, threonine, asparagine, alanyl-alanyl, prolyl-methionyl, or glycyl-glycyl. A carrier can also include a molecule that targets a compound of the disclosure to a particular tissue or organ.

Compounds of the disclosure can be prepared using reactions and methods generally known to the person of ordinary skill in the art, having regard to that knowledge and the disclosure of this application including the Examples. The reactions are performed in solvent appropriate to the reagents and materials used and suitable for the reactions being effected. It will be understood by those skilled in the art of organic synthesis that the functionality present on the compounds should be consistent with the proposed reaction steps. This will sometimes require modification of the order of the synthetic steps or selection of one particular process scheme over another in order to obtain a desired compound of the disclosure. It will also be recognized that another major consideration in the development of a synthetic route is the selection of the protecting group used for protection of the reactive functional groups present in the compounds described in this disclosure. An authoritative account describing the many alternatives to the skilled artisan is Greene and Wuts (Protective Groups In Organic Synthesis, Wiley and Sons, 1991).

A compound of the disclosure of the disclosure may be formulated into a pharmaceutical composition for administration to a subject by appropriate methods known in the art. Pharmaceutical compositions of the present disclosure or fractions thereof comprise suitable pharmaceutically acceptable carriers, excipients, and vehicles selected based on the intended form of administration, and consistent with conventional pharmaceutical practices. Suitable pharmaceutical carriers, excipients, and vehicles are described in the standard text, Remington: The Science and Practice of Pharmacy (21.sup.st Edition. 2005, University of the Sciences in Philadelphia (Editor), Mack Publishing Company), and in The United States Pharmacopeia: The National Formulary (USP 24 NF19) published in 1999. By way of example for oral administration in the form of a capsule or tablet, the active components can be combined with an oral, non-toxic pharmaceutically acceptable inert carrier such as lactose, starch, sucrose, methyl cellulose, magnesium stearate, glucose, calcium sulfate, dicalcium phosphate, mannitol, sorbital, and the like. For oral administration in a liquid form, the chug components may be combined with any oral, non-toxic, pharmaceutically, acceptable inert carrier such as ethanol, glycerol, water, and the like. Suitable binders (e.g., gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof. Compositions as described herein can further comprise wetting or emulsifying agents, or pH buffering agents.

The term "immunogenic composition" as used herein are those which result in specific antibody production or in cellular immunity when injected into a host.

The immunogenic compositions and/or vaccines of the present disclosure may be formulated by any of the methods known in the art. They can be typically prepared as injectables or as formulations for intranasal administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

The active immunogenic ingredients are often mixed with excipients or carriers, which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable, aerosol or nasal formulations is usually in the range of about 0.2 to 5 mg/ml. Similar dosages can be administered to other mucosal surfaces.

In addition, if desired, the vaccines may contain minor amounts of auxiliary substances such as wetting or emulsifying agents, pH buffering agents, and/or other agents, which enhance the effectiveness of the vaccine. Examples of agents which may be effective include, but are not limited to, aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. The effectiveness of the auxiliary substances may be determined by measuring the amount of antibodies (especially IgG, IgM or IgA) directed against the immunogen resulting from administration of the immunogen in vaccines which comprise the adjuvant in question. Additional formulations and modes of administration may also be used.

The immunogenic compositions and/or vaccines of the present disclosure can be administered in a manner compatible with the dosage formulation and in such amount and manner as will be prophylactically and/or therapeutically effective, according to what is known to the art. The quantity to be administered, which is generally in the range of about 1 to 1,000 micrograms of viral surface envelope glycoprotein per dose and/or adjuvant molecule per dose, more generally in the range of about 5 to 500 micrograms of glycoprotein per dose and/or adjuvant molecule per dose, depends on the nature of the antigen and/or adjuvant molecule, subject to be treated, the capacity of the host's immune system to synthesize antibodies, and the degree of protection desired. Precise amounts of the active ingredient required to be administered may depend on the judgment of the physician or veterinarian and may be peculiar to each individual, but such a determination is within the skill of such a practitioner.

The vaccine or immunogenic composition may be given in a single dose; two-dose schedule, for example, two to eight weeks apart; or a multi-dose schedule. A multi-dose schedule is one in which a primary course of vaccination may include 1 to 10 or more separate doses, followed by other doses administered at subsequent time intervals as required to maintain and/or reinforce the immune response (e.g., at 1 to 4 months for a second dose, and if needed, a subsequent dose(s) after several months).

The term "immunogenic fragment" as used herein refers to a fragment of an immunogen that includes one or more epitopes and thus can modulate an immune response or can act as an adjuvant for a co-administered antigen. Such fragments can be identified using any number of epitope mapping techniques, well known in the art (see, e.g., Epitope Mapping Protocols in Methods in Molecular Biology, Vol. 66 (Morris, G. E., Ed., 1996) Humana Press, Totowa, NJ).

Immunogenic fragments can be at least about 2 amino acids in length, more preferably about 5 amino acids in length, and most preferably at least about 10 to about 15 amino acids in length. There is no critical upper limit to the length of the fragment, which can comprise nearly the full-length of the protein sequence or even a fusion protein comprising two or more epitopes.

The term "immunoglobulin" as used herein refers to a class of proteins that exhibit antibody activity and bind to other molecules (e.g., antigens and certain cell-surface receptors) with a high degree of specificity. Immunoglobulins can be divided into five classes: IgM, IgG, IgA, IgD, and IgE. IgG is the most abundant antibody class in the body and assumes a twisted "Y" shape configuration. With the exception of the IgMs, immunoglobulins are composed of four peptide chains that are linked by intrachain and interchain disulfide bonds. IgGs are composed of two polypeptide heavy chains (H chains) and two polypeptide light chains (L chains) that are coupled by non-covalent disulfide bonds.

The term "immunological response" as used herein refers to the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells.

One aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

The term "immunogenic amount" as used herein refers to an amount capable of eliciting the production of antibodies directed against the virus in the host to which the vaccine has been administered.

The term "immunogenic carrier" as used herein refers to a composition enhancing the immunogenicity of the virosomes from any of the viruses discussed herein. Such carriers include, but are not limited to, proteins and polysaccharides, and microspheres formulated using, for example, a biodegradable polymer such as DL-lactide-co-glycolide, liposomes, and bacterial cells and membranes. Protein carriers may be joined to the proteinases, or peptides derived therefrom, to form fusion proteins by recombinant or synthetic techniques or by chemical coupling. Useful carriers and ways of coupling such carriers to polypeptide antigens are known in the art.

The term "immunopotentiator," as used herein, is intended to mean a substance that, when mixed with an immunogen, elicits a greater immune response than the immunogen alone. For example, an immunopotentiator can enhance immunogenicity and provide a superior immune response. An immunopotentiator can act, for example, by enhancing the expression of co-stimulators on macrophages and other antigen-presenting cells.

The terms "subject", "individual", or "patient" as used herein are used interchangeably and refer to an animal preferably a warm-blooded animal such as a mammal. Mammal includes without limitation any members of the Mammalia. A mammal, as a subject or patient in the present disclosure, can be from the family of Primates, Carnivora, Proboscidea, Perissodactyla, Artiodactyla, Rodentia, and Lagomorpha. In a particular embodiment, the mammal is a human. In other embodiments, animals can be treated; the animals can be vertebrates, including both birds and mammals. In aspects of the disclosure, the terms include domestic animals bred for food or as pets, including equines, bovines, sheep, poultry, fish, porcines, canines, felines, and zoo animals, goats, apes (e.g. gorilla or chimpanzee), and rodents such as rats and mice.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "vaccine" as used herein refers to an immunogenic amount of one or more virosomes, fragment(s), or subunit(s) thereof. Such vaccines can include one or more viral surface envelope glycoproteins and portions thereof, and adjuvant molecule and portions thereof on the surfaces of the virosomes, or in combination with another protein or other immunogen, such as one or more additional virus components naturally associated with viral particles or an epitopic peptide derived therefrom.

A saponin preparation isolated from the South American tree *Quillaja saponaria* Molina was first described by Dalsgaard et al. in 1974 ("Saponin adjuvants", Archiv. fur die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina, that induces CD8+ cytotoxic T cells (CTLs), Th1 cells and a predominant IgG2a antibody response.

Saponins of the disclosure can be used at amounts between 1 and 100 μg per human dose of the adjuvant composition, at a level of about 50 ug, for example between 40 to 60 μg, suitably between 45 to 55 μg or between 49 and 51 μg or 50 μg. In some embodiments, a human dose of the adjuvant composition can comprise QS21 at a level of about 25 μg, for example between 20 to 30 μg, suitably between 21 to 29 μg or between 22 to 28 μg or between 28 and 27 μg or between 24 and 26 μg, or 25 μg.

When the adjuvant is to be combined with a liquid form of an antigenic composition, the adjuvant composition will be in a human dose suitable volume which is approximately half of the intended final volume of the human dose. For example a 500 μl volume of adjuvant for an intended final human dose of 1 μl, or a 250 μl volume for an intended final human dose of 0.5 ml. The adjuvant composition is diluted when combined with the antigen composition to provide the final human dose of vaccine. The final volume of such dose will of course vary dependent on the initial volume of the adjuvant composition and the volume of antigen composition added to the adjuvant composition. In an alternative embodiment, the aqueous adjuvant is used to reconstitute a lyophilized antigen composition. In this embodiment, the human dose suitable volume of the adjuvant composition is approximately equal to the final volume of the human dose. The liquid adjuvant composition is added to the vial containing the lyophilized antigen composition and used to reconstitute the lyophilized antigen composition.

Abbreviations

IgG, immunoglobulin G; Th, T helper cells; CTL, cytotoxic T lymphocyte; rha, rhamnose; xyl, xylose; OVA, ovalbumin; NMM, N-methylmorpholine; HOBt, hydroxybenzotriazole; EDC HCl, 1-ethyl-3-(3-dimethylaminopropyl) carbodiimide; DCM, dichloromethane; MeCN, acetonitrile; THF, tetrahy-drofuran; rHagB, recombinant hemagglutinin B; s.c., subcutaneous; ESI-TOF, electrospray ionization time-of-flight mass spectrometry; ELISA, enzyme-linked immunosorbent assay;

DISCUSSION

The advantage of having structurally-defined new saponin adjuvants from natural sources other than *Quillaja saponaria* Molina tree bark is multifold. First, the plant *Momordica cochinchinensis* Spreng is a perennial vine, and easy to grow, which circumvents the drawback of limited supplies of QS saponins. Second, the abundance of saponins in the MS seeds (FIG. 1) is high, and their isolation is more efficient and thus cost-effective than QS saponins. *M. cochinchinensis* Spreng grows mainly in China and Southeast Asia. The seeds (*Mubiezi*) have been utilized in China as a traditional Chinese medicine for more than 1000 years for the treatment of ulcer, mastitis, carbuncle, anal fistula, hemorrhoids, eczema, and neurodermatitis. Recently, an extract from *M. cochinchinensis* seeds was evaluated for its adjuvant effect and safety in an experimental swine vaccine against foot-and-mouth disease (FMD). The MS saponins showed synergistic effect with oil emulsion in boosting antigen-specific IgG in guinea pigs. However, in a comparison of adjuvant activities against other adjuvants, i.e., Freund's adjuvant, Quil A (QA), and propolis in chickens immunized with the antigen F4 fimbriae, the MS saponins showed lower capacity than Freund's adjuvant and QA in boosting IgG response both in serum and egg yolk. These results are consistent with observations that without a fatty side chain, the de-acylated QS-17/18 only showed humoral immunity.

Figure 3:
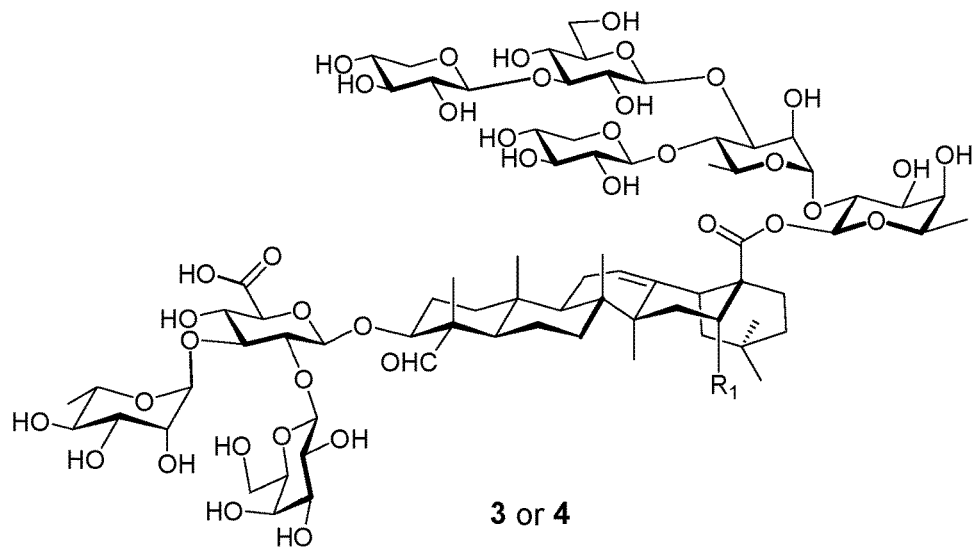
FIG. 3 illustrates the chemical derivatization natural saponins MS I and II to prepare A and related compounds.
Figure 3:
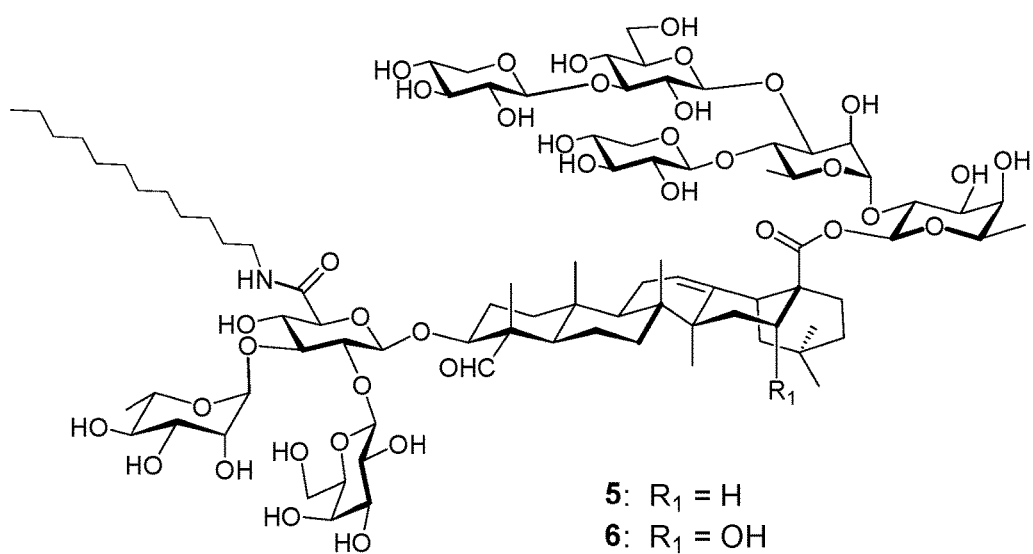
Figure 4:
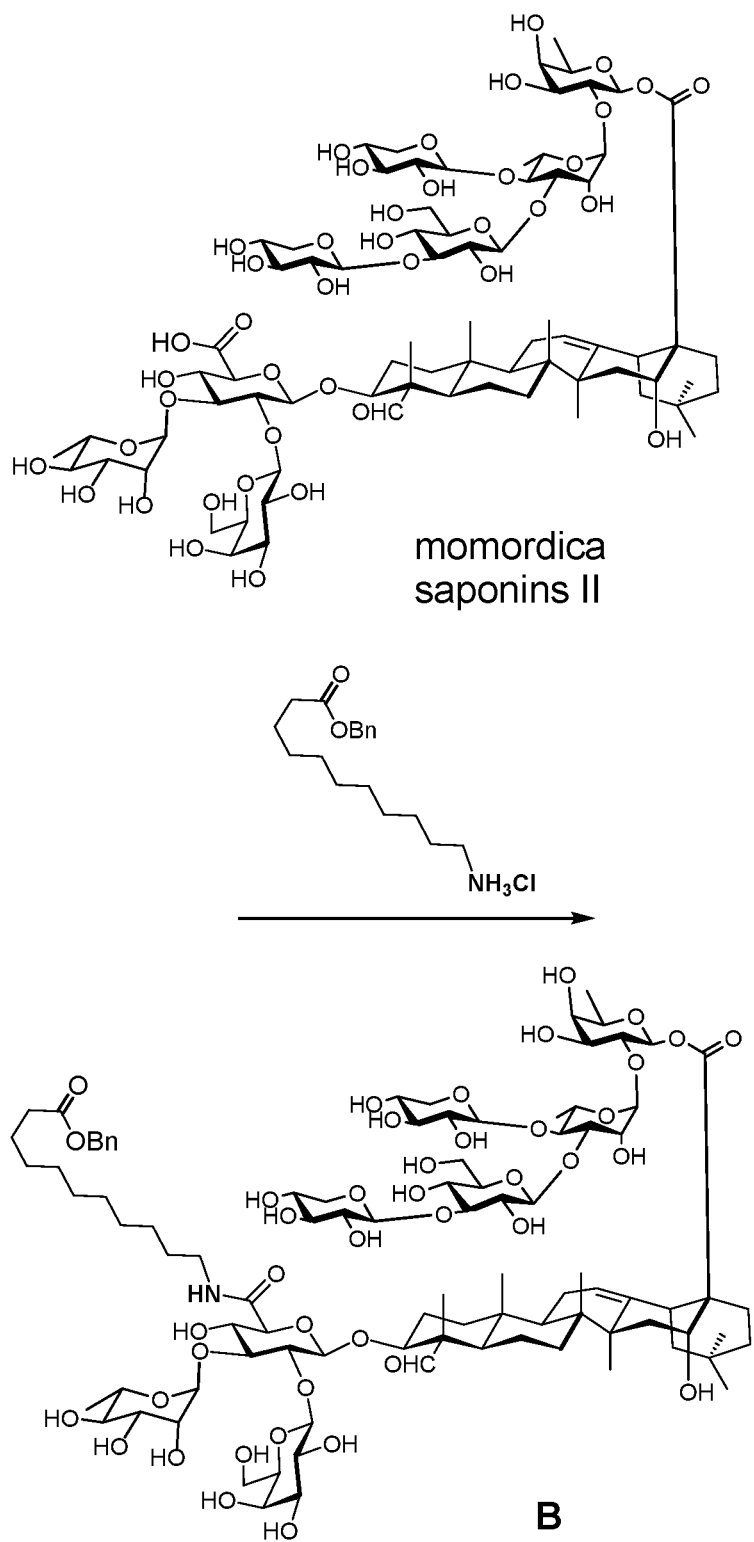
FIG. 4 illustrates chemical derivatization of natural saponins MS I and II to prepare B and related compounds.

Two natural MS saponins from *Momordica cochinchinensis* (Lour.) Spreng seeds were isolated by using the published procedure and as outlined in FIG. 11. The two MS derivatives, i.e., 5 and 6, from natural saponins 3 and 4, respectively, were then synthesized by using a routine one-step amide-formation reaction (FIG. 3).

Figure 7:
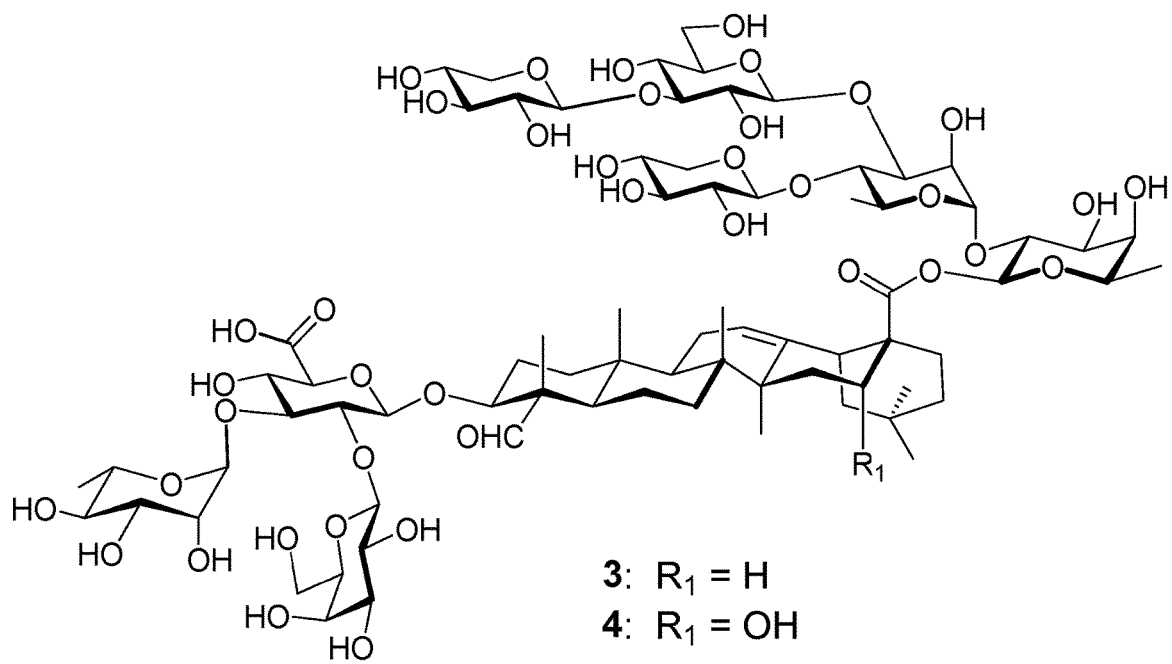
FIG. 7 illustrates structures 3, 4, 5, and 6.
Figure 7:
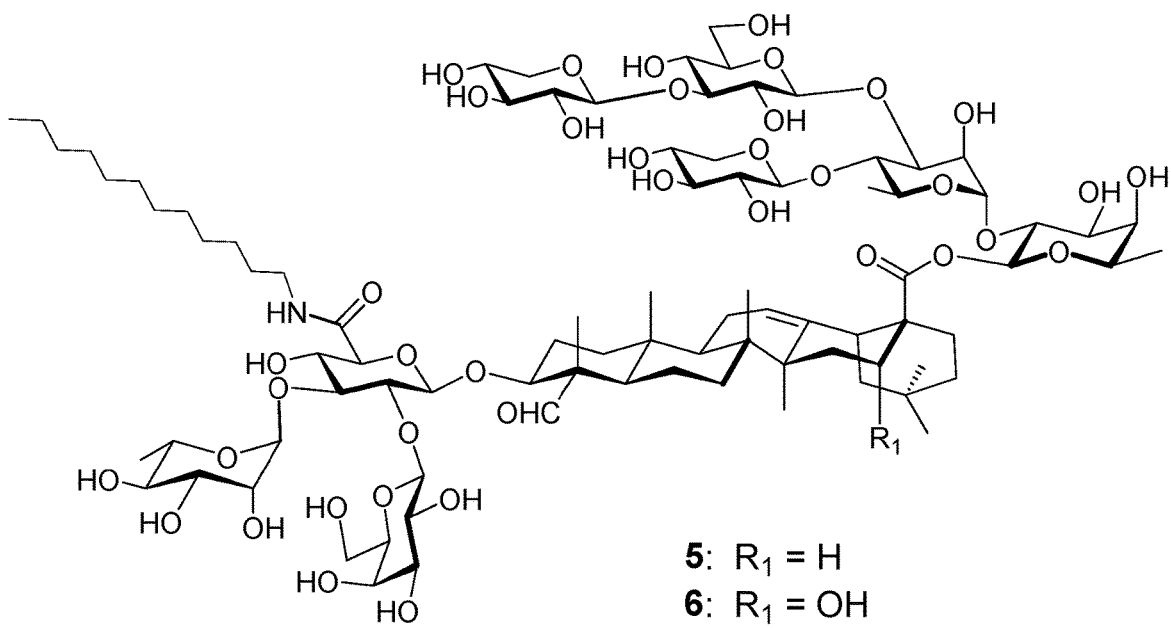

With pure natural saponins 3 and 4, and their derivatives 5 and 6 (FIG. 7) available, their ability to potentiate antibody responses to chicken egg ovalbumin (OVA) was evaluated. The known saponin adjuvant GPI-0100 was used as a positive control. Thus, groups of female BALB/c mice (8-10 weeks of age, six per group) were immunized by the subcutaneous route (s.c.) with OVA (20 µg) alone or with GPI-0100, saponins 3-6 at 100 µg dose on days 0, 14 and 28. Mice were weighed and serum samples were collected prior to each immunization and at 6 weeks after the initial immunization. The levels of serum IgG antibody activity to OVA were determined by enzyme-linked immunosorbent assay (ELISA), as shown in FIGS. 6A-6C, 9A-9C, and Table 1.

A serum IgG response was detected in all groups by week 2 after the initial immunization. A significant increase was seen in the level of IgG anti-OVA antibody activity in mice receiving OVA+adjuvant following the second immunization, and the magnitude of the response continued to increase following the third immunization (Table 1). As positive control, GPI-0100 potentiated significantly higher IgG responses to OVA than seen with antigen alone at weeks 2 ($P<0.05$), 4 ($P<0.001$), and 6 ($P<0.001$). Similar to GPI-0100, adjuvant VSA-1 (5, derivative of natural MS I (3)) showed significantly higher anti-OVA IgG responses than mice received antigen alone at weeks 2 ($P<0.01$), 4 ($P<0.001$), and 6 ($P<0.01$), and mice received OVA+3 at weeks 2 ($P<0.001$), 4 ($P<0.001$), and 6 ($P<0.01$). Saponin 3 did not show significant difference in IgG responses from the OVA group. Saponin 4 showed significant difference in IgG responses from the OVA group at weeks 2 ($P<0.01$) and 4 ($P<0.001$) but not at week 6. Adjuvant 6 (derivative of natural MS II (4)) showed significantly higher anti-OVA IgG responses than the OVA group at weeks 4 ($P<0.001$) and 6 ($P<0.05$), but did not show significant difference from its parent compound 4 until week 6 ($P<0.05$). No sign of toxicity was observed in any of the mice based on weight monitoring.

The IgG subclass antibody responses induced by different adjuvants were then analyzed. All adjuvants showed significantly higher IgG1 responses than the OVA group of mice at weeks 2 and 4 (Table 1). However, at week 6, only GPI-0100 ($P<0.001$), 5 ($P<0.05$), and 6 ($P<0.01$) showed significantly higher IgG1 responses than the OVA group. In IgG2a assessments (FIG. 6B), there was no significant difference among the groups at week 2, but GPI-0100 ($P<0.001$) and VSA-1 (5) ($P<0.001$) induced significantly higher IgG2a than the OVA group at week 4. At week 6, GPI-0100 ($P<0.05$) and VSA-1 (5) ($P<0.01$) still showed significantly higher titers of IgG2a than seen in mice with OVA alone, or with adjuvants 3 ($P<0.01$), 4 ($P<0.01$), or 6 ($P<0.01$), but no significant difference between the groups of GPI-0100 and VSA-1.

Analysis of the IgG2a/IgG1 ratio of the anti-OVA responses at week 6 revealed that adjuvant 5 had a significantly higher ratio ($P<0.01$) than OVA alone, or OVA with 3, 4, or 6, but no significant difference from GPI-0100 (FIG. 8). The negligible IgG2a responses from the groups without an adjuvant or with adjuvant 3, 4, or 6 suggest a Th2-biased immune response was selectively induced in these groups. Since GPI-0100 is known for its capability in potentiating a mixed Th1/Th2 response with CTL production, similar IgG2a/IgG1 distributions between GPI-0100 (0.194, Table 1, entry 2)) and adjuvant 5 (0.312, Table 1, entry 5) suggest that these two adjuvants could have a similar activity profile.

TABLE 1

| Serum IgG subclass anti-OVA activity at week 6[a] | | | | |
|---|---|---|---|---|
| Entry | adjuvant | IgG1 (mg/mL) | IgG2a (mg/mL) | IgG2a/IgG1 |
| 1 | none | 113 ± 37 | 0.1 | 0.001** |
| 2 | GPI-0100 | 1,047 ± 292 | 166 ± 50 | 0.194 ± 0.060 (ns) |
| 3 | 3 | 233 ± 74 | 0.2 | <0.001** |
| 4 | 4 | 262 ± 37 | 0.1 | <0.001** |
| 5 | 5 | 713 ± 293 | 208 ± 81 | 0.312 ± 0.126 |
| 6 | 6 | 869 ± 334 | 1 | <0.001** |

[a]Values are expressed as mean ± SEM. Statistical significance compared with OVA+5, *$P < 0.05$, $P < 0.01$, *$P < 0.001$.

Figure 8A:
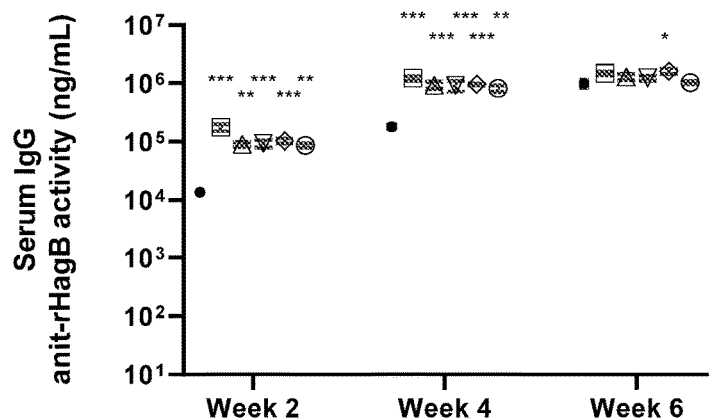
FIG. 8 illustrates graphs illustrating a serum IgG, IgG1, and IgG2a anti-rHagB responses in mice immunized by the subcutaneous route with rHagB alone, rHagB with GPI-0100, and rHagB with the natural saponins 3 or 4, or their respective derivative 5 or 6.
Figure 8B:
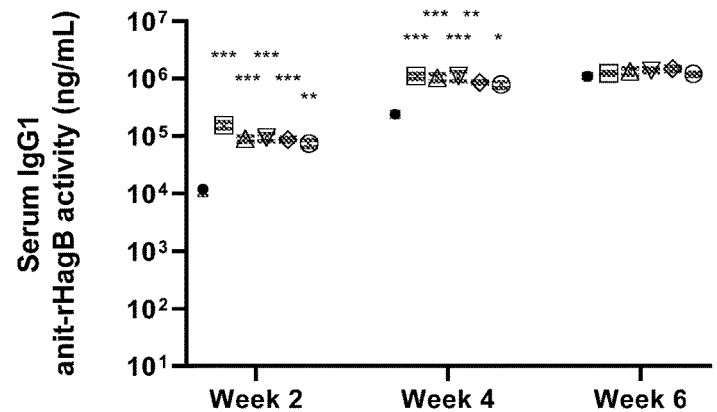
Figure 8C:
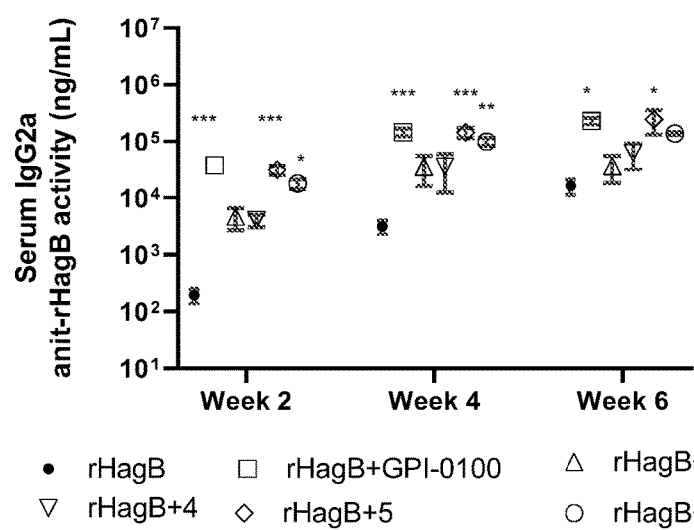

As a comparison, adjuvants 3-6 in augmenting immune responses to rHagB, a recombinant, non-fimbrial adhesion hemagglutinin B from *Porphyromonas gingivalis* were also evaluated, as shown in FIGS. 8A-8C. The antigen is an etiologic agent of periodontal disease, and the effectiveness has been demonstrated of rHagB inducing a protective immune response against *P. gingivalis*-induced alveolar bone loss in an experimental animal model. By using the same procedure, the results with rHagB antigen (at a 35 µg dose) were similar to those with OVA antigen, and the IgG, IgG1 and IgG2a data are summarized in FIGS. 8A-8C.

The antigen rHagB stimulated a strong humoral immune response. Although IgG and IgG1 titers in the group without adjuvant were lower than the groups with an adjuvant at weeks 2 and 4, the difference became insignificant at week 6 (except for IgG of the group with 5 ($P<0.05$)) (FIGS. 8A and 8B, respectively). In terms of IgG2a (FIG. 8C), mice with GPI-0100 or 5 showed significantly higher activity than the group with rHagB alone at weeks 2 ($P<0.001$), 4 ($P<0.001$), and 6 ($P<0.05$), which is consistent with what has been observed with the OVA antigen. Mice with 6 also showed significantly higher IgG2a titers than the rHagB control group at weeks 2 ($P<0.05$) and 4 ($P<0.01$) but not at week 6.

These results showed that by incorporating a simple and chemically stable fatty side chain to natural *Momordica* saponin I (3), the new derivative (5) not only retains and enhances the IgG1 immunity of 3 but also modulates its adjuvant activity profile by inducing a significant IgG2a immune response. However, when the same strategy was applied to *Momordica* saponins II (4), no significant increase of IgG2a was observed. While not wishing to be bound by any one theory, given that the only structural difference between the two MS derivatives is in the triterpenoid core, i.e., gypsogenin ($R_1=H$) versus quillaic acid ($R_1=OH$), it appears that the structure of the triterpenoid core instead of the hydrophile-lipophile balance of the saponin structure plays an important role in affecting adjuvant activity of derivatives 5 and 6.

Acute toxicity of adjuvant VSA-1 (5) was evaluated by using the same procedure for GPI-0100. Thus, female BALB/c mice, 10 weeks of age, were given a s.c. injection of an adjuvant in 0.1 mL of PBS on the back of the neck with the doses shown in Table 2.

TABLE 2

Acute toxicity comparison of 5, Quil A, and GPI-0100[a]

| Dose (mg) | VSA-1 (5) | GPI-0100[b] | Quil-A |
|---|---|---|---|
| Controls | 5/5 | 5/5 | 5/5 |
| 100 | 5/5 | 5/5 | 0/5 |
| 200 | 5/5 | 5/5 | 0/5 |
| 500 | 5/5 | 5/5 | |
| 1000 | 5/5 | 5/5 | |
| 2000 | 5/5 | 4/5 | |
| 5000 | 0/5 | 0/5 | |

[a]Results are expressed as the number of surviving mice per group of 5 mice 5 days post injection
[b]literature results, female BALB/c mice of 16 weeks of age.

[b]literature results, female BALB/c mice of 16 weeks of age.

All of the mice in the groups treated with 5 (5000 µg) and Quil-A, died within five days post injection. The survival mice all had healthy looking fur and appeared to be behaving normally. None of the survival mice seemed lethargic in any way by day 7 and no lesion formation was observed on any of the mice. The data in Table 2 showed that the acute toxicity of 5 was similar to that of GPI-0100, but much lower than that of Quil A. Momordica saponins I and II have been derivatized by coupling them with dodecylamine at $C_3$ glucuronic acid site. The obtained derivatives show significantly different immunostimulant activity profiles from their natural parent saponins. In particular, adjuvant VSA-1 (5), the derivative of Momordica saponin I (3), induces a significantly higher IgG2a response than the corresponding natural product. Its IgG1 and IgG2a productions are similar to that of GPI-0100, suggesting a potential mixed Th1/Th2 immune response against the specific antigens, different from the Th2 immunity induced by the natural saponins. Toxicity evaluations show that VSA-1 (5) has a toxicity profile similar to that of GPI-0100 and is much less toxic than the widely used natural saponin mixture Quil A. These results proved derivatizing Momordica saponins is a viable way for easy access to structurally defined saponin immunostimulants with low toxicity for a mixed Th1/Th2 immune responses. Given the fact that MS saponins are readily available and easy to isolate, it will be useful for large-scale preparation of MS derivatives for potential preclinical studies and clinical applications.

Figure 16:
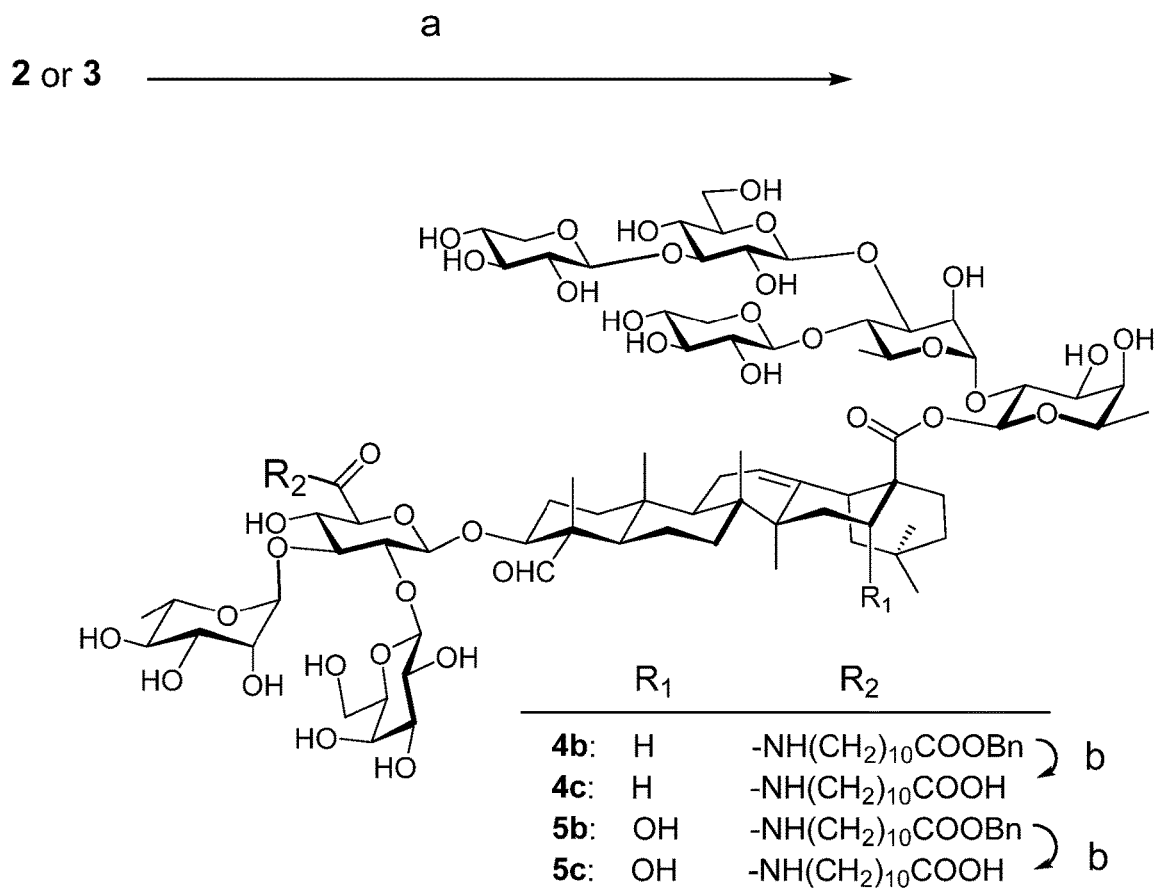
FIG. 16 illustrates Scheme 1 for derivatizing *Momordica* saponins.

Two MS I (2) derivatives 4b and 4c (Scheme 1, FIG. 16) were prepared. The side chain of 4b has a terminal ester group while 4c has the same side chain as QS-21 analog 7. Similarly, two corresponding MS II (3) derivatives 5b and 5c were also prepared. The two natural MS saponins (2 and 3) were isolated from commercially available and inexpensive MC seeds by using a published procedure. Derivatives 4b and 5b We then synthesized from the respective natural saponins and the side chain by using a routine amide-formation method. Hydrogenolysis of 4b and 5b led to 4c and 5c, respectively, in high yields. Under the hydrogenolysis conditions, the C12 alkene moiety in the quillaic acid core remained intact.

Their ability to potentiate antibody responses to chicken egg ovalbumin (OVA) was then evaluated. The known saponin adjuvant GPI-0100 was one of the positive controls. Also used was the recently reported MS derivative VSA-1 (4a) as the other positive control. Its high IgG1/IgG2a production and low toxicity are similar to that of GPI-0100.

Thus, groups of female BALB/c mice (8-10 weeks of age, six per group) were immunized by the subcutaneous route (s.c.) with OVA (20 µg) alone or with GPI-0100, or a MS saponin derivative at 100 µg dose on days 0, 14 and 28. Mice were weighed and serum samples were collected prior to each immunization and at 2 weeks following the last immunization. The levels of serum antibody activity to OVA were determined by enzyme-linked immunosorbent assay (ELISA).

Figure 9A:
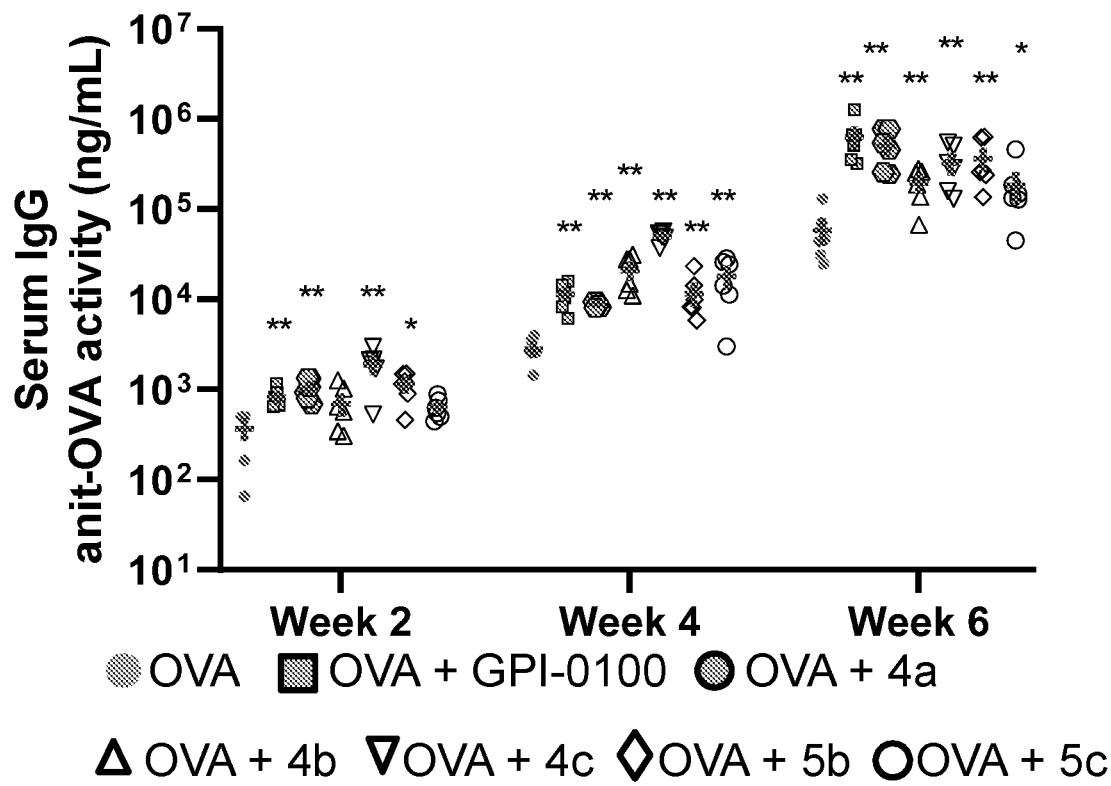
FIGS. 9A-9D illustrate serum IgG, IgG1, and IgG2a anti-OVA response in mice immunized by the s.c. route with OVA alone or with GPI-0100 or a MS derivative. Mice were immunized on days 0, 14 and 28. Serum samples were collected prior to each immunization and at 6 weeks after the initial immunization. Values are expressed as mean±SEM. Statistical significance in antibody responses was evaluated by t tests (with unpaired, nonparametric and Mann-Whiteny test). *P<0.05 and **P<0.01 compared with mice immunized with OVA alone.
Figure 9B:
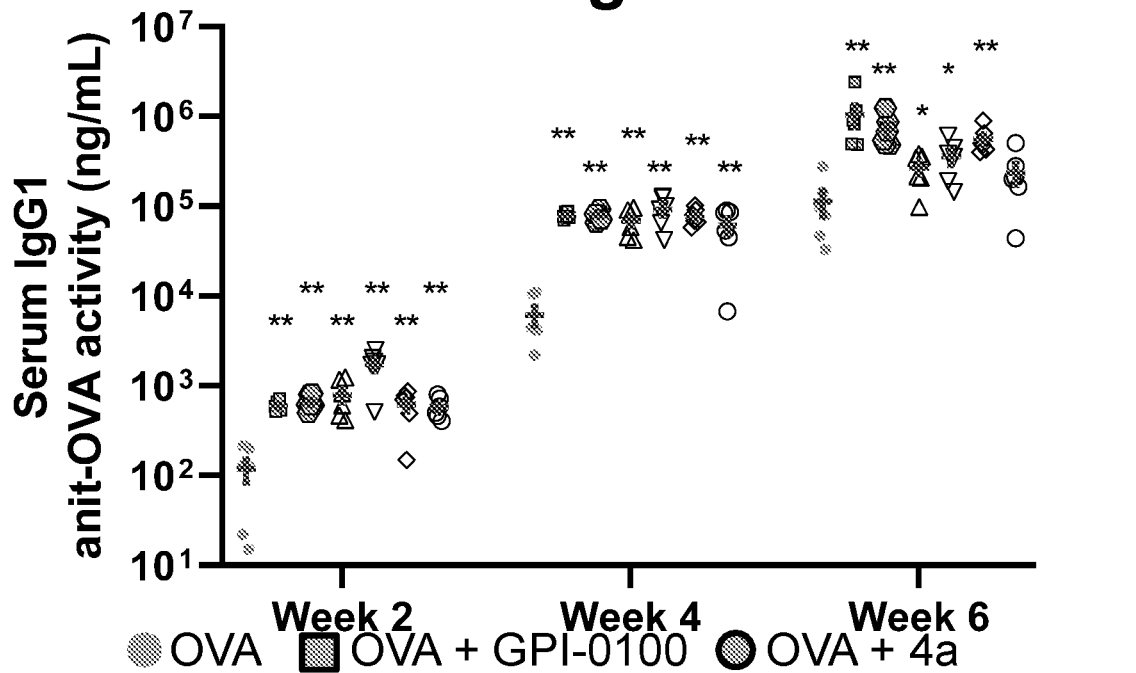
Figure 9C:
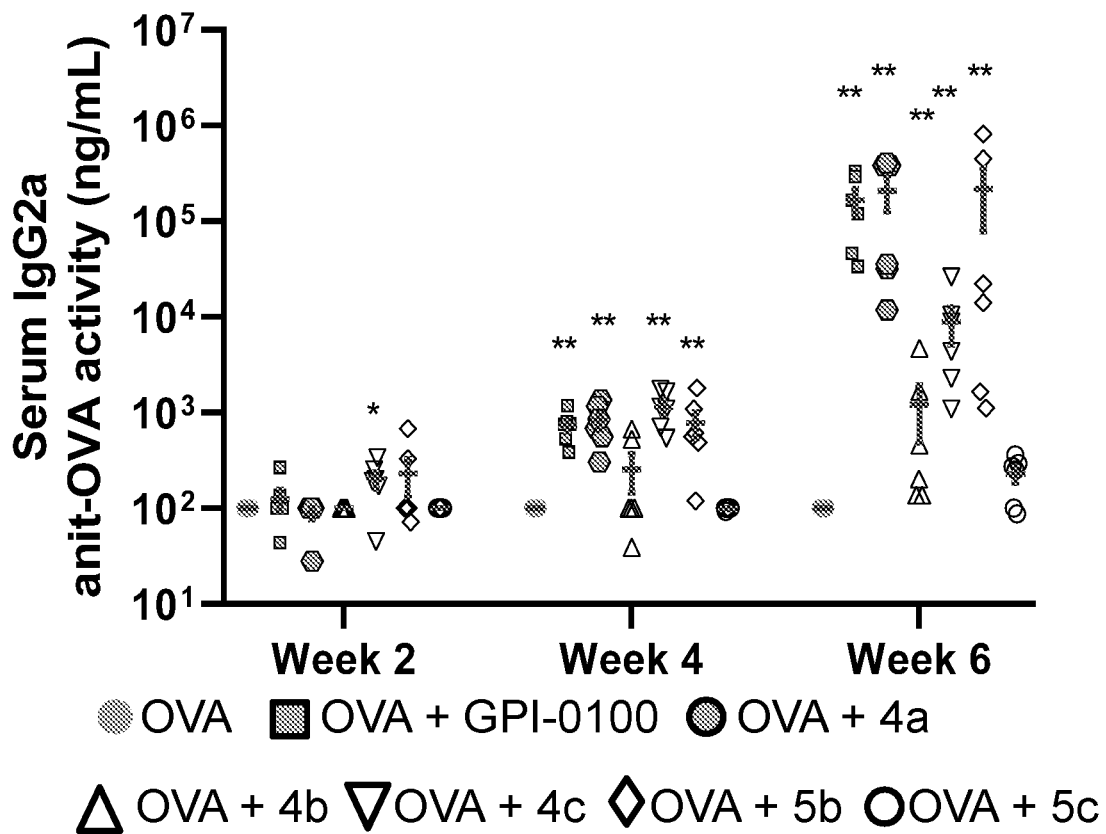
Figure 9D:
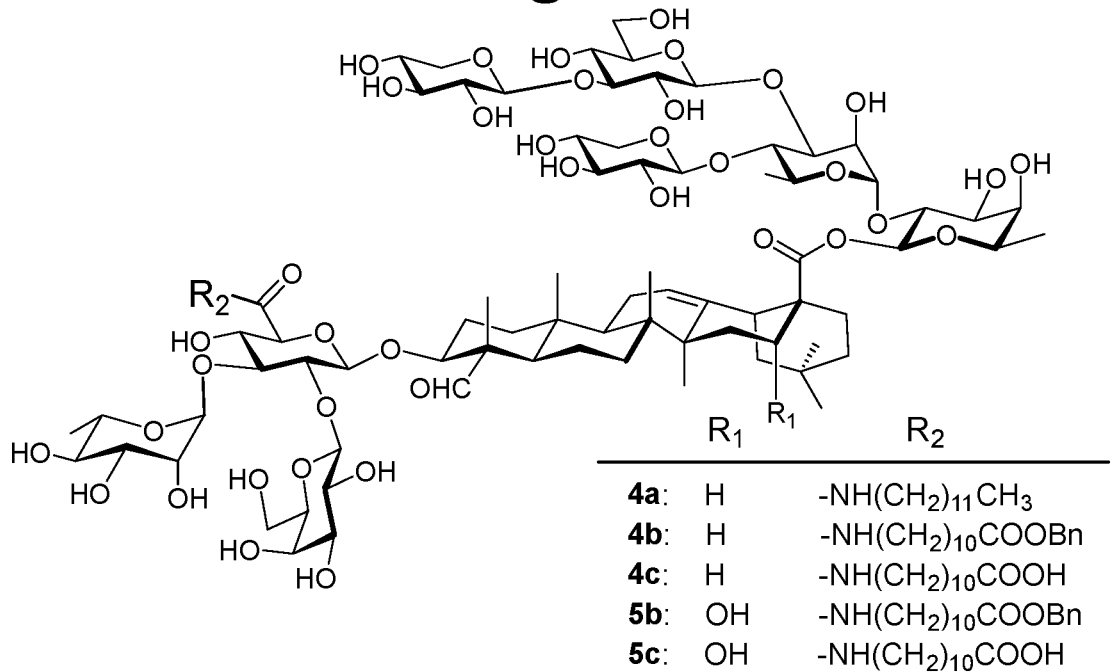

All groups of mice had a serum anti-OVA IgG response by week 2 after the initial immunization, and the level of IgG titers continued to increase at weeks 4 and 6 (FIG. 9A). At weeks 4 and 6, all the adjuvant groups showed significantly higher IgG activity than the OVA control group without an adjuvant. The same trend appeared in anti-OVA IgG1 activities (FIG. 9B), but at week 6, the OVA+5c group did not show statistical difference from the OVA control group. In terms of IgG2a activity (FIG. 9C), the OVA control group remained the same activity over time while other groups with an adjuvant (except the OVA+5c group) showed steady increase of IgG2a titers at weeks 4 and 6. Adjuvant VSA-2 (5b) potentiated a significantly higher IgG2a activity than the OVA group (P<0.01), OVA+4b (P<0.05), and OVA+5c group (P<0.01) at week 6, but showed no significant difference from the positive control groups and the OVA+4c group.

Figure 17:
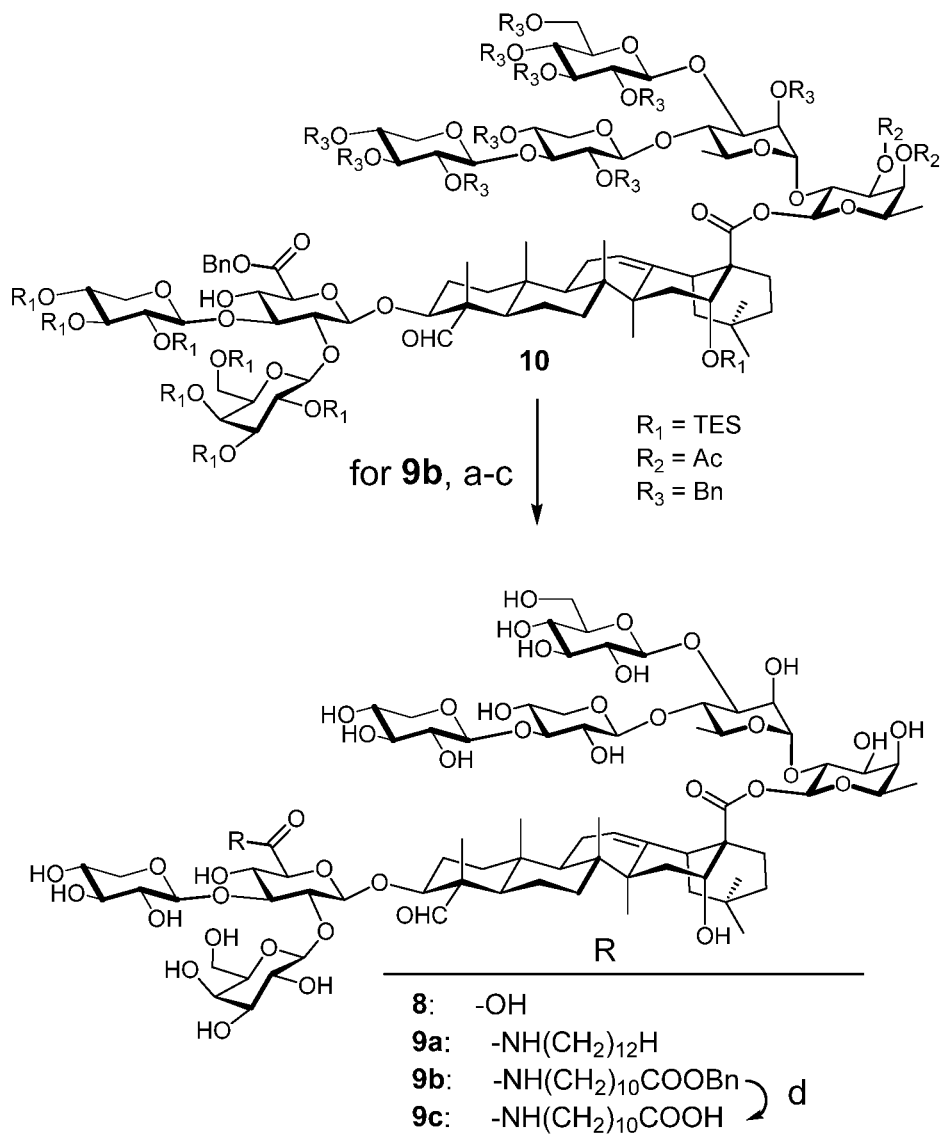
FIG. 17 illustrates Scheme 2 for the synthesis of QS saponin analogs with different side chains.

Given the structural similarity between MS I/II (FIG. 1) and de-acylated QS-17/18 (8) (Scheme 2, FIG. 17), the QS-17/18 derivatives similar to 5b/5c were synthesized in order to see with the same side chain how the slight difference in C3 and C28 oligosaccharide domains would affect adjuvanticity. QS-17/18 derivative 9a was previously synthesized and evaluated, and by using the same synthetic route, new derivatives 9b and 9c were prepared. Thus, fully protected intermediate 10 first underwent debenzylation to remove all the benzyl protecting groups. The carboxyl group at C3 glucuronic acid was exposed. Under the hydrogenolysis conditions, all the triethylsilyl groups were removed as well. Subsequent amide-bond formation reaction installed the side chain as in the synthesis of 4b and 5b. After removal of the two acetyl groups on the fucosyl unit at C28 position under basic conditions, adjuvant candidate 9b was obtained. Debenzylation of 9b led to adjuvant candidate 9c.

The capacities 9b and 9c to potentiate antigen-specific antibody activity were compared with those of 5b and 5c. An rHagB antigen (recombinant and non-fimbrial adhesion hemagglutinin B from Porphyromonas gingivalis) was used. In earlier studies it showed effectiveness in inducing protective immunity against P. gingivalis-induced alveolar bone loss. Groups of female BALB/c mice (8-10 weeks of age, six per group) were immunized by the subcutaneous route (s.c.) with rHagB (35 µg) alone or with GPI-0100, a saponin adjuvant at 100 µg dose on days 0, 14 and 28. The same immunization and ELISA evaluation procedure as with OVA antigen were used.

Figure 10A:
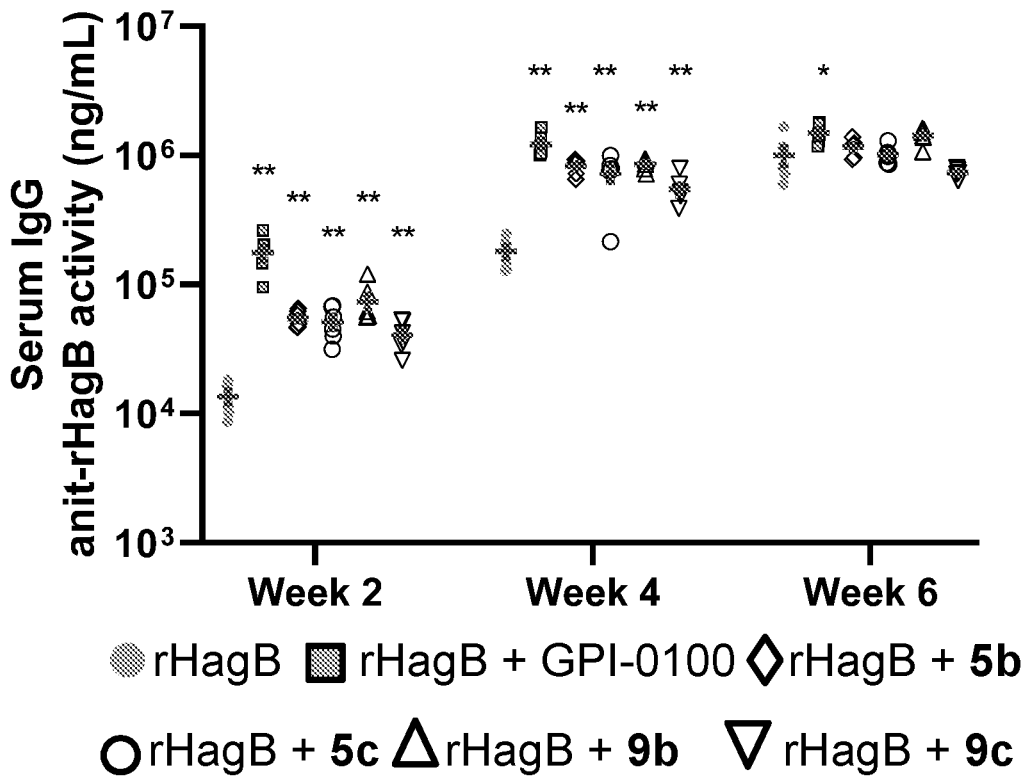
FIGS. 10A-10D illustrate serum IgG, IgG1, and IgG2a anti-rHagB response in mice immunized by the s.c. route with rHagB alone or with GPI-0100 or a saponin adjuvant. Mice were immunized on days 0, 14 and 28. Serum samples were collected prior to each immunization and at 6 weeks after the initial immunization. Values are expressed as mean±SEM. Statistical significance in IgG, IgG1, and IgG2a antibody responses was evaluated by t tests (with unpaired, nonparametric and Mann-Whiteny test). *P<0.05, and **P<0.01 compared with mice immunized with rHagB alone, #P<0.05, compared between the indicated groups.
Figure 10B:
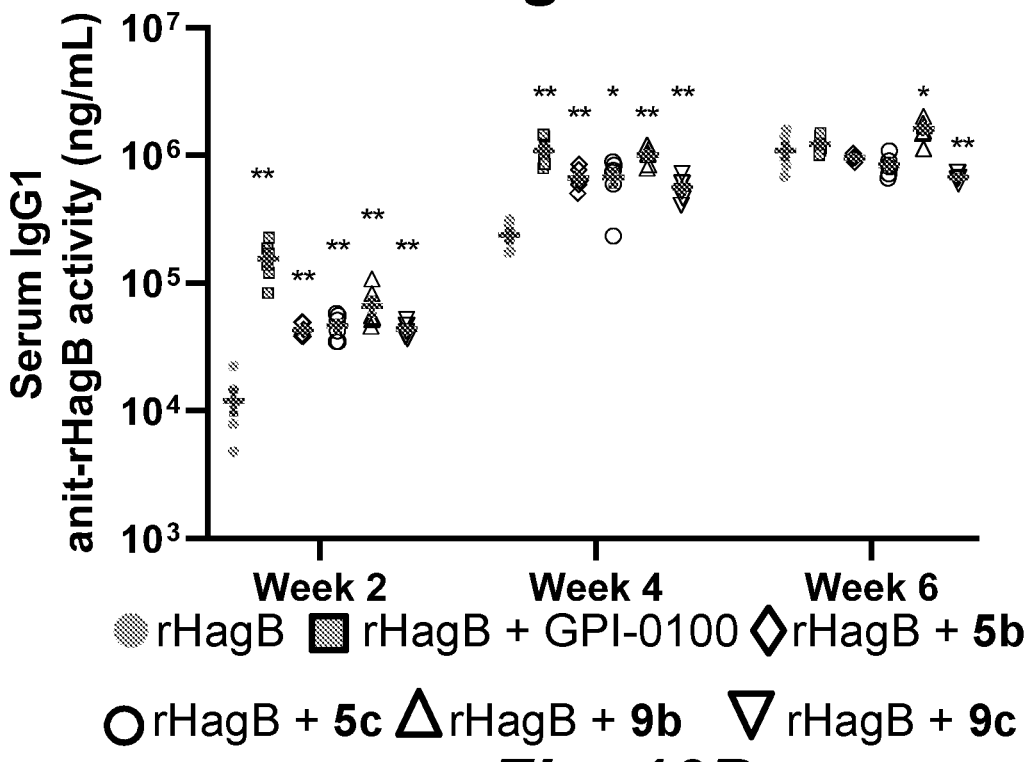
Figure 10C:
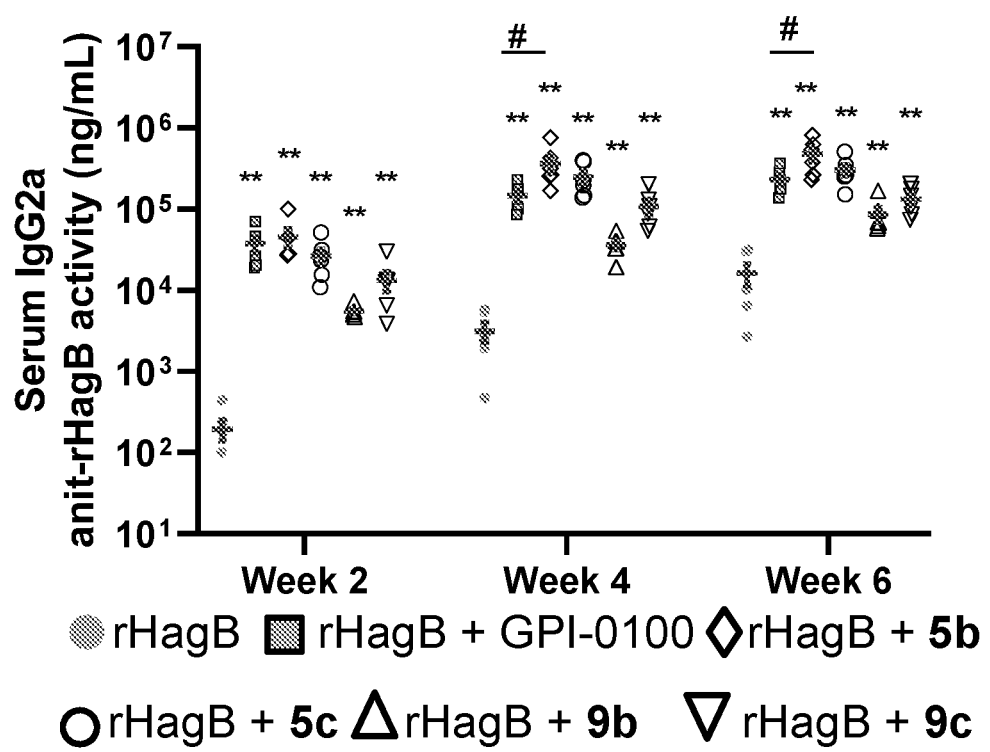
Figure 10D:
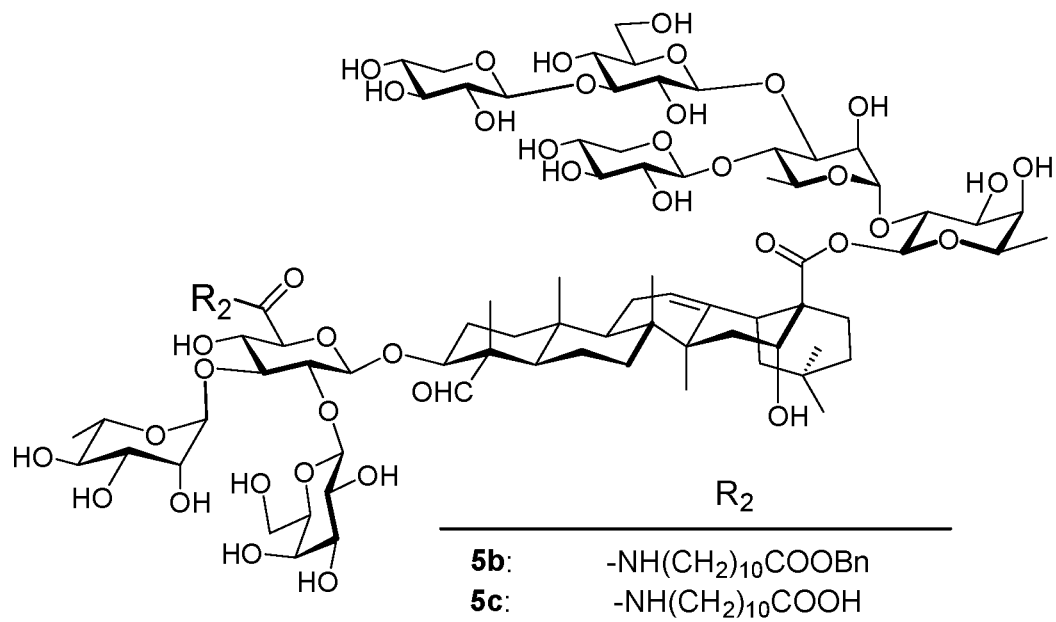
Figure 10D:
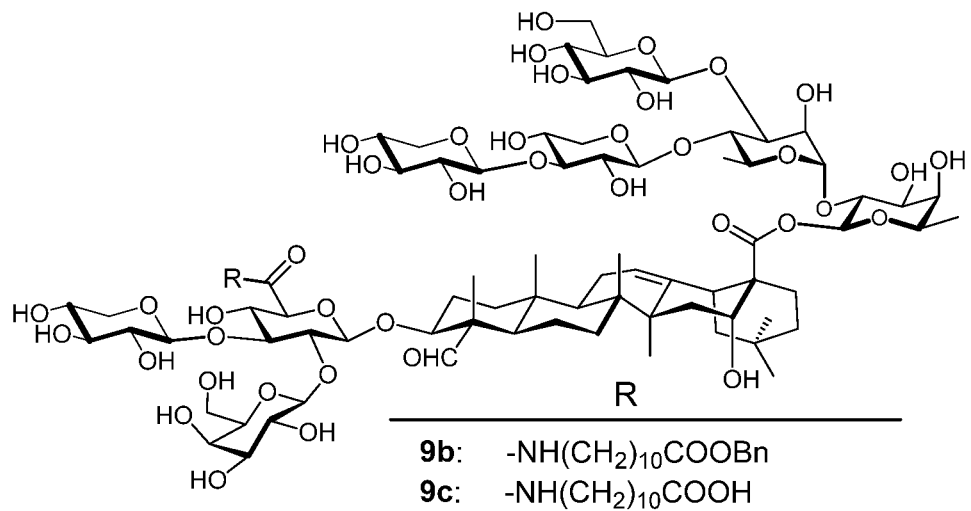

All groups of mice showed a serum anti-rHagB IgG, IgG1, and IgG2a response by week 2 after the initial immunization, and the level of the antibody titers continued to grow at weeks 4 and 6 (FIGS. 10A-10C). At weeks 2 and 4, all groups showed significantly higher IgG titers than the rHagB control group without an adjuvant, but at week 6, only the GPI-0100 group showed statistical difference from the rHagB group. The IgG1 response had a similar trend as seen in IgG (FIG. 10B), but at week 6, the OVA+9a and OVA+9b groups showed statistical difference from the rHagB group. For IgG2a response, all groups showed significantly higher activity than the rHagB control group at weeks 2, 4, and 6 (FIG. 10C).

VSA-2 (5b) potentiated higher IgG2a than the positive control GPI-0100 at week 4 (P <0.05) and week 6 (P<0.05). VSA-2 (5b) also showed higher IgG2a activity than QS-17/18 derivative 9b at week 2 (P<0.01), week 4 (P<0.01), and week 6 (P<0.01), and 9c at week 2 (P<0.05), week 4 (P<0.01), and week 6 (P<0.01). Different from with OVA antigen (FIG. 10C), VSA-2 (5b) did not show significant difference from 5c in potentiating IgG2a response.

Figure 18:
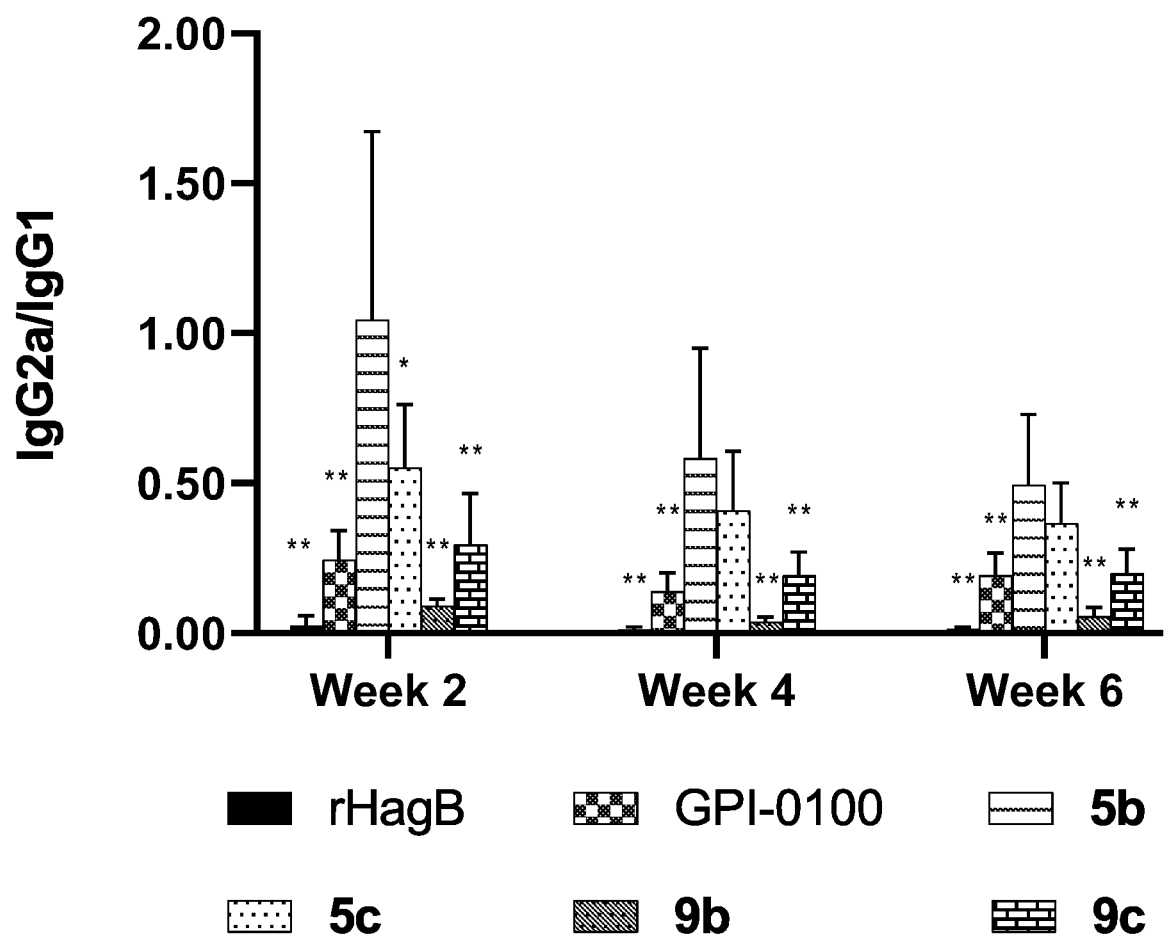
FIG. 18 illustrates the ratio of serum anti-rHagB IgG2a and IgG1 activity (IgG2a/IgG1). Values are expressed as mean #SD. Statistical significance compared with rHagB+ VSA-2 (5b), Statistical significance was evaluated by t tests (with unpaired, nonparametric and Mann-Whiteny test). *P<0.05, **P<0.01.

Since production of IgG1 or IgG2a in mice is enhanced by the respective Th2 or Th1 cytokines, their relative amount can be used as a tentative indication of involvement of Th2 and Th1 immunity potentiated by the adjuvant. With rHagB antigen, VSA-2 (5b) showed a significantly higher IgG2a/IgG1 ratio than other groups (except 5c) at weeks 2, 4, and 6 (FIG. 18). These results suggest that 5b (and 5c) could be capable of boosting Th1 immunity more than GPI-0100 could, which would be valuable when a strong Th1 immunity is desired.

Immunological evaluations of the semisynthetic MS derivatives and synthetic QS analogs revealed that with different protein antigens (i.e., OVA or rHagB), VSA-2 (5b) showed a comparable or higher IgG2a/IgG1 ratio than GPI-0100 with a similar overall IgG production. With OVA antigen, MS derivative 4a enhanced IgG2a production significantly higher than 5a. 4a and 5b also show similar IgG2a productions (no significant difference, FIG. 10C). The only difference between 5a and 5b is their side chain, suggesting that the structure of the side chain affects the antibody activity profile of the induced immunological response. Moreover, with a different side chain, derivatives 5b and 5c also showed different antibody activities when they were combined with the OVA antigen but similar activities when with the rHagB antigen. With the same side chain, saponins 4b, 5b, and 9b, having different core structures, showed different antibody induction stimulation activities. The two saponins, 4b and 5b, only differ in their respective triterpenoid core, with 5b having an extra $C_{16}$ OH (quillaic acid core) compared with 4b's gypsogenin core. Saponins 5b and 9b have the identical triterpenoid core (i.e., quillaic acid) and side chain, but they slightly differ at the C3 and C28 oligosaccharide domains. All these saponins have similar hydrophile-lipophile balance (HLB) and they showed similar overall IgG activities. However, their capability of potentiating IgG2a production differs significantly, which indicates that the specific structure of a saponin, i.e., the structural details of the side chain, triterpenoid core, and oligosaccharide domains, affects the details of an immune response.

A number of MS- and QS-saponin-based vaccine adjuvant candidates have been prepared. The MS derivatives were prepared by incorporating a terminal-functionalized side chain into the C3 glucuronic acid unit of the natural saponins MS I and II through amide formation reaction; and the QS analogs were prepared via multi-step organic synthesis. These unnatural saponins showed significantly different immunostimulant activity profiles, suggesting that the structure of side chain, triterpenoid core, and oligosaccharide domain together orchestrate each saponin's characteristic potentiation of immune responses.

Among the various adjuvant candidates, VSA-2 (5b), a derivative of MS II, constantly enhanced IgG2a production when it was co-delivered with either OVA or rHagB antigen. With antigen rHagB, it induced a significantly higher IgG2a response than the positive control GPI-0100, a well-studied semisynthetic saponin adjuvant derived from QS saponins and known for its ability to induce a balanced Th1/Th2 immunity. The results of the disclosure confirm that *Momordica* saponins are a viable natural source of saponins useful for the preparation of unnatural saponin adjuvants with different adjuvant activities through simple chemical derivatization, and identify VSA-2 (5b) as a useful MS-based immunostimulant (in addition to known VSA-1 (4a)), and particularly useful for its distinctive ability to potentiate an IgG2a response.

Compounds of the present disclosure and pharmaceutical compositions can, therefore, be used in combination of one or more other therapeutic agents for treating viral infection and other diseases. For example, compounds of the present disclosure and pharmaceutical compositions provided herein can be employed in combination with other anti-viral agents to treat viral infection.

One aspect of the disclosure encompasses embodiments of a modified saponin having the formula:

wherein: $q_1$ can be H or OH; $q_2$ and $q_3$ can be each independently selected from CHO, $CH_3$, $CH_2OH$, H, or a component of an acetal group; $f_3$ and $f_4$ can be each independently OH or an acetyl, or C3 and C4 of a fuocsyl unit wherein $f_3$, and $f_4$ can form a cyclic ketal ring or cyclic carbonate ester; $f_5$ and $ga_5$ can be each independently selected from the group consisting of H, a methyl group, a carboxyl group, $R_4$—$NR_5$—C(O)—, and $R_4$—O—, wherein $R_4$ and $R_5$ can be each independently a linear chain having the structure $R_6$ $(CH_2)_{0-20}$— or Re [$(CH_2)_{0-20}O_{0-20}$ $(CH_2)_{0-20}]_{0-20}$, wherein $R_6$ can be H, OH, $COO(CH_2)_{0-6}H$, COOBn, $C(O)NR_7Bn$, $NR_7Bn$, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group of a carrier; and wherein $R_7$ can be H or an alkyl group; r3 can be H, a monosaccharide, disaccharide, or a trisaccharide; x3 can be H, a monosaccharide (except xylose) or a disaccharide; and ga3 can be H, a monosaccharide or a disaccharide.

In some embodiments of this aspect of the disclosure, the carrier can be selected from the group consisting of a polyamine polymer, a polyethylene glycol amine, poly (ethyleneimine), a nanocarbon, and an amino-containing biological molecule.

In some embodiments of this aspect of the disclosure, the modified saponin can have the formula I:

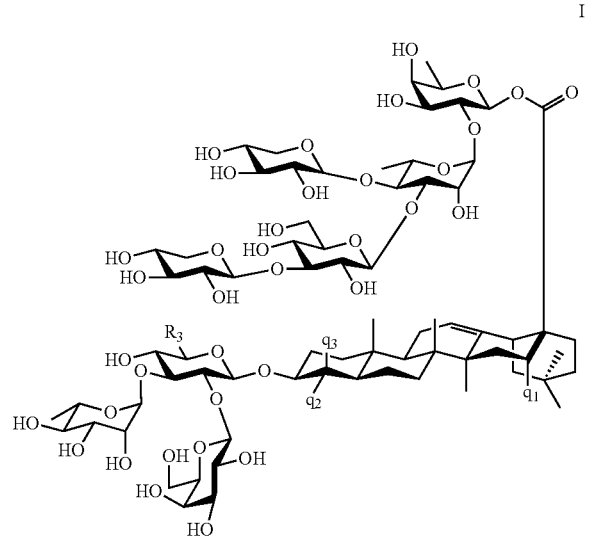

wherein: $q_1$ can be H or OH; $q_2$ and $q_3$ can be each independently selected from CHO, $CH_3$, $CH_2OH$, H, or a component of an acetal group; and $R_3$ can be selected from the group consisting of H, a methyl group, a carboxyl group, $R_4$—$NR_5$—C(O)—, and $R_4$—O—, wherein $R_4$ and $R_5$ can be each independently a linear chain having the structure $R_6(CH_2)_{0-20}$— or $R_6[(CH_2)_{0-20}O_{0-20}(CH_2)_{0-20}]_{0-20}$, wherein Re can be H, OH, $COO(CH_2)_{0-6}H$, COOBn, $C(O)NR_7Bn$, $NR_7Bn$, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group of a carrier; and wherein $R_7$ can be H or an alkyl group.

In some embodiments of this aspect of the disclosure, $R_3$ can be a carboxyl group.

In some embodiments of this aspect of the disclosure, $R_3$ can be $R_4$—NH—C(O)—, wherein $R_4$ can be a long-chain fatty acid having the structure HOOC—$(CH_2)_{6-20}$—.

In some embodiments of this aspect of the disclosure, $R_3$ can be an alkoxy group having the structure $H_3C$—$(CH_2)_{6-20}$—O—$CH_2$.

In some embodiments of this aspect of the disclosure, $R_3$ can be $R_4$—NH—C(O)—, wherein $R_4$ can be a long-chain alcohol having the structure HO—$(CH_2)_{6-20}$—.

In some embodiments of this aspect of the disclosure, $R_4$ can be a long-chain alkyl terminated with a functional group selected from an ester group, an ether group, an amino group, a cyano group, a carbonyl group, an azido group, and an aromatic group.

In some embodiments of this aspect of the disclosure, $R_3$ is $R_4$—NH—C(O)—, wherein $R_4$ can be a long-chain alkyl $R_6O(CH_2)_{6-20}$—, and wherein Re can be selected from a saccharide unit selected from the group consisting of a monosaccharide, a disaccharide, and trisaccharide.

In some embodiments of this aspect of the disclosure, $R_3$ can be $R_4$—NH—C(O)—, wherein $R_4$ can be a long-chain alkyl terminated with a monophosphoryl lipid A (MPL). In some embodiments of this aspect of the disclosure, $R_3$ can be $R_4$—NH—C(O)—, and wherein $R_4$ can be a long-chain alkyl terminated with a dipalmitoyl-S-glyceryl cysteine ($Pam_2Cys$) or a tripalmitoyl-S-glyceryl cysteine ($Pam_3Cys$).

In some embodiments of this aspect of the disclosure, $R_3$ can be $R_4$—NH—C(O)—, wherein $R_4$ can be a long-chain alkyl terminated with a muramyldipeptide unit.

In some embodiments of this aspect of the disclosure, $R_3$ can be $R_4$—NH—C(O)—, wherein $R_4$ can be a long-chain alkyl terminated with an α-Galcer unit.

In some embodiments of this aspect of the disclosure, $R_3$ can be $R_4$—NH—C(O)—, wherein $R_4$ can be a long-chain alkyl terminated with MS I unit.

In some embodiments of this aspect of the disclosure, $R_3$ can be $R_4$—NH—C(O)—, wherein $R_4$ can be a long-chain alkyl terminated with MS II unit.

In some embodiments of this aspect of the disclosure, the modified saponin can be selected from the group consisting of formulas A-E:

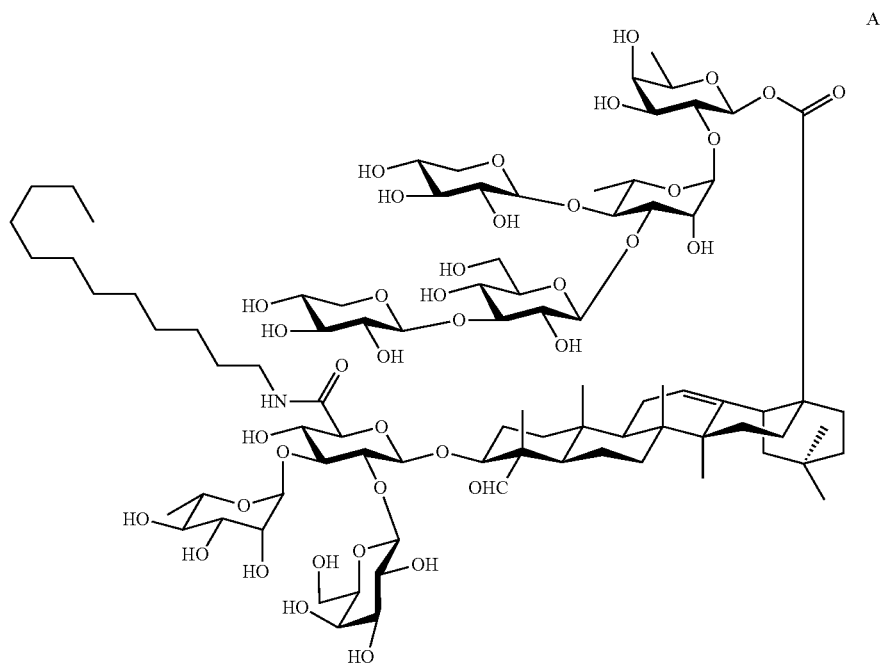

A

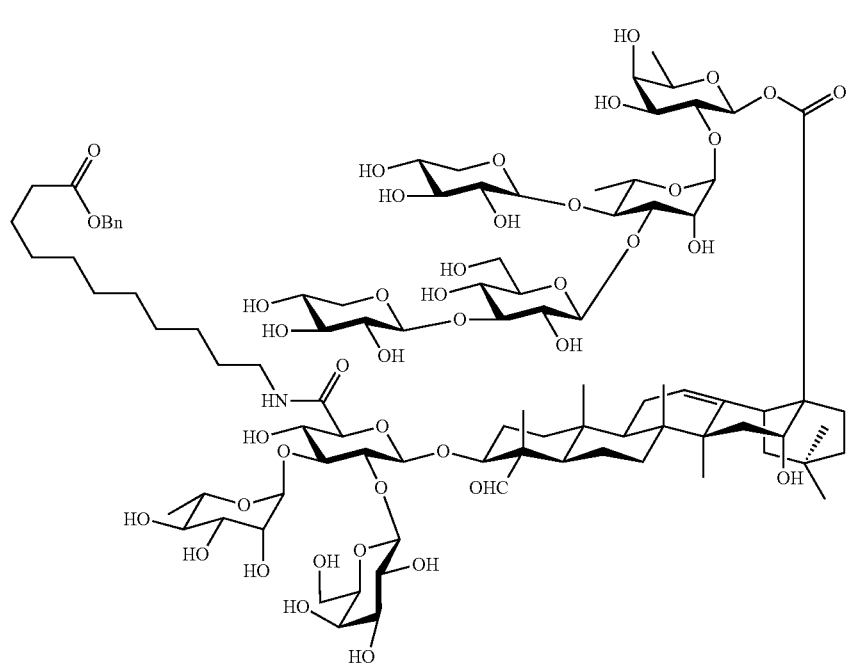
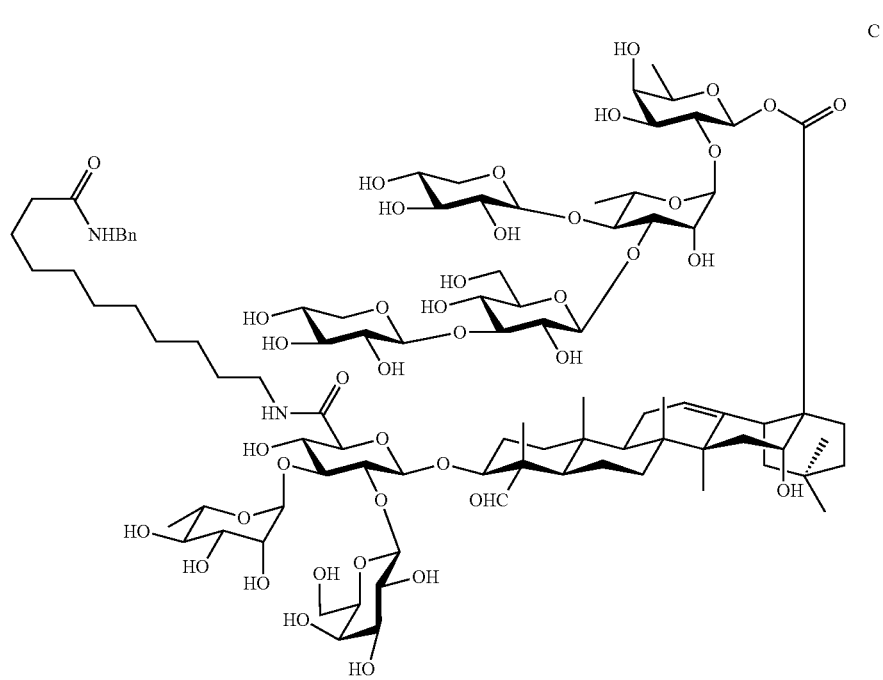

-continued
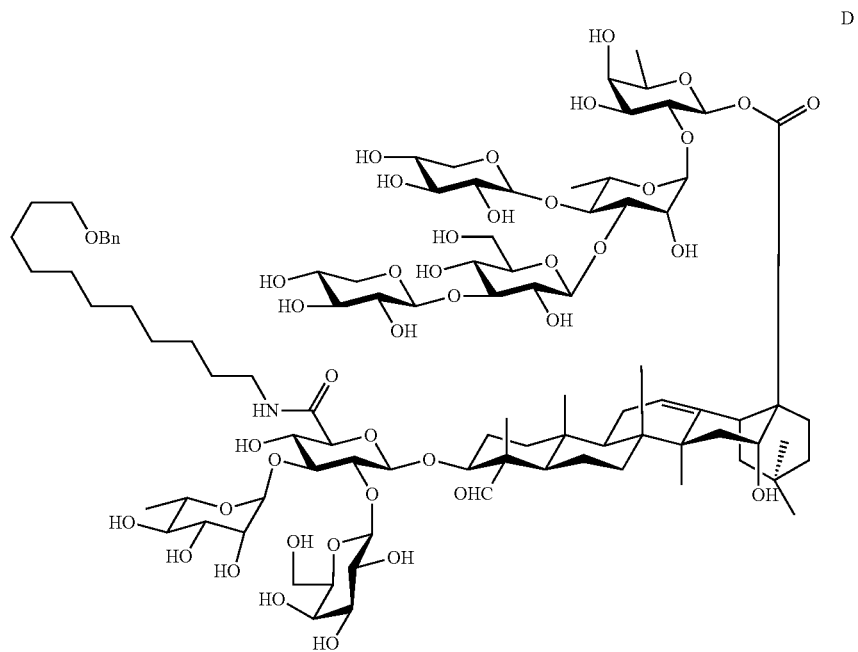
D
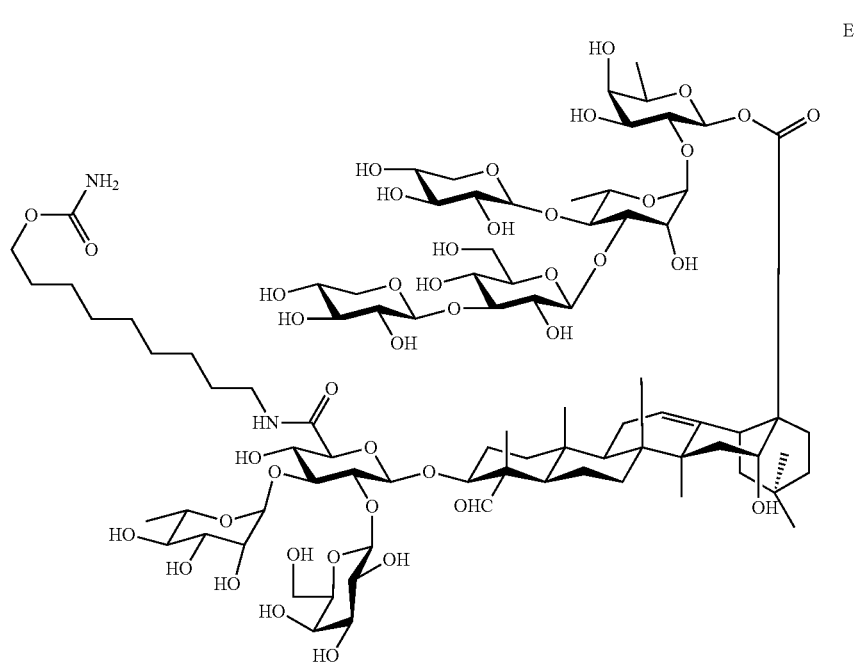
E

Another aspect of the disclosure encompasses embodiments of a pharmaceutical composition comprising a modified saponin having the formula:

In some embodiments of this aspect of the disclosure, the modified saponin can have the formula I:

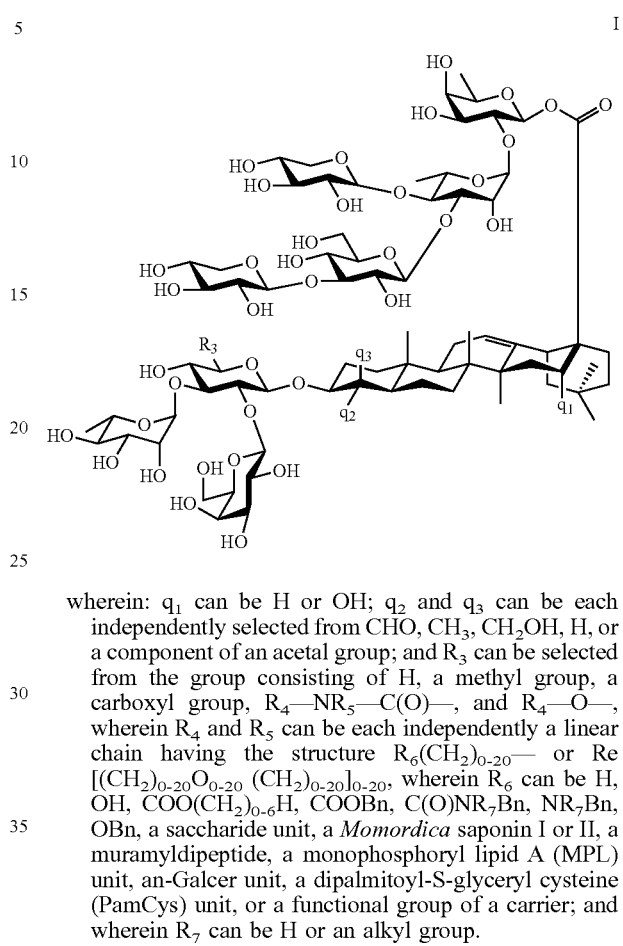

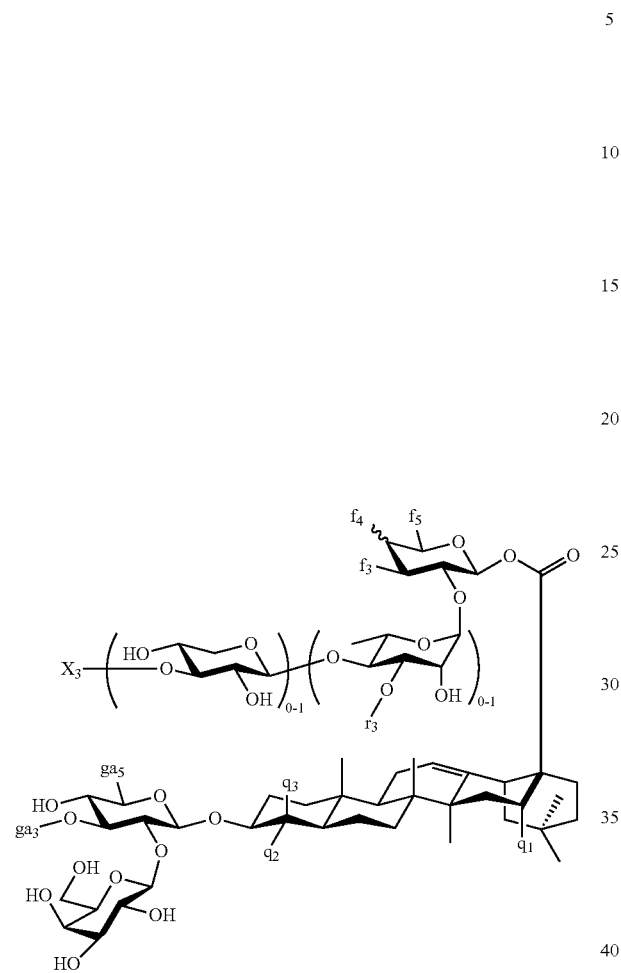

wherein: $q_1$ can be H or OH; $q_2$ and $q_3$ can be each independently selected from CHO, $CH_3$, $CH_2OH$, H, or a component of an acetal group; $f_3$ and $f_4$ can be each independently OH or an acetyl, or C3 and C4 of a fuocsyl unit wherein $f_3$, and $f_4$ can form a cyclic ketal ring or cyclic carbonate ester; $f_5$ and $ga_5$ can be each independently selected from the group consisting of H, a methyl group, a carboxyl group, $R_4$—$NR_5$—C(O)—, and $R_4$—O—, wherein $R_4$ and $R_5$ can be each independently a linear chain having the structure $R_6(CH_2)_{0-20}$— or $R_6[(CH_2)_{0-20}O_{0-20}(CH_2)_{0-20}]_{0-20}$, wherein $R_6$ can be H, OH, $COO(CH_2)_{0-6}H$, COOBn, $C(O)NR_7Bn$, $NR_7Bn$, OBn, a saccharide unit, a Momordica saponin I or II, a muramyldipeptide, a monophosphoryl lipid A (MPL) unit, an α-Galcer unit, a dipalmitoyl-S-glyceryl cysteine (PamCys) unit, or a functional group of a carrier; and wherein $R_7$ can be H or an alkyl group; r3 can be H, a monosaccharide, disaccharide, or a trisaccharide; x3 can be H, a monosaccharide (except xylose) or a disaccharide; and ga3 can be H, a monosaccharide or a disaccharide.

In some embodiments of this aspect of the disclosure, the carrier can be selected from the group consisting of a polyamine polymer, a polyethylene glycol amine, poly (ethyleneimine), a nanocarbon, and an amino-containing biological molecule.

wherein: $q_1$ can be H or OH; $q_2$ and $q_3$ can be each independently selected from CHO, $CH_3$, $CH_2OH$, H, or a component of an acetal group; and $R_3$ can be selected from the group consisting of H, a methyl group, a carboxyl group, $R_4$—$NR_5$—C(O)—, and $R_4$—O—, wherein $R_4$ and $R_5$ can be each independently a linear chain having the structure $R_6(CH_2)_{0-20}$— or Re $[(CH_2)_{0-20}O_{0-20}(CH_2)_{0-20}]_{0-20}$, wherein $R_6$ can be H, OH, $COO(CH_2)_{0-6}H$, COOBn, $C(O)NR_7Bn$, $NR_7Bn$, OBn, a saccharide unit, a Momordica saponin I or II, a muramyldipeptide, a monophosphoryl lipid A (MPL) unit, an-Galcer unit, a dipalmitoyl-S-glyceryl cysteine (PamCys) unit, or a functional group of a carrier; and wherein $R_7$ can be H or an alkyl group.

In some embodiments of this aspect of the disclosure, $R_3$ is a carboxyl group.

In some embodiments of this aspect of the disclosure, $R_3$ is $R_4$—NH—C(O)—, wherein $R_4$ is a long-chain fatty acid having the structure HOOC—$(CH_2)_{6-20}$—.

In some embodiments of this aspect of the disclosure, $R_3$ can be an alkoxy group having the structure $H_3C$—$(CH_2)_{6-20}$—O—.

In some embodiments of this aspect of the disclosure, $R_3$ can be $R_4$—NH—C(O)—, wherein $R_4$ can be a long-chain alcohol having the structure HO—$(CH_2)_{6-20}$—.

In some embodiments of this aspect of the disclosure, $R_4$ can be a long-chain alkyl terminated with a functional group selected from an ester group, an ether group, an amino group, a cyano group, a carbonyl group, an azido group, and an aromatic group. In some embodiments of this aspect of the disclosure, $R_3$ can be an alkoxy group having the structure $H_3C$—$(CH_2)_{6-20}$—O—$CH_2$—.

In some embodiments of this aspect of the disclosure, $R_3$ can be $R_4$—NH—C(O)—, wherein $R_4$ is a long-chain alcohol having the structure HO—$(CH_2)_{6-20}$—.

In some embodiments of this aspect of the disclosure, $R_4$ can be a long-chain alkyl terminated with a functional group selected from an ester group, an ether group, an amino group, a cyano group, a carbonyl group, an azido group, and an aromatic group.

In some embodiments of this aspect of the disclosure, $R_3$ can be $R_4$—NH—C(O)—, wherein $R_4$ can be a long-chain alkyl $R_6O(CH_2)_{6-20}$— and $R_6$ can be selected from a saccharide unit selected from the group consisting of a monosaccharide, a disaccharide, and trisaccharide.

In some embodiments of this aspect of the disclosure, $R_3$ can be $R_4$—NH—C(O)—, wherein $R_4$ can be a long-chain alkyl terminated with a monophosphoryl lipid A (MPL). In some embodiments of this aspect of the disclosure, $R_3$ is $R_4$—NH—C(O)—, wherein $R_4$ can be a long-chain alkyl terminated with a dipalmitoyl-S-glyceryl cysteine (Pam$_2$Cys) or a tripalmitoyl-S-glyceryl cysteine (Pam$_3$Cys).

In some embodiments of this aspect of the disclosure, $R_3$ can be $R_4$—NH—C(O)—, wherein $R_4$ can be a long-chain alkyl terminated with a muramyldipeptide unit.

In some embodiments of this aspect of the disclosure, $R_3$ can be $R_4$—NH—C(O)—, wherein $R_4$ can be a long-chain alkyl terminated with an α-Galcer unit.

In some embodiments of this aspect of the disclosure, $R_3$ can be $R_4$—NH—C(O)—, wherein $R_4$ can be a long-chain alkyl terminated with MS I unit.

In some embodiments of this aspect of the disclosure, $R_3$ can be $R_4$—NH—C(O)—, wherein $R_4$ can be a long-chain alkyl terminated with MS II unit.

In some embodiments of this aspect of the disclosure, the modified saponin can be selected from the group consisting of formulas A-E:

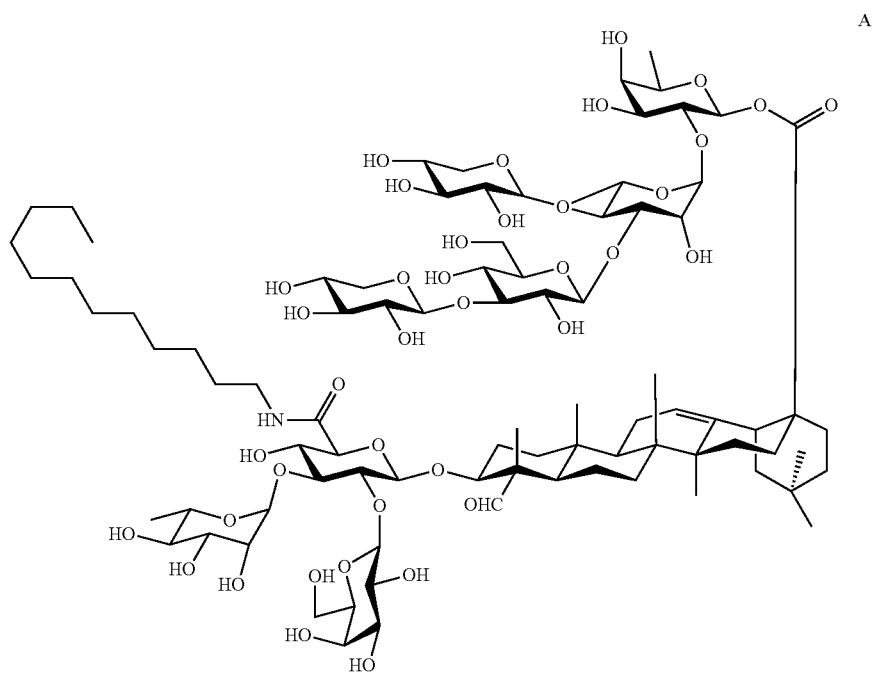

A

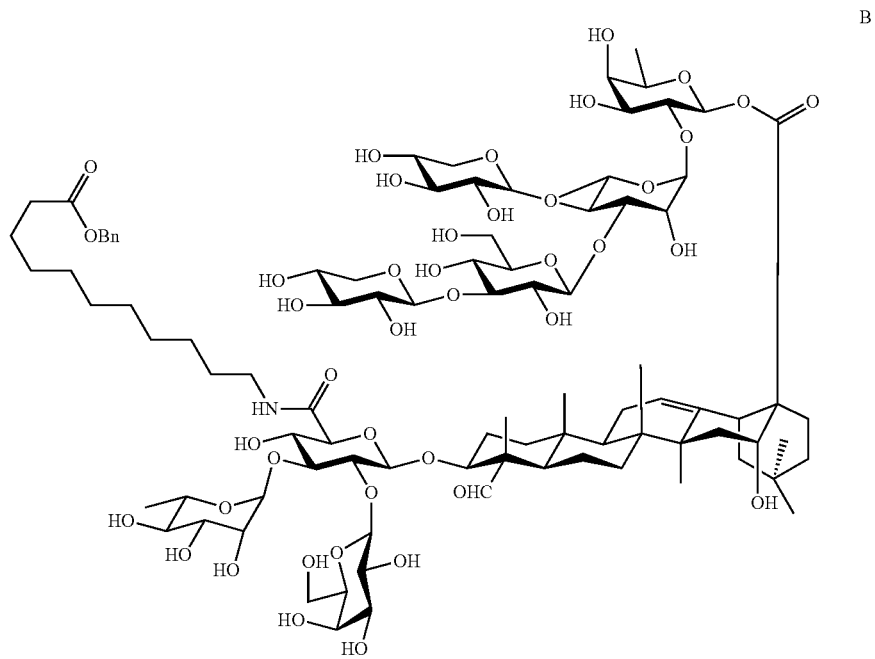

B

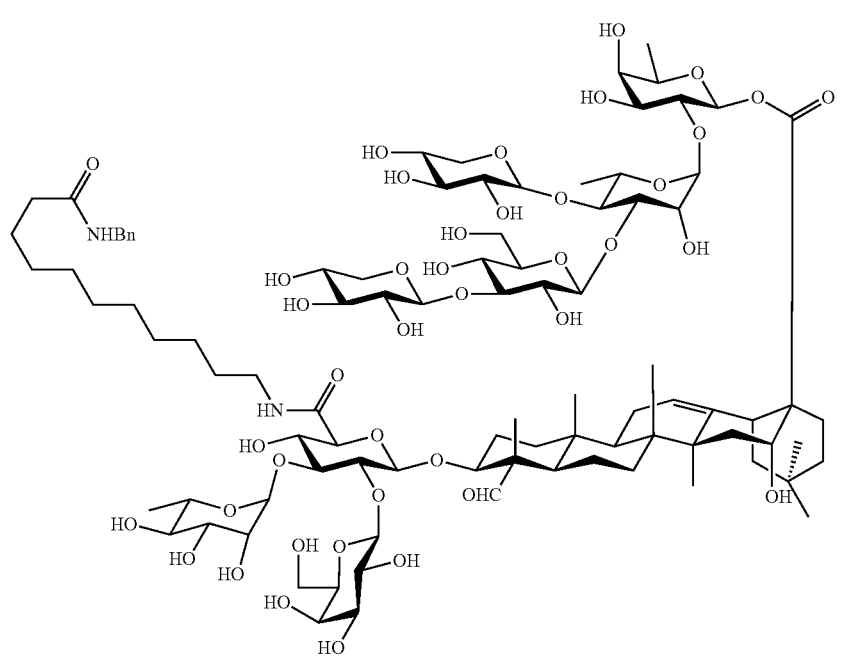
C
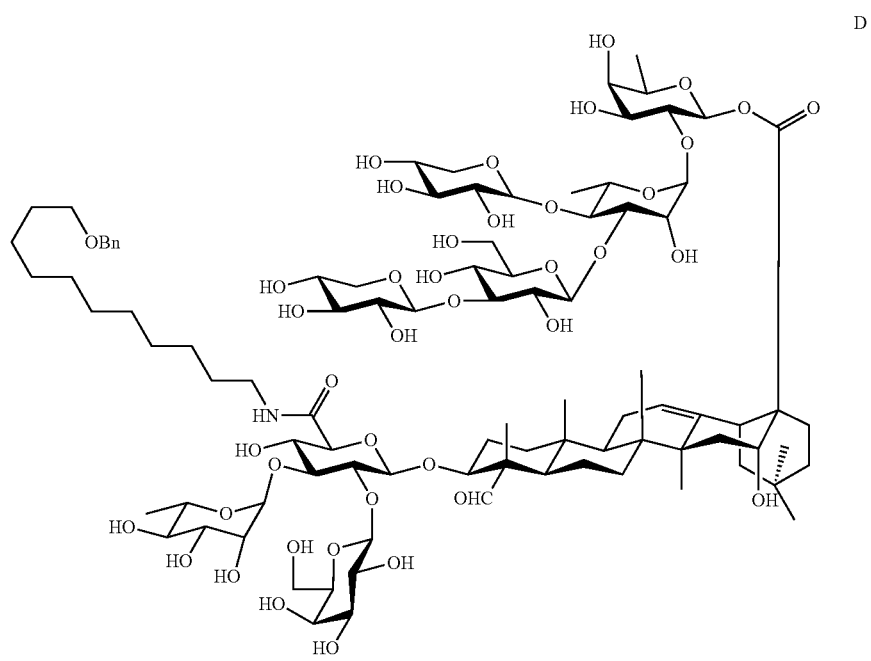
D

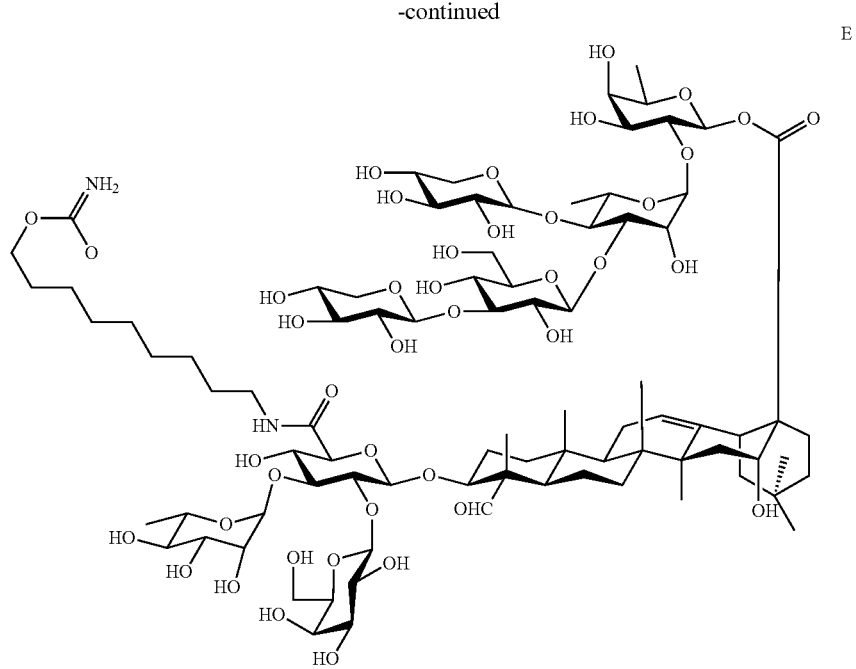

In some embodiments of this aspect of the disclosure, the pharmaceutical composition can further comprise at least one immunogen.

In some embodiments of this aspect of the disclosure, the pharmaceutical composition can further comprise a pharmaceutically acceptable carrier.

In some embodiments of this aspect of the disclosure, the pharmaceutical composition can be formulated for administering to an animal or human subject.

In some embodiments of this aspect of the disclosure, the pharmaceutical composition can further comprise at least one cancer therapeutic agent, wherein the at least one chemotherapeutic agent and the saponin derivative are admixed in a pharmaceutically acceptable formulation or covalently linked to each other, and a pharmaceutically acceptable carrier.

Yet another aspect of the disclosure encompasses embodiments of a method of increasing the immunogenicity of an immunogen when administered to an animal or human subject, the method comprising the step of administering to the subject a vaccine comprising at least a pharmaceutical composition according to the disclosure.

Still yet another aspect of the disclosure encompasses embodiments of a synthetic route for the synthesis of a saponin derivative, the synthetic route comprising coupling a natural saponin with a functionalized side chain molecule, wherein the functionalized side chain comprises an amino group or hydroxyl group.

In some embodiments of this aspect of the disclosure, the natural saponin can be obtained from *Momordica cochinchinensis* Spreng.

In some embodiments of this aspect of the disclosure, the natural saponin can be coupled to the functionalized side chain molecule via an amide formation reaction or an ester formation reaction.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

General.

Organic solutions were concentrated by rotary evaporation at about 12 Torr. Flash column chromatography was performed employing 230-400 mesh silica gel. Thin-layer chromatography was performed using glass plates precoated to a depth of 0.25 mm with 230-400 mesh silica gel impregnated with a fluorescent indicator (254 nm). Infrared (IR) data are presented as frequency of absorption (cm$^{-1}$). Proton and carbon-13 nuclear magnetic resonance ($^1$H NMR or $^{13}$C NMR) spectra were recorded on 400, 700, and 850 MHz NMR spectrometers; Chemical shifts are expressed in parts per million (o scale) downfield from tetramethylsilane and are referenced to residual protium in the NMR solvent (CHCl$_3$: δ=7.26). Data are presented as follows: chemical shift, multiplicity (s=singlet, d=doublet, t=triplet, q=quartet, m=multiplet and/or multiple resonances, AB=AB quartet), coupling constant in Hertz (Hz), integration. Anhydrous solvents were used without distillation. Solvents for workup and column chromatography, were obtained from commercial vendors and used without further purification. The purity of the products for immunological studies was determined by a combination of HPLC and 1H NMR, and found to be ≥95%.

Example 2

Precursors of the adjuvants of the disclosure were isolated from the seed saponins of *Momordica cochinchinensis* SPRENG. (Cucurbitaceae), a more accessible source of the adjuvants and adjuvant precursors than other saponin series of adjuvants.

Figure 11:
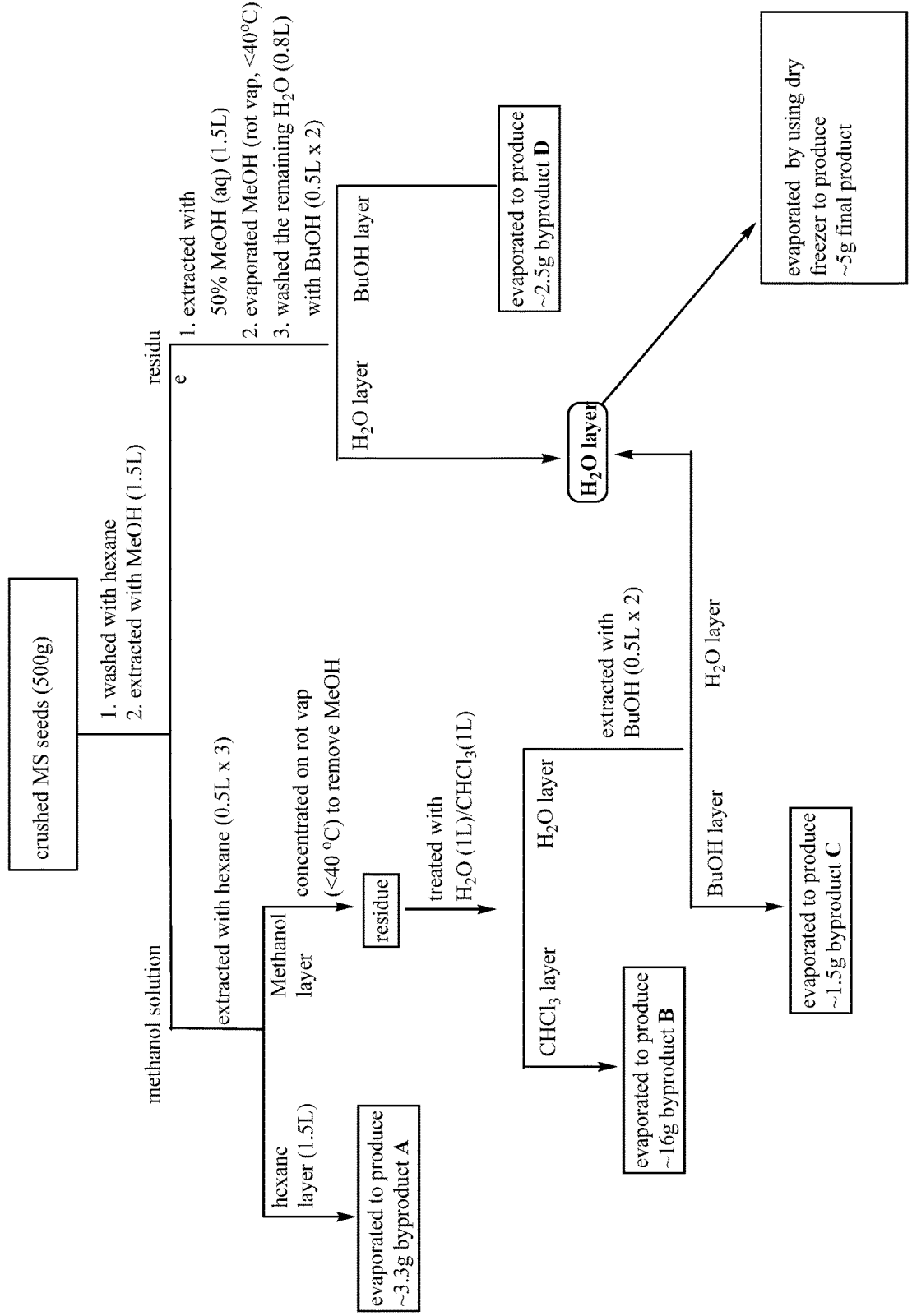
FIG. 11 illustrates a flow chart for the purification of MS compounds.
Figure 12A:
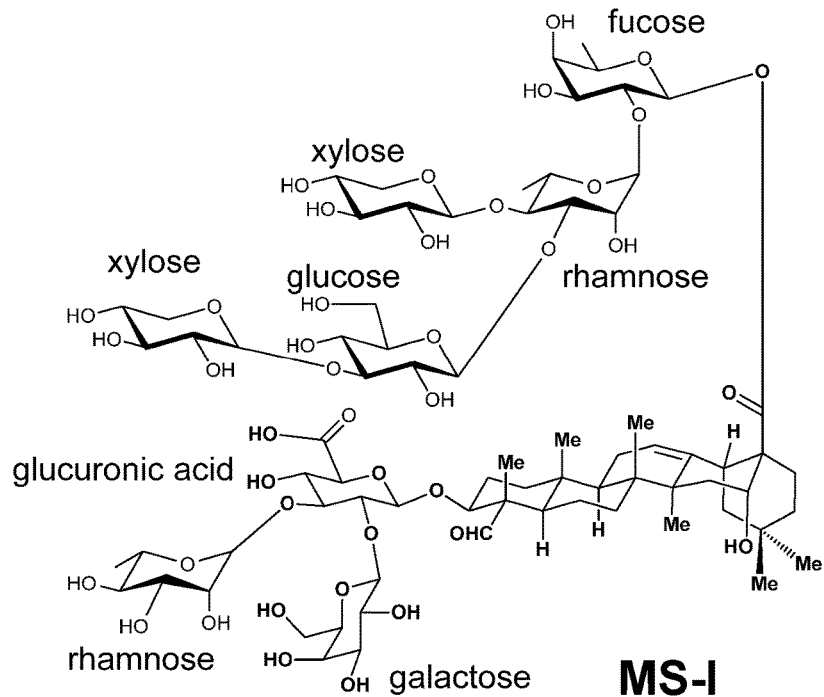
FIG. 12A illustrates natural product MS-I isolated from the seed saponins of *Momordica cochinchinensis* SPRENG. (Cucurbitaceae).
Figure 12B:
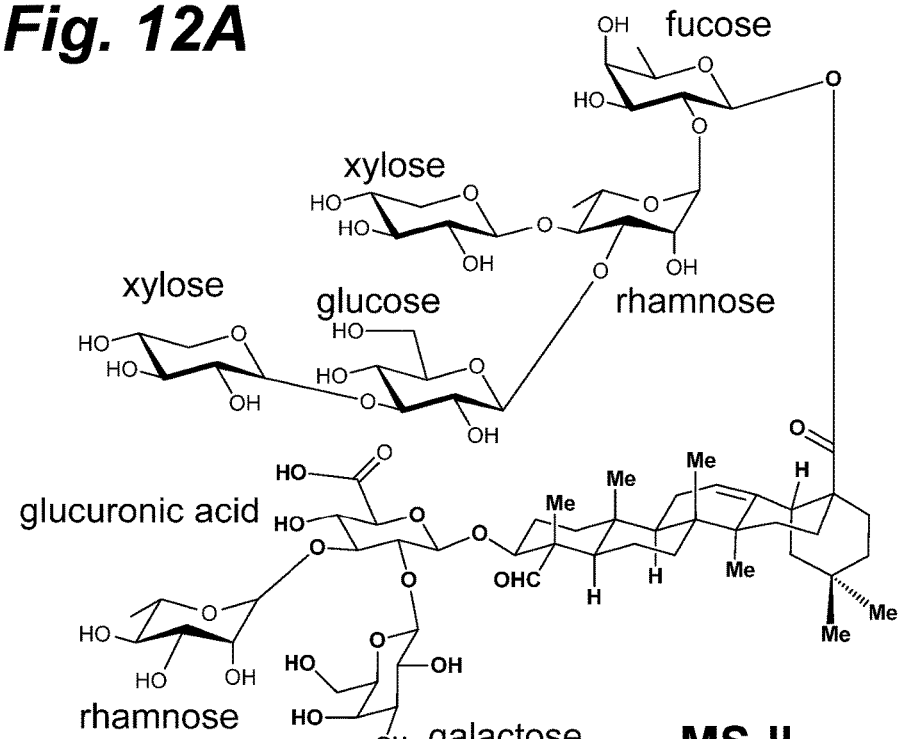
FIG. 12B illustrates natural product MS-II isolated from the seed saponins of *Momordica cochinchinensis* SPRENG. (Cucurbitaceae).
Figure 12C:
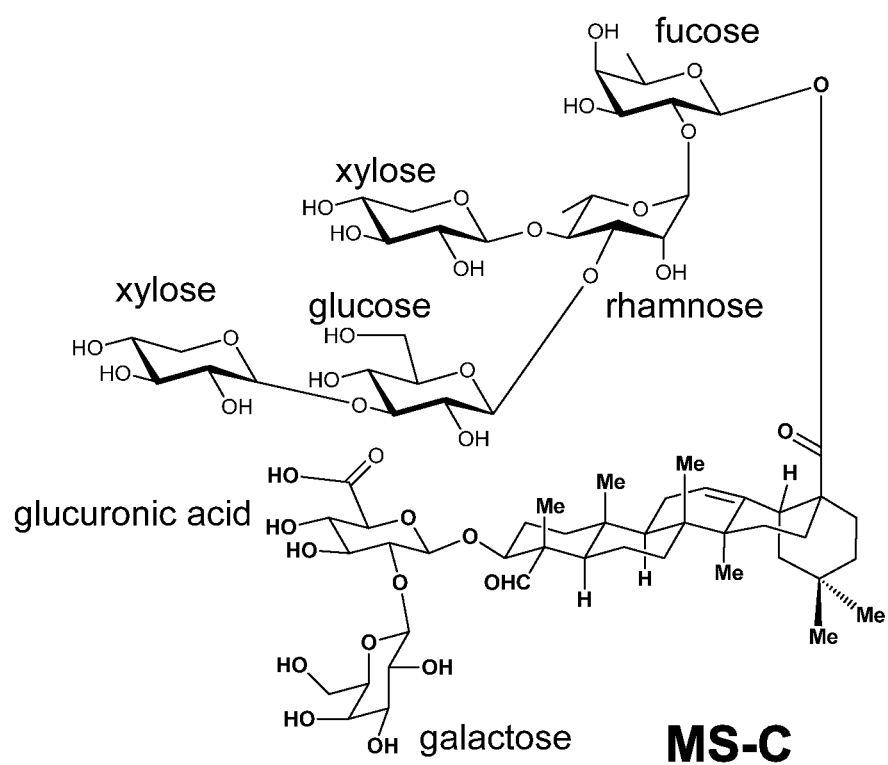
FIG. 12C illustrates natural product MS-C isolated from the seed saponins of *Momordica cochinchinensis* SPRENG. (Cucurbitaceae).

Natural products MS-I, MS-II, and MS-C isolated from the seed saponins of *Momordica cochinchinensis* SPRENG. (Cucurbitaceae) according to the flow chart shown in FIG. 11, are illustrated in FIGS. 12A-12C, respectively.

Example 3

Figure 5:
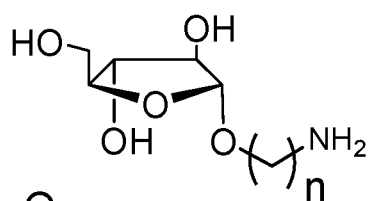
FIG. 5 illustrates examples of side chains.
Figure 5:
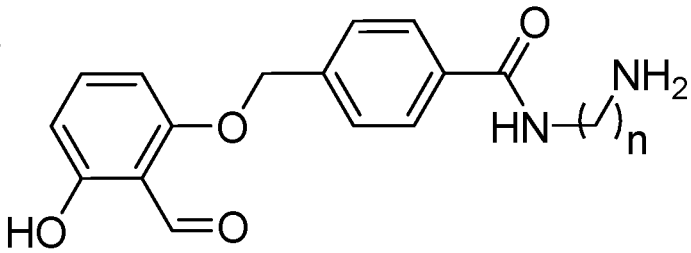
Figure 5:
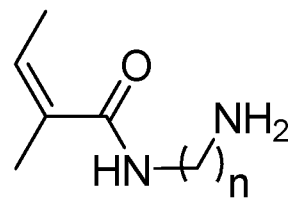
Figure 5:
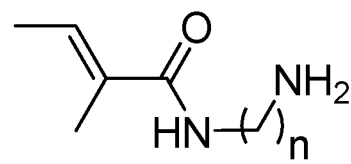
Figure 5:
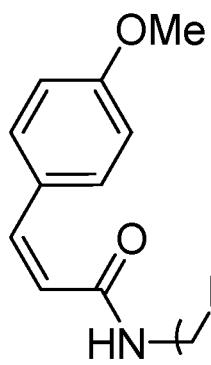
Figure 5:
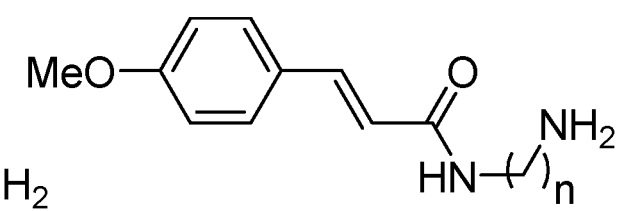
Figure 6A:
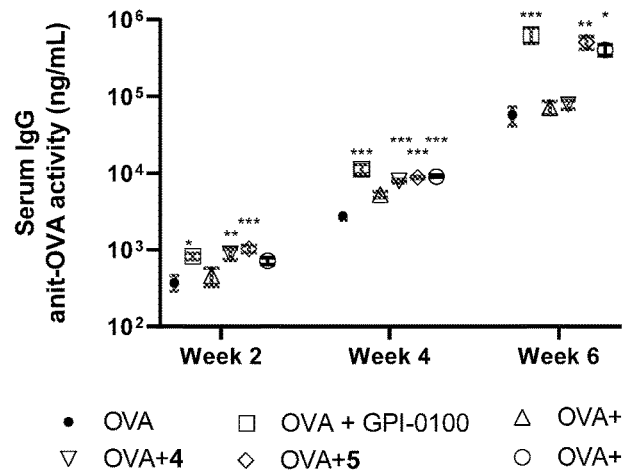
FIGS. 6A-6C illustrate serum IgG, IgG1, and IgG2a anti-OVA responses in mice immunized by the subcutaneous route with ovalbumin (OVA) alone, with GPI-0100, and OVA with the natural saponins 3 or 4, or their respective derivatives 5 or 6.
Figure 6B:
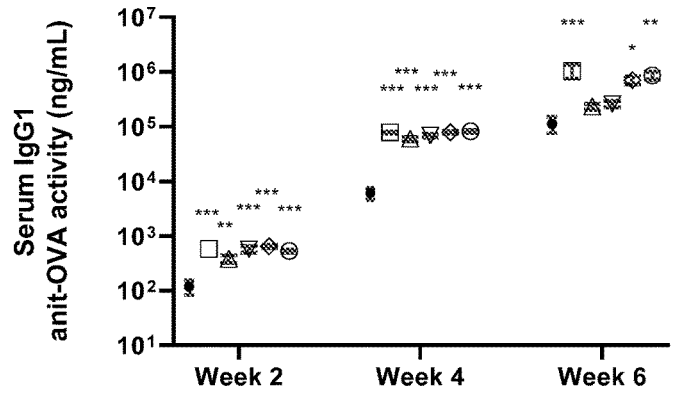
Figure 6C:
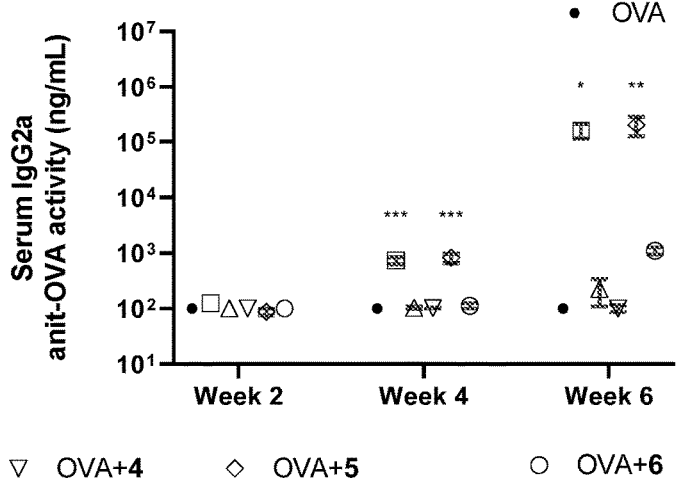

Choice of Side Chain:

Side chains (as shown, for example, in FIG. 5) can be incorporated with a standard amide formation procedure to produce various saponin derivatives. Preliminary studies revealed that the structure of the incorporated side chain has a significant impact on adjuvant activity in terms of magnitude and nature of the stimulated immune responses. Therefore, analogs with different side chains can be synthesized. QS-21 analogs that incorporate a side chain terminated with a polar functional group significantly improve the derivatives' adjuvant activity. Side chain a has a terminal carboxyl group. In earlier studies, a terminal carboxyl group can change IgG subclass distribution, leading to more IgG2a: production, which can be possibly related to an enhanced Th1 immunity. Side chains b and c can fine-tune the balance between hydrophilicity and hydrophobicity of the whole molecule, which could be relevant to the adjuvant activity. Side chains d-f could provide similar insights as side chains a-c. Earlier SAR studies of QS-21 analogs also indicated that side chain h with a terminal sugar unit also significantly improve the analog's adjuvant activity. Side: chain g is a simplified version of side chain h. Side chain i has a terminal aldehyde moiety. SAR studies showed that the carbonyl group on the quillaic acid core of the natural QS-21 is crucial to the extraordinary adjuvant activity of QS-21. It was suggested that the carbonyl group could form imine with an amino group on T cell surface receptor. This Schiff-base formation probably provides a co-stimulatory signal and leads to T-cell activation and Th1 immunity. Incorporation of an additional aldehyde moiety could enhance the Schiff-base-induced interaction between the adjuvant molecule and T cell surface receptor and thus enhance Th1 immunity. Side chain j has a terminal tucaresol moiety bearing an aromatic carbonyl group. Tucaresol has been studied as an adjuvant; it enhances antigen-specific humoral and cellular immune responses. Side chains k and I (each has two cis/trans isomers) originate from natural saponins such as escin and *gypsophila* saponins, recombination of them with natural saponins that already show high humoral immunity could lead to enhancement in cell-mediated immunity.

MPL Side Chain 23d for QS-MPL Combination Adjuvant:

The terminal group can also be derived from an established adjuvant moiety. QS-21 and its variants' can act synergistically in animal models with other adjuvants such as monophosphoryl lipid A (MPL, a TLR4 agonist) (Ashtekar et al., (2012) *PloS one*. 7: e50460). MPL is known for TLR4 activation, enhancing Th1 type cellular and humoral immune responses significantly. It typically boosts serum Ab titers by 10-20 fold when compared to vaccine alone. Human vaccine trials indicate that MPL has a safety profile similar to that of alum (Wang et al., (2016) *J. Org. Chem.* 81:9560-9566). Accordingly, the MPL side chain 23d can be incorporated into the saponin derivatives produce the corresponding QS-MPL single-molecule combination adjuvants.

Pam2Cys Side Chain 23e for QS-Pam2Cys Combination Adjuvant:

Pam$_2$Cys and Pam$_3$Cys, synthetic analogs of bacterial lipopeptides, are two TLR2 agonists used as vaccine adjuvants in preclinical studies. These lipid adjuvants enhance both humoral and cell-mediated responses but they are less effective in boosting CTL responses. They have been shown to be effective for epitope-based vaccines and do not exhibit the harmful side effects that are commonly associated with many other adjuvant formulations. Chemical incorporation of Pam3Cys into a fully synthetic carbohydrate-based anticancer vaccine has shown results that demonstrated that chemically connecting the TLR2 agonist is feasible to enhance immune response. Synthesis of the properly protected Pam2Cys moiety is a routine practice and known in the literature.

Example 4

For 4b (14.4 mg, 78%), $^1$H NMR (600 MHZ, CD$_3$OD) (characteristic protons) δ 9.49 (s, 1H), 7.41-7.37 (m, 4H), 7.35 (m, 1H), 5.36 (d, J=1.5 Hz, 1H), 5.34 (d, J=8.2 Hz, 1H), 5.29 (t, J=3.3 Hz, 1H), 5.15 (s, 2H), 5.05 (d, J=1.5 Hz, 1H), 4.67 (d, J=7.9 Hz, 1H), 4.60 (d, J=7.8 Hz, 1H), 4.52 (d, J=7.6 Hz, 1H), 4.51 (d, J=6.9 Hz, 1H), 4.48 (d, J=7.2 Hz, 1H), 4.29 (t, J=2.4 Hz, 1H), 4.04 (dd, J=3.2, 1.9 Hz, 1H), 4.01 (dd, J=11.4, 5.3 Hz, 1H), 3.16 (t, J=10.9 Hz, 1H), 3.07 (dd, J=9.1, 8.0 Hz, 1H), 2.83 (dd, J=12.9, 3.6 Hz, 1H), 2.40 (t, J=7.4 Hz, 2H), 2.07 (td, J=12.8, 2.3 Hz, 1H), 1.02 (s, 3H), 0.94 (s, 3H), 0.93 (s, 3H), 0.83 (s, 3H); $^{13}$C NMR (150.9 MHZ, CD$_3$OD) δ 209.3, 176.5, 173.8, 169.9, 169.8, 143.6, 136.4, 128.2, 127.9, 127.8, 121.8, 104.6, 103.9, 103.7, 102.8, 102.5, 101.8, 100.0, 94.0, 87.3, 84.4, 84.1, 81.5, 77.7, 77.6, 76.6, 76.1, 76.0, 75.4, 74.8, 74.5, 74.0, 73.6, 73.0, 72.8, 72.4, 72.2, 71.6, 71.3, 70.8, 70.7, 70.5, 70.1, 69.9, 69.6, 69.2, 69.1, 68.1, 67.4, 65.8, 65.7, 65.6, 60.8, 54.9, 46.6, 46.0, 41.8, 41.6, 39.6, 38.9, 38.7, 38.0, 35.7, 33.7, 33.5, 32.2, 32.1, 31.5, 30.1, 29.2, 29.1, 29.0, 28.9, 28.8, 27.5, 26.5, 24.8, 24.7, 24.4, 23.2, 22.8, 22.6, 20.2, 17.1, 16.5, 16.4, 15.1, 15.0, 9.5; HRMS (ESI-TOF) m/z: [M+H]$^+$ calcd for C$_{94}$H$_{148}$NO$_{41}$ 1946.9527; found 1946.9496.

Example 5

For 4c (56.0 mg, 98%), $^1$H NMR (600 MHZ, CD$_3$OD) (characteristic protons) δ 9.48 (s, 1H), 5.35-5.32 (m, 2H), 5.28 (s, 1H), 5.05 (s, 1H), 4.46 (d, J=7.8 Hz, 1H), 4.60 (d, J=7.8 Hz, 1H), 4.51 (d, J=7.5 Hz, 2H), 4.48 (m, 1H), 4.28 (s, 1H), 4.05 (s, 1H), 4.01 (dd, J=11.3, 5.1 Hz, 1H), 3.16 (t, J=11.0 Hz, 1H), 3.07 (t, J=8.5 Hz, 1H), 2.83 (d, J=10.4 Hz, 1H), 2.31 (t, J=7.4 Hz, 1H), 2.07 (t, J=13.2 Hz, 1H), 1.02 (s, 3H), 0.81 (s, 3H); $^{13}$C NMR (150.9 MHZ, CD$_3$OD) δ 209.4, 176.5, 176.3, 169.8, 143.5, 121.8, 104.6, 103.9, 103.6, 102.8, 102.5, 101.9, 100.0, 94.0, 87.2, 84.4, 84.2, 81.5, 77.6, 76.6, 76.1, 76.0, 75.4, 74.8, 74.5, 74.0, 73.6, 73.01, 72.98, 72.4, 72.2, 71.6, 71.3, 70.8, 70.6, 70.5, 70.1, 69.9, 69.6, 69.2, 69.1, 68.1, 67.5, 65.7, 65.6, 60.8, 54.9, 46.6, 46.0, 41.8, 41.6, 39.6, 38.8, 38.0, 35.7, 33.6, 32.2, 31.6, 30.2, 29.4, 29.2, 29.14, 29.11, 28.9, 27.5, 26.5, 24.9, 24.7, 24.4, 23.2, 22.8, 22.7, 20.2, 17.1, 16.6, 16.4, 15.2, 15.0, 9.5; HRMS (ESI-TOF) m/z: [M+H]$^+$ calcd for C$_{87}$H$_{142}$NO$_{41}$ 1856.9057; found 1856.8998.

Example 6

For 5b (12.5 mg, 72%), $^1$H NMR (700 MHZ, CD$_3$OD) (characteristic protons) δ 9.51 (s, 1H), 7.39-7.38 (m, 4H), 7.34 (m, 1H), 5.44 (d, J=1.5 Hz, 1H), 5.34 (t, J=3.2 Hz, 1H), 5.24 (d, J=8.3 Hz, 1H), 5.15 (s, 2H), 5.05 (d, J=1.3 Hz, 1H), 4.75 (d, J=7.9 Hz, 1H), 4.57 (d, J=7.8 Hz, 1H), 4.54 (s, 1H), 4.52-4.47 (m, 2H), 4.46 (d, J=7.6 Hz, 1H), 4.26 (t, J=3.2, 1.8

Hz, 1H), 4.06-4.02 (m, 2H), 3.19 (t, J=10.7 Hz, 1H), 3.15 (dd, J=9.2, 8.1 Hz, 1H), 2.92 (dd, J=9.4, 4.2 Hz, 1H), 2.40 (t, J=7.3 Hz, 2H), 2.31 (t, J=13.6 Hz, 1H), 1.44 (s, 3H), 1.26 (d, J=6.2 Hz, 3H), 1.24 (d, J=6.4 Hz, 3H), 1.19 (s, 3H), 1.21 (s, 3H), 1.04 (s, 3H), 0.95 (s, 3H), 0.89 (s, 3H), 0.82 (s, 3H); $^{13}$C NMR (150.9 MHZ, CD$_3$OD) δ 209.6, 175.5, 173.8, 169.8, 143.5, 136.4, 128.2, 128.1, 127.9, 127.8, 121.5, 104.7, 103.8, 103.5, 102.8, 102.7, 101.9, 99.3, 94.0, 87.4, 84.6, 84.5, 82.1, 77.3, 76.8, 76.4, 76.0, 75.42, 75.38, 75.1, 74.2, 74.0, 73.6, 73.3, 73.0, 72.4, 72.3, 71.6, 71.51, 71.45, 70.8, 70.7, 70.5, 70.1, 70.0, 69.6, 69.2, 69.1, 68.0, 67.4, 65.8, 65.7, 60.8, 60.6, 54.8, 48.5, 46.6, 41.6, 41.1, 39.7, 38.7, 38.0, 35.7, 35.2, 33.7, 32.8, 32.0, 30.5, 29.9, 29.4, 29.2, 29.1, 29.0, 28.9, 28.7, 26.5, 25.9, 24.7, 23.3, 23.1, 20.0, 17.0, 16.5, 16.4, 15.1, 9.6; HRMS (ESI-TOF) m/z: [M+H]$^+$ calcd for C$_{94}$H$_{148}$NO$_{42}$ 1962.9476; found 1962.9436.

Example 7

For 5c (11.0 mg, 96%), $^1$H NMR (700 MHZ, CD$_3$OD) (characteristic protons) δ 9.51 (s, 1H), 5.44 (d, J=1.3 Hz, 1H), 5.35 (t, J=3.4 Hz, 1H), 5.25 (d, J=8.3 Hz, 1H), 5.05 (s, 1H), 4.75 (d, J=7.8 Hz, 1H), 4.57 (d, J=7.9 Hz, 1H), 4.54 (d, 1H), 4.45-4.47 (m, 2H), 4.46 (d, J=7.6 Hz, 1H), 4.25 (s, 1H), 4.06-4.00 (m, 2H), 3.19 (t, J=11.3 Hz, 1H), 3.15 (dd, J=9.3, 8.1 Hz, 1H), 2.31 (t, J=13.9 Hz, 1H), 2.29 (t, J=7.5 Hz, 2H), 1.44 (s, 3H), 1.21 (s, 3H), 1.05 (s, 3H), 0.97 (s, 3H), 0.90 (s, 3H), 0.82 (s, 3H); HRMS (ESI-TOF) m/z: [M+H]$^+$ calcd for C$_{87}$H$_{142}$NO$_{42}$ 1872.9006; found 1872.9016.

Example 8

Preparation of 9b and 9c:

Conjugate 10 (30.0 mg, 7.9 mmol) and 10% Pd/C (6.0 mg) in 1.5 mL of THF/MeOH (2:1) were subjected to hydrogen gas at 55 psi for 16 h. The suspension was then filtered through a celite plug, concentrated, and re-dissolved in 0.6 mL of EtOH/H$_2$O (v/v 5:1). To the solution was added 11-aminoundecanoic acid benzyl ester hydrochloride (6.4 mg, 20 μmol), N-methylmorpholine (NMM) (13.0 mg, 127 μmol), hydroxybenzotriazole (HOBt) (8.8 mg, 58 μmol), and 1-ethyl-3-(3-dimethylaminopropyl) carbodiimide hydrochloride (EDC·HCl) (11.4 mg, 58 μmol) at room temperature. The reaction mixture was stirred for 1 day and then filtered. The filtrate was purified with RP HPLC by using a semi-Prep C18, 250×10 mm, 5 micron column and H$_2$O/MeCN gradients (90%-10% H$_2$O over 30 minutes with a 3 mL/min flow rate). The desired product had a retention time of 23 min and the fraction was concentrated on a rotary evaporator at room temperature to remove MeCN, and the remaining water was then removed on a lyophilizer to provide the intermediate as a white solid (8.0 mg, 52%) over two steps. The intermediate was dissolved in methanol (0.5 mL) and H$_2$O (0.3 mL) and treated with K$_2$CO$_3$ (20 mg) overnight. The reaction mixture was neutralized with acetic acid, and purified with RP HPLC by using a semi-Prep C18, 250×10 mm, 5 micron column and H$_2$O/MeCN gradients (90%-10% H$_2$O over 45 minutes with a 3 mL/min flow rate). The desired product had a retention time of 23 min and the fraction was concentrated on a rotary evaporator at room temperature to remove MeCN, and the remaining water was then removed on a lyophilizer to provide 9b (4.4 mg, 57%) as a white solid. By using the same debenzylation procedure described for 4c/5c, 9c was obtained (4.0 mg, 96%) as a white solid.

Example 9

For 9b, $^1$H NMR (600 MHZ, CD$_3$OD) (characteristic protons) δ 9.38 (s, 1H), 7.87 (t, J=5.5 Hz, 1H), 7.27-7.24 (m, 4H), 7.22 (m, 1H), 5.22-5.19 (m, 2H), 5.17 (d, J=8.2 Hz, 1H), 5.03 (s, 2H), 4.71 (d, J=7.7 Hz, 1H), 4.63 (d, J=7.9 Hz, 1H), 4.48 (d, J=7.8 Hz, 1H), 4.44 (d, J=7.7 Hz, 1H), 4.41 (d, J=7.5 Hz, 1H), 4.38 (s, 1H), 4.34 (d, J=7.4 Hz, 1H), 4.16 (dd, J=2.9, 1.9 Hz, 1H), 2.85 (dd, J=13.9, 4.0 Hz, 1H), 2.28 (t, J=7.3 Hz, 2H), 2.21 (t, J=13.3 Hz, 1H), 1.29 (s, 3H), 1.11 (d, J=6.4 Hz, 3H), 1.07 (s, 3H), 0.90 (s, 3H), 0.84 (s, 3H), 0.78 (s, 3H), 0.66 (s, 3H); $^{13}$C NMR (176.0 MHZ, CD$_3$OD) δ 211.4, 177.1, 175.2, 170.8, 145.0, 137.8, 129.6, 129.3, 129.2, 123.1, 105.9, 105.3, 105.0, 104.8, 104.7, 103.7, 101.7, 95.3, 95.2, 88.3, 87.0, 86.3, 83.0, 78.9, 78.23, 78.20, 78.0, 77.8, 77.7, 77.0, 76.4, 76.3, 75.37, 75.34, 75.26, 75.0, 74.9, 74.6, 73.6, 73.5, 72.7, 71.4, 71.3, 71.1, 71.0, 70.7, 69.9, 68.9, 67.2, 66.6, 62.3, 61.9, 56.3, 42.7, 42.2, 41.1, 40.1, 39.4, 37.1, 36.6, 36.5, 35.1, 33.8, 33.4, 32.1, 31.3, 30.8, 30.6, 30.52, 30.45, 30.3, 30.2, 27.9, 27.3, 26.1, 26.0, 24.8, 24.5, 21.6, 18.7, 17.8, 16.52, 16.45, 11.0; HRMS (ESI-TOF) m/z: [M+Na]$^+$ calcd for C$_{93}$H$_{145}$NO$_{42}$Na 1970.9139; found 1970.9172.

Example 10

For 9c, $^1$H NMR (700 MHz, CD$_3$OD) (characteristic protons) d 9.50 (s, 1H), 7.95 (t, J=5.9 Hz, 1H), 5.36-5.32 (m, 2H), 5.30 (d, J=8.2 Hz, 1H), 4.75 (d, J=7.9 Hz, 1H), 4.60 (d, J=7.8 Hz, 1H), 4.56 (d, J=7.7 Hz, 1H), 4.54 (d, J=7.6 Hz, 1H), 4.50 (s, 1H), 4.46 (d, J=7.5 Hz, 1H), 4.29 (dd, J=3.2, 1.7 Hz, 1H), 2.98 (dd, J=14.1, 3.8 Hz, 1H), 2.33 (t, J=13.8 Hz, 1H), 2.33 (t, J=7.4 Hz, 2H), 1.41 (s, 3H), 1.31 (d, J=6.2 Hz, 3H), 1.24 (d, J=6.4 Hz, 3H), 1.21 (s, 3H), 1.03 (s, 3H), 0.98 (s, 3H), 0.91 (s, 3H), 0.79 (s, 3H); HRMS (ESI-TOF) m/z: [M+Na]$^+$ calcd for C$_{86}$H$_{139}$NO$_{42}$Na 1880.8669; found 1880.8645.

Example 11

Antigens:

The chicken egg albumin for in vivo use (Vac-pova) was purchased from InvivoGen. Recombinant *Porphyromonas gingivalis* HagB was prepared as previously described (Zhang et al., (2003) *Vaccine* 21:4459-4471; Zhang et al., (2004) *Infect. Immun.* 72:637-644; Zhang et al., (2005) *Infect. Immun.* 73:3990-3998). Briefly, the HagB gene was cloned from *P. gingivalis* 381 into a pET vector with a lac promoter and histidine tag and expressed in *Escherichia coli* JM109. Protein expression was induced following isopropyl-β-D-thiogalactopyranoside (IPTG) induction. rHagB was purified from the soluble fraction of the bacterial lysates by using a His-bind resin column, according to the manufacturer's instruction (Novagen, Madison, WI). The purity of rHagB was confirmed by silver staining and Western blot analysis using a rabbit anti-rHagB antibody. The concentration of rHagB was estimated by the bicinchoninic acid protein determination assay (Pierce, Rockford, IL), using bovine serum albumin (BSA) as the standard.

Example 12

Mice and Immunization:

BALB/c mice used in this study were from Frederick Cancer Research (Fredrick, MD). To assess the adjuvant activity of the MS saponin-based immune adjuvants, groups of female mice (8-10 weeks of age; 6 mice per group) were immunized by the subcutaneous (s.c.) route with OVA (20 μg) or rHagB (35 μg) alone, or with antigen plus proper adjuvant such as GPI-0100 (100 μg) or a MS adjuvant (100 μg) on days 0, 14 and 28. Prior to each immunization and at two weeks post last immunization, mice were weighed and blood samples were collected from the lateral tail vein by using heparinized capillary pipettes. The serum was obtained after centrifugation and stored at −20° C. until assayed.

Example 13

Evaluation of Antibody Responses:

The levels of specific serum IgG and IgG subclasses against OVA or rHagB in each group were determined by an enzyme-linked immunosorbent assay (ELISA). Maxisorp-microtiter plates (NUNC International, Roskilde, DK) were coated with rHagB (1 μg/ml), OVA (0.1 μg/ml), or with optimal amounts of goat anti-mouse IgG, IgG1 or IgG2a in borate buffer saline (BBS; 100 mM NaCl, 50 mM boric acid, 1.2 mM $Na_2B_4O_7$, pH 8.2) at 4° C. overnight. Plates were blocked with 1% bovine serum albumin (BSA) and 0.02% sodium azide in BBS for 2 h at room temperature. Serial two-fold dilutions of serum samples were added in duplicate to the plates. To generate standard curves, serial dilutions of a mouse immunoglobulin reference serum (MP Biomedicals, Solon, OH) were added to two rows of wells in each plate that had been coated with the appropriate anti-mouse IgG or IgG subclass reagent. After incubation (overnight at 4° C.) and washing of the plates, horseradish peroxidase-conjugated goat anti-mouse IgG or IgG subclass antibody was added to appropriate wells. After 4 h of incubation at room temperature, plates were washed and developed by o-phenylenediamine substrate with hydrogen peroxide. Color development was recorded at 490 nm. The concentrations of antibodies were determined by interpolation on standard curves generated by using the mouse immunoglobulin reference serum and constructed by a computer program based on four-parameter logistic algorithms (Softmax/Molecular Devices Corp., Menlo Park, CA).

Example 14

Statistical Analysis:

Statistical significance in antibody responses was evaluated by t tests (with unpaired, nonparametric and Mann-Whiteny test) using GraphPad Prism 8. Differences were considered significant at a P value<0.05.

Example 15

General Structure wherein:

$q_1$ is H or OH;

$q_2$ and $q_3$ are each independently selected from CHO, $CH_3$, $CH_2OH$, H, or a component of an acetal group;

$f_3$ and $f_4$ are each independently OH or an acetyl, or C3 and C4 of a fuocsyl unit wherein $f_3$, and $f_4$ form a cyclic ketal ring or cyclic carbonate ester;

$f_5$ and $ga_5$ are each independently selected from the group consisting of H, a methyl group, a carboxyl group, $R_4$—$NR_5$—C(O)—, and $R_4$—O—, wherein $R_4$ and $R_5$ are each independently a linear chain having the structure $R_6(CH_2)_{0-20}$— or $R_6[(CH_2)_{0-20}O_{0-20}(CH_2)_{0-20}]_{0-20}$, wherein $R_6$ is H, OH, $COO(CH_2)_{0-6}H$, COOBn, C(O)NR_7Bn, $NR_7Bn$, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group of a carrier;

and wherein Rz is H or an alkyl group;

r3 is H, a monosaccharide, disaccharide, or a trisaccharide;

x3 is H, a monosaccharide (except xylose) or a disaccharide; and ga3 is H, a monosaccharide or a disaccharide.

Example 16

Synthetic Derivatives:

These semi-synthetic products were prepared from derivatizing the natural products (MS-A, MS-B, and MS-C, (FIGS. 12A-12C, respectively) at the carboxyl group of the glucuronic acid unit.

R₁ =
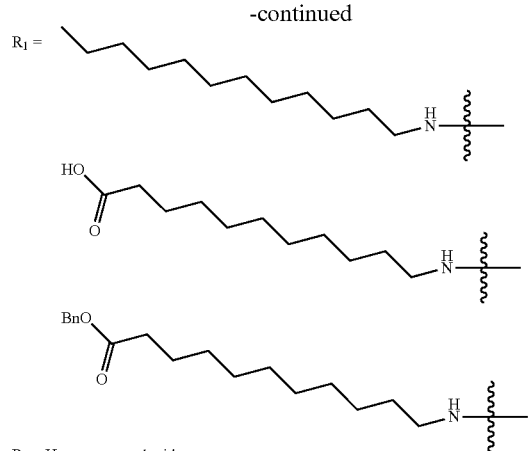
5
10
15
R₂ = H or monosaccharide
R₃ = H or OH
Example 17
Saponin-MPL Conjugate

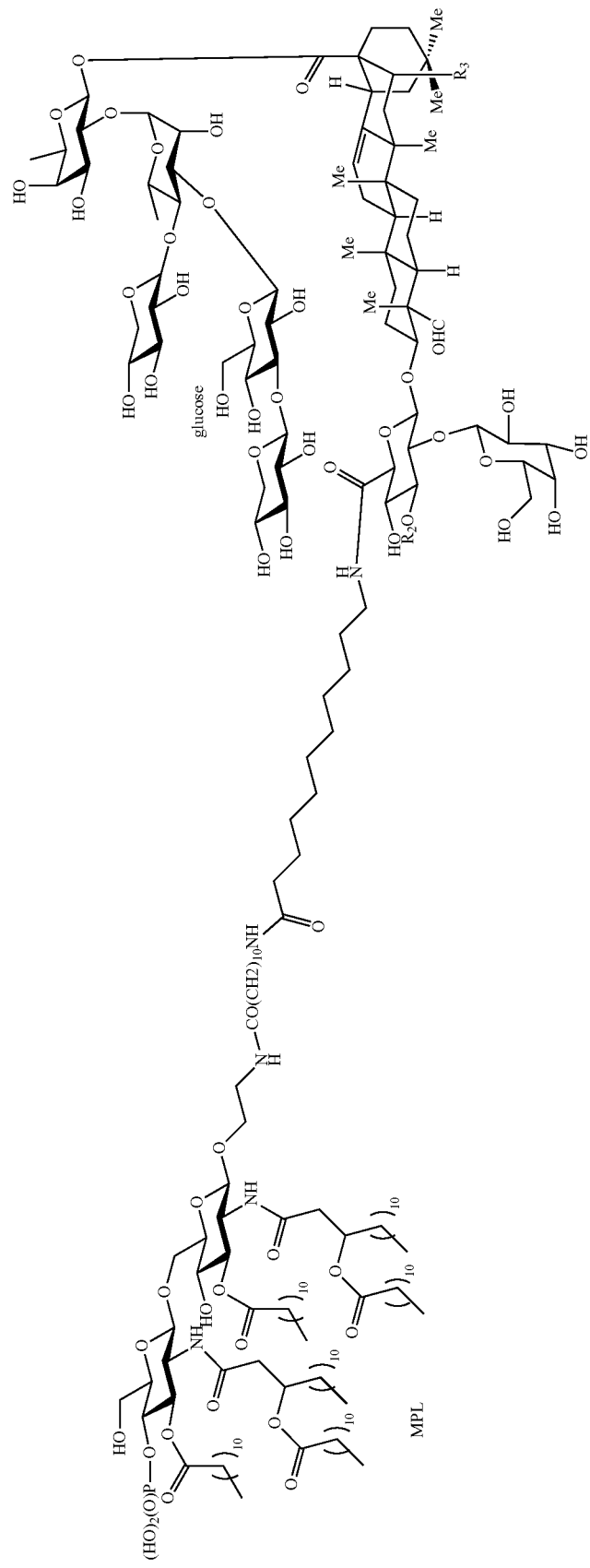

Example 18
Saponin-Pam2Cys Conjugate
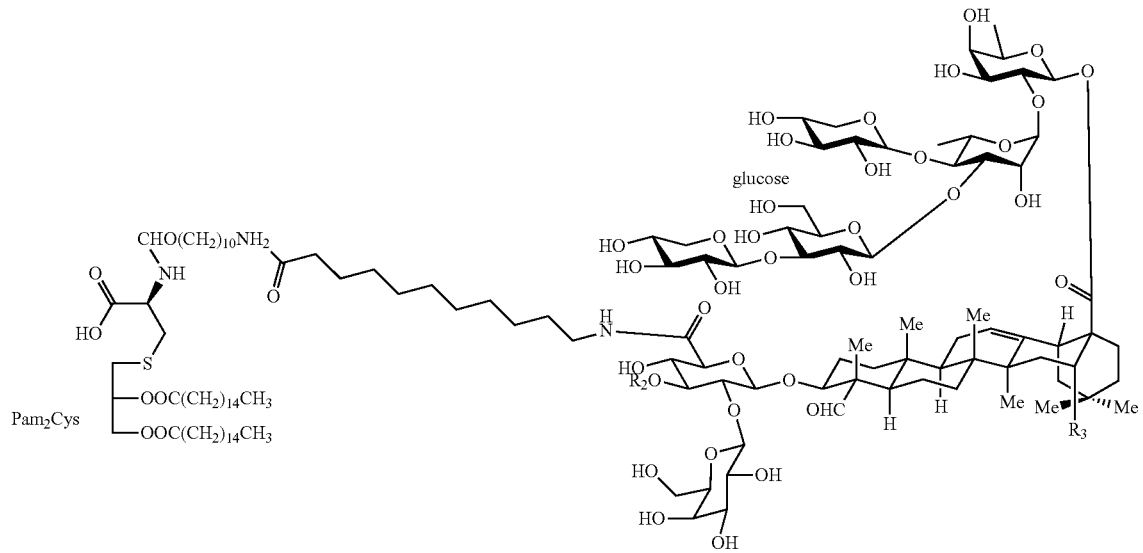
Example 19
Synthetic Derivatives:
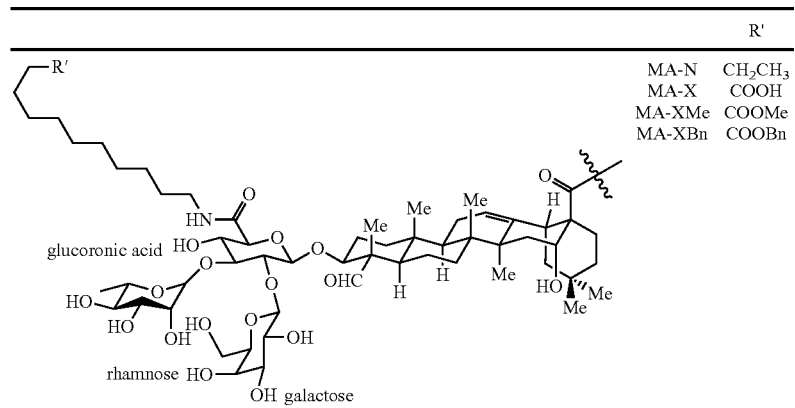
| | R' |
|---|---|
| MA-N | $CH_2CH_3$ |
| MA-X | COOH |
| MA-XMe | COOMe |
| MA-XBn | COOBn |
R' = —$CH_2CH_3$, COOH, COOMe, COOBn
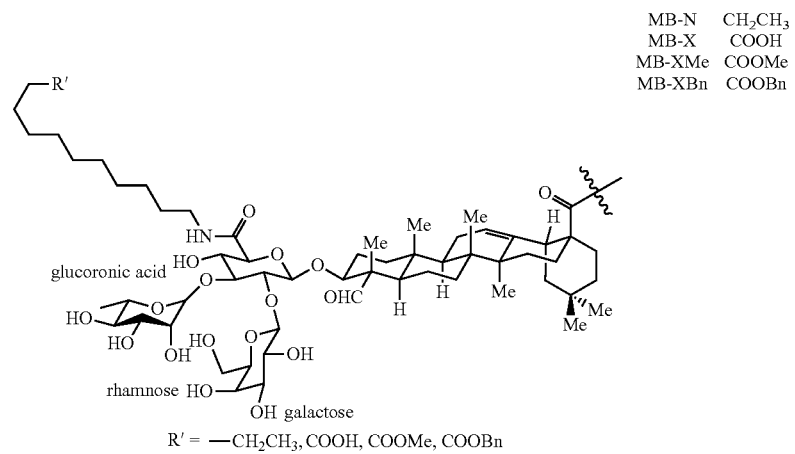
| | R' |
|---|---|
| MB-N | $CH_2CH_3$ |
| MB-X | COOH |
| MB-XMe | COOMe |
| MB-XBn | COOBn |
R' = —$CH_2CH_3$, COOH, COOMe, COOBn

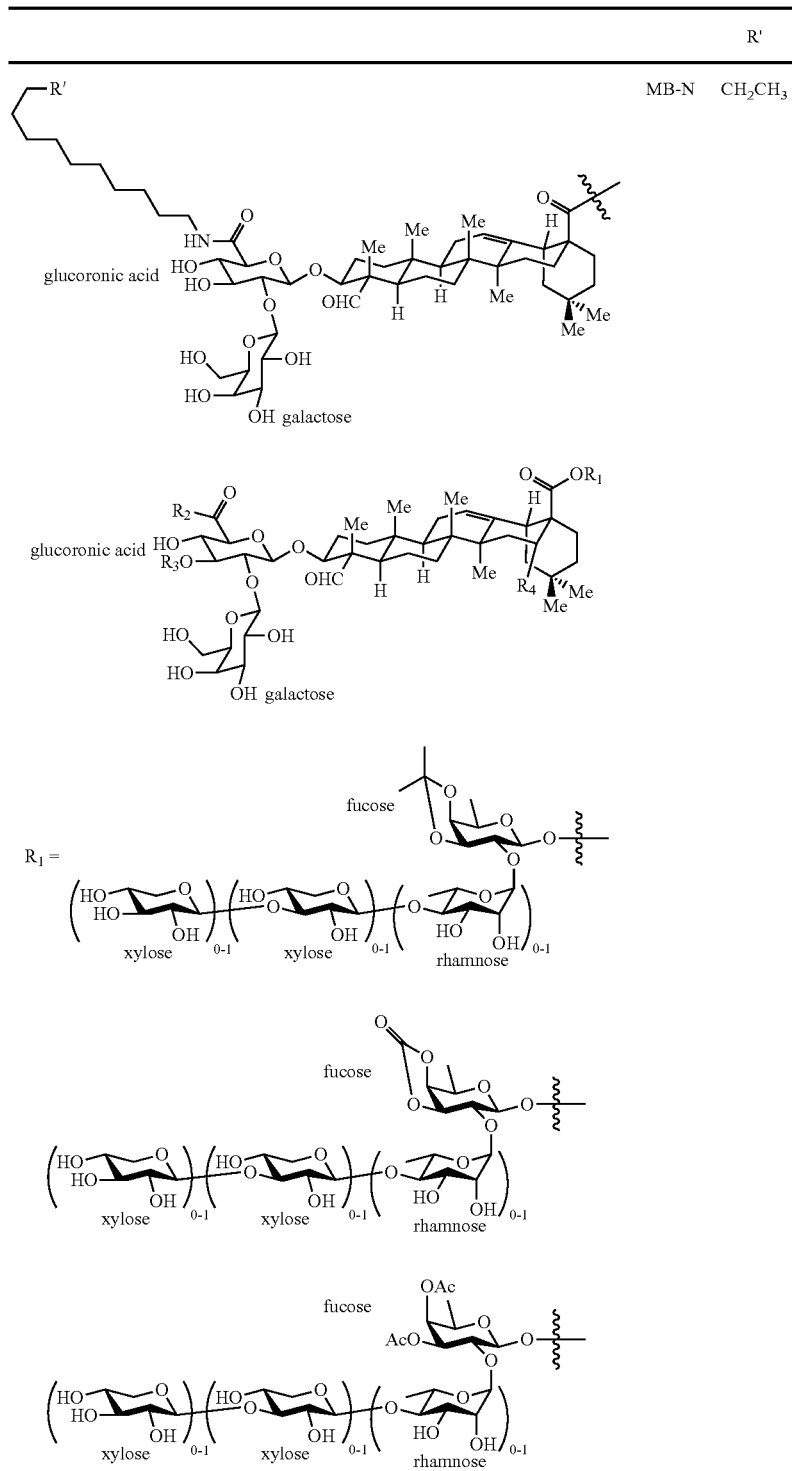
$R_2$ = OH, or $NR_6(CH_2)_nR_5$, n = 1-12
$R_3$ = H, rhamose
$R_4$ = H, OH
$R_5$ = $CH_2CH_3$, $COOR_7$
$R_6$ = H, $CH_3$, $CH_2CH_3$, $CH(CH_3)_2$, or $(CH_2)_nR_5$, n = 1-12
$R_7$ = $CH(CH_3)_2$, $C(CH_3)_3$, $CH_2Ph$, or $(CH_2)_nH$, n = 0-12

-continued
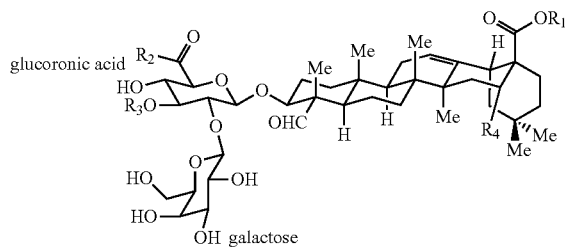
R1 =
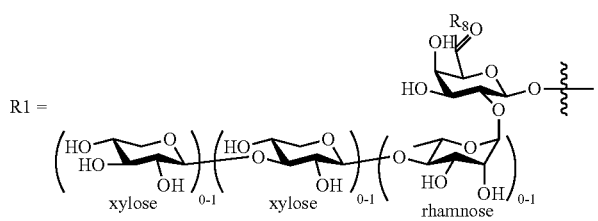
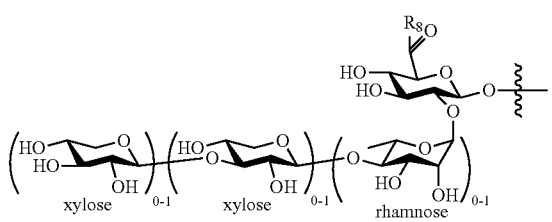
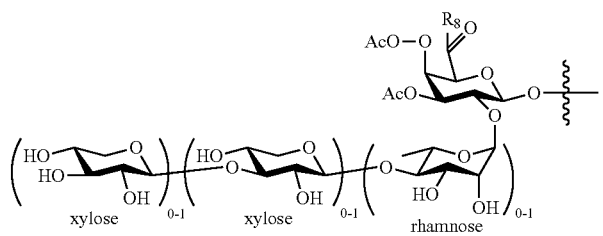
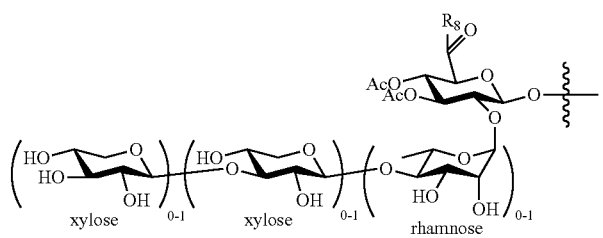

-continued

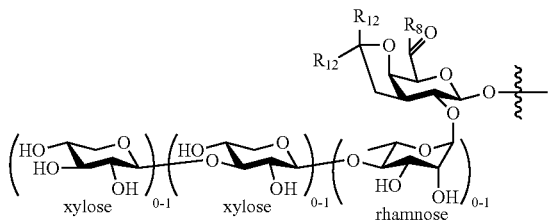

$R_2$ = OH, or $NR_6(CH_2)_nR_5$, n = 1-12
$R_3$ = H, rhamose
$R_4$ = H, OH
$R_5$ = $CH_2CH_3$, $COOR_7$
$R_6$ = H, $CH_3$, $CH_2CH_3$, $CH(CH_3)_2$, or $(CH_2)_nR_5$, n = 1-12
$R_7$ = $CH(CH_3)_2$, $C(CH_3)_3$, $CH_2Ph$, or $(CH_2)_nH$, n = 0-12
$R_8$ = OH, or $NR_{10}(CH_2)_nR_9$, n = 1-12
$R_9$ = $CH_2CH_3$, $COOR_{11}$
$R_{10}$ = H, $CH_3$, $CH_2CH_3$, $CH(CH_3)_2$, or $(CH_2)_nR_9$, n = 1-12
$R_{11}$ = $CH(CH_3)_2$, $C(CH_3)_3$, $CH_2Ph$, or $(CH_2)_nH$, n = 0-12
$R_{12}$ = $CH_3$, or O Example 20

Figure 13:
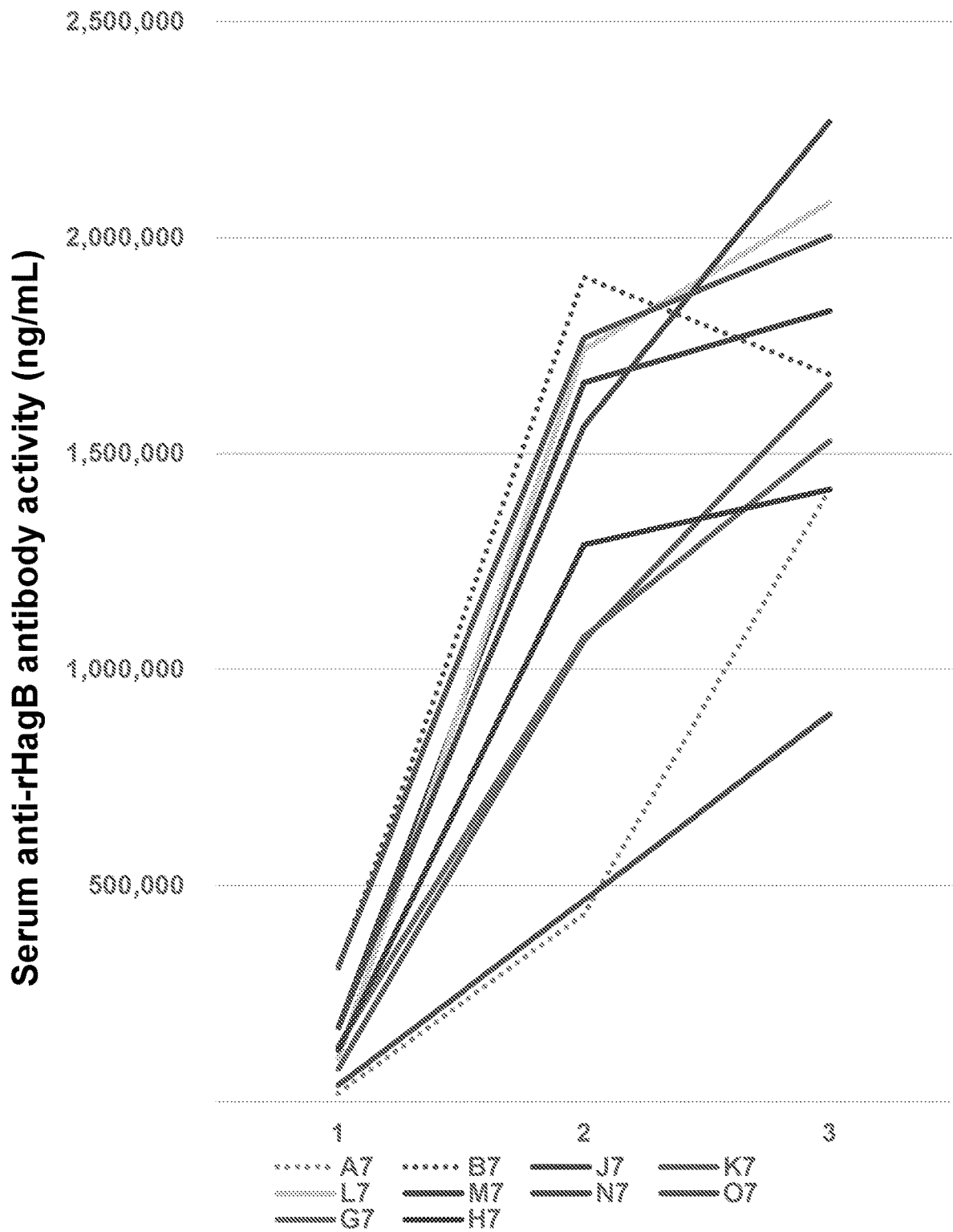
FIG. 13 illustrates anti-rHagB IgG antibody formation induced by rHagB in mice with saponin adjuvants of the disclosure.
Figure 14:
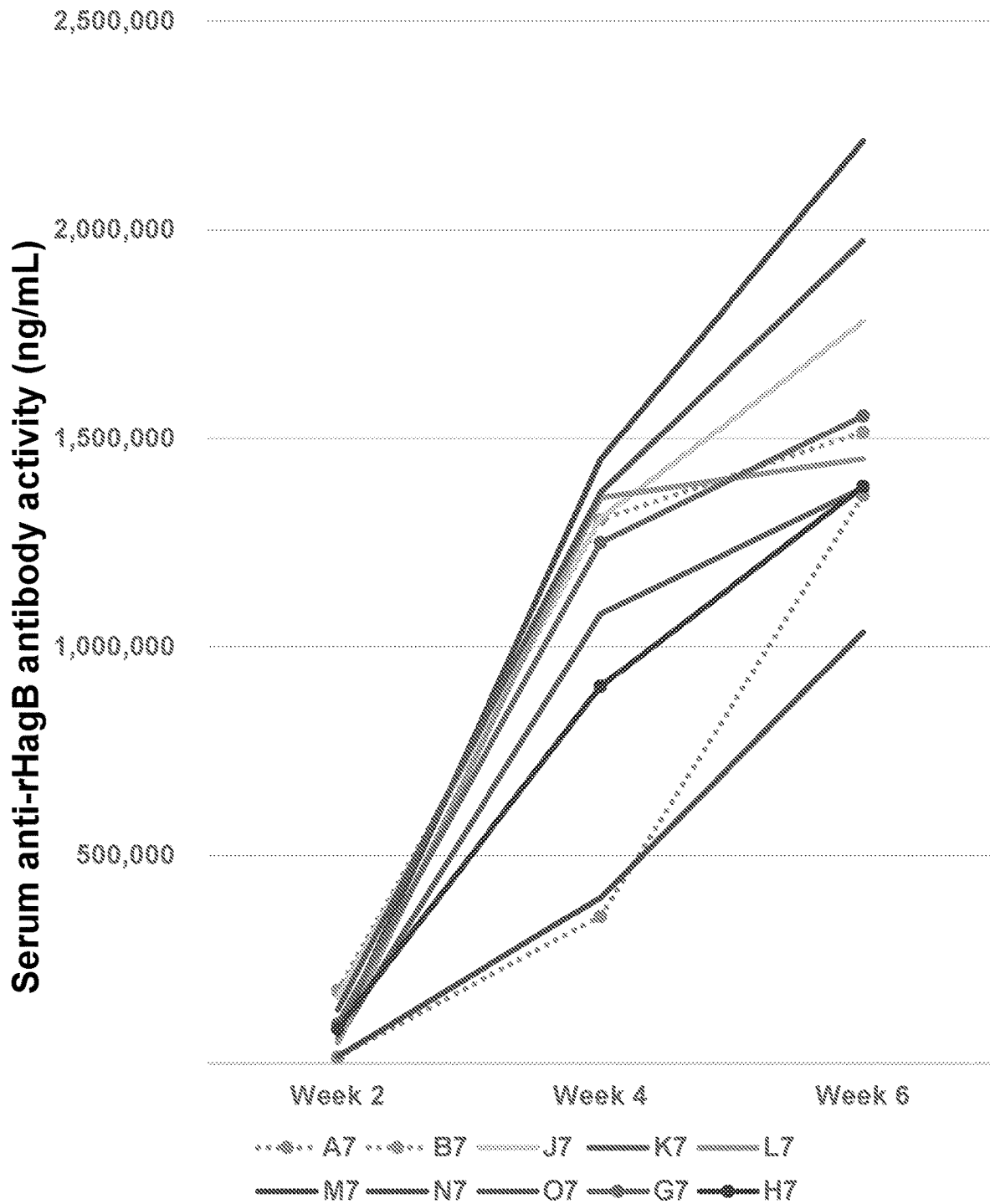
FIG. 14 illustrates anti-rHagB Ig1 antibody formation induced by rHagB in mice with saponin adjuvants of the disclosure.
Figure 15:
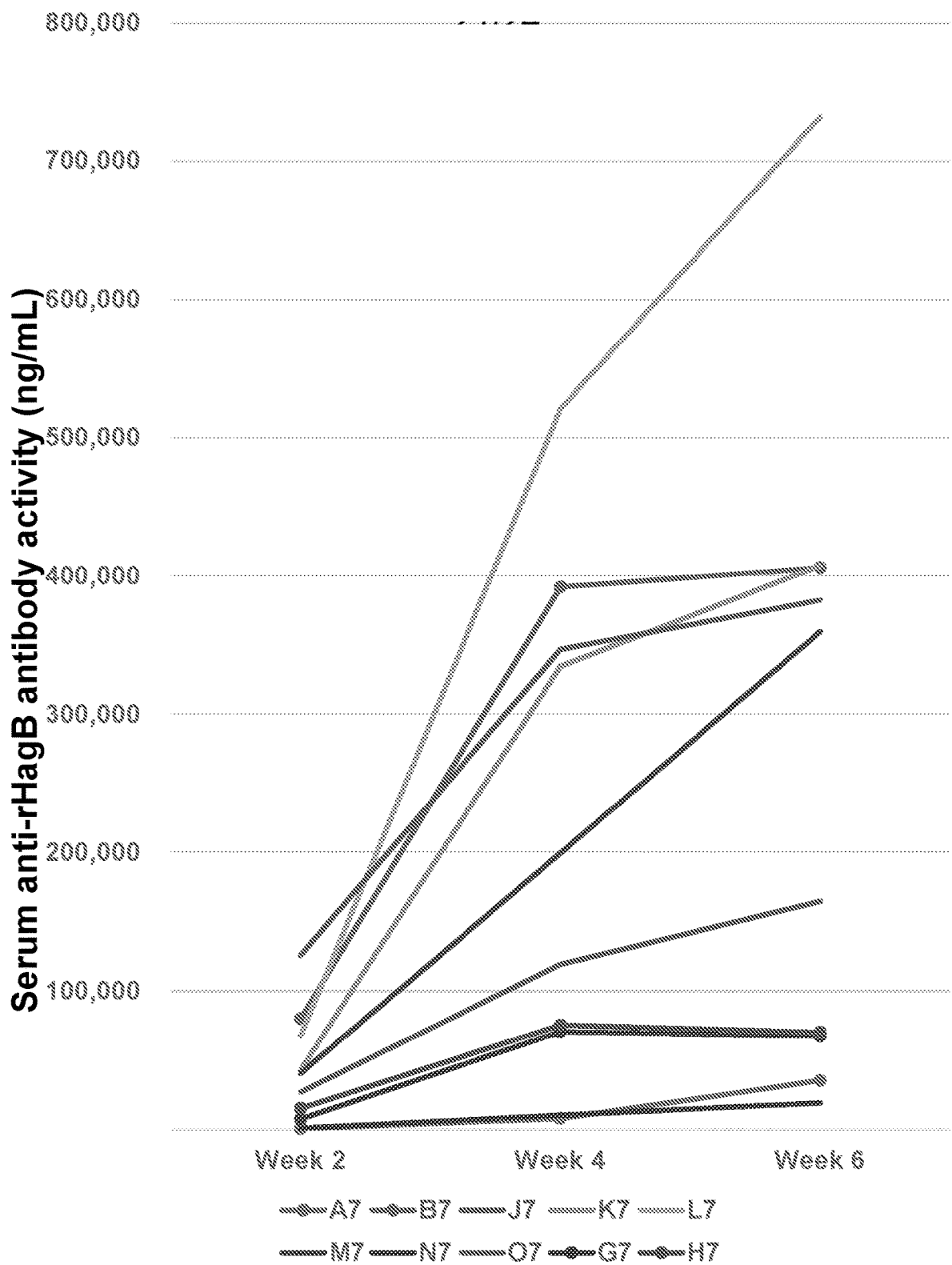
FIG. 15 illustrates anti-rHagB Ig2a antibody formation induced by rHagB in mice with saponin adjuvants of the disclosure.

Anti-rHagB Antibody Formation Induced by rHagB in Mice with a Variety of the Saponin Adjuvants of the Disclosure:

The generation of IgG, Ig1, and Ig2a in BALB/c mice (6 mice/group), female, immunized with 200 μl/mouse: 100 μl/site, 2 sites/mouse at dorsal s.c. is shown in FIGS. 13-15, respectively.

Immunized with: A, 20 μg rHagB; B, 20 μg rHagB+100 μg GPI-0100; G, 20 μg rHagB+100 μg MA; H, 20 μg rHagB+100 μg MB; J, 20 μg rHagB+100 μg MA-N; K, 20 μg rHagB+100 μg MA-X; L, 20 μg rHagB+100 μg MA-XBn; M, 20 μg rHagB+100 μg MB-N; N, 20 μg rHagB+100 μg MB-X; O, 20 μg rHagB+100 μg MC-N.

What is claimed:
1. A modified saponin derived from *Momordica cochinchinensis* Spreng and having the formula:

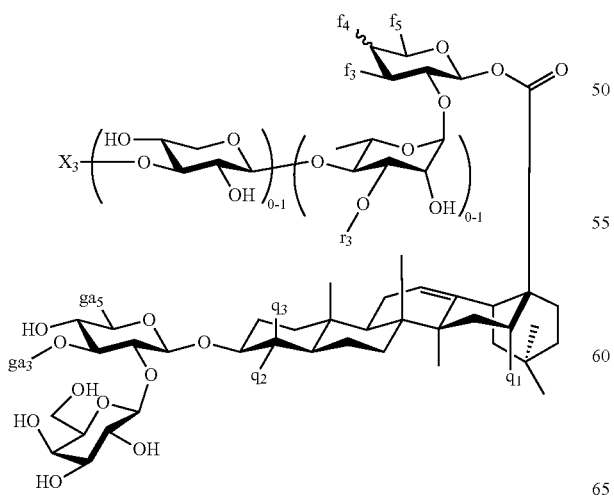

wherein:
$q_1$ is H or OH;
$q_2$ and $q_3$ are each independently selected from CHO, $CH_3$, $CH_2OH$, H, and an acetal group;
$f_3$ and $f_4$ are each independently OH or an acetyl, or C3 and C4 of a fuocsyl unit wherein $f_3$ and $f_4$ form a cyclic ketal ring or cyclic carbonate ester;
$f_5$ is selected from the group consisting of H, a methyl group, $R_4$—$NR_5$—C(O)—, $R_4$—O—, $R_4$—O—$CH_2$—, and $R_4$—O—C(O)—, wherein $R_4$ and $R_5$ are each independently a linear chain having the structure $R_6(CH_2)_{1-20}$— or $R_6[(CH_2)_{1-20}O_{0-1}(CH_2)_{0-20}]_{1-20}$, wherein $R_6$ is H, OH, $COO(CH_2)_{0-6}$H, COOBn, $C(O)NR_7$Bn, $NR_7$Bn, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group comprising a carrier selected from the group consisting of a polyamine polymer, a polyethylene glycol amine, poly (ethyleneimine), a nanocarbon, and an amino-containing biological molecule; and wherein $R_7$ is H or an alkyl group;
$ga_5$ is selected from the group consisting of H, a methyl group, a carboxyl $R_4$—O—C(O)—, $R_4$—$NR_5$—C(O)—, $R_4$—O—, and $R_4$—O—$CH_2$—, wherein the carboxyl $R_4$—O—C(O)— is not H—O—C(O)—;
wherein $R_4$ and $R_5$ are each independently H, a linear chain having the structure $R_6(CH_2)_{1-20}$— or $R_6[(CH_2)_{1-20}O_{0-1}(CH_2)_{0-20}]_{1-20}$, wherein $R_6$ is H, OH, $COO(CH_2)_{0-6}$H, COOBn, $C(O)NR_7$Bn, $NR_7$Bn, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group comprising a carrier selected from the group consisting of a polyamine polymer, a polyethylene glycol amine, poly (ethyleneimine), a nanocarbon, and an amino-containing biological molecule; and wherein $R_7$ is H or an alkyl group;

$r_3$ is H, a monosaccharide, disaccharide, or a trisaccharide;

$X_3$ is H; and $ga_3$ is H, a monosaccharide or a disaccharide;

wherein the *Momordica* saponin I has a structure represented by the following formula:

[Structure of Momordica saponin I]

and wherein the *Momordica* saponin II has a structure represented by the following formula:

[Structure of Momordica saponin II]

2. The modified saponin of claim 1, wherein the modified saponin has the formula I:

[Structure of formula I]

wherein:

$q_1$ is H or OH;

$q_2$ and $q_3$ are each independently selected from CHO, $CH_3$, $CH_2OH$, H, and an acetal group; and $ga_5$ is $R_3$, wherein $R_3$ is selected from the group consisting of H, a methyl group, a carboxyl group ($R_4$—O—C(O)—, $R_4$—$NR_5$—C(O)—, $R_4$—O—, and $R_4$—O—$CH_2$—, wherein the carboxyl $R_4$—O—C(O)— is not H—O—C(O)—;

wherein $R_4$ and $R_5$ are each independently H, a linear chain having the structure $R_6(CH_2)_{1-20}$— or $R_6[(CH_2)_{1-20}O_{0-1}(CH_2)_{0-20}]_{1-20}$, wherein $R_6$ is H, OH, $COO(CH_2)_{0-6}H$, COOBn, C(O)$NR_7Bn$, $NR_7Bn$, OBn, a saccharide unit, a *Momordica* saponin I or II, a muramyldipeptide, a monophosphoryl lipid A (MPL) unit, an α-Galcer unit, a dipalmitoyl-S-glyceryl cysteine (PamCys) unit, or a functional group comprising a carrier selected from the group consisting of a polyamine polymer, a polyethylene glycol amine, poly (ethyleneimine), a nanocarbon, and an amino-containing biological molecule, and wherein $R_7$ is H or an alkyl group.

3. The modified saponin of claim 2, wherein $R_3$ is H.

4. The modified saponin of claim 2, wherein $R_3$ is $R_4$—NH—C(O)—, wherein $R_4$ is a long-chain fatty acid having the structure HOOC—$(CH_2)_{6-20}$—.

5. The modified saponin of claim 2, wherein $R_3$ is an alkoxy group having the structure $H_3C$—$(CH_2)_{6-20}$—O—$CH_2$.

6. The modified saponin of claim 2, wherein $R_3$ is $R_4$—NH—C(O)—, wherein $R_4$ is a long-chain alcohol having the structure HO—$(CH_2)_{6-20}$—.

7. The modified saponin of claim 2, wherein $ga_5$ is $R_4$—NH—C(O)—, wherein $R_4$ is an alkyl terminated with a functional group selected from an ester group, an ether group, an amino group, a cyano group, a carbonyl group, an azido group, and an aromatic group.

8. The modified saponin of claim 2, wherein $R_3$ is $R_4$—NH—C(O)—, wherein $R_4$ is an alkyl $R_6O(CH_2)_{6-20}$—, and wherein $R_6$ is selected from a saccharide unit selected from the group consisting of a monosaccharide, a disaccharide, and trisaccharide.

9. The modified saponin of claim 2, wherein $R_3$ is $R_4$—NH—C(O)—, wherein $R_4$ is an alkyl terminated with a monophosphoryl lipid A (MPL).

10. The modified saponin of claim 2, wherein $R_3$ is $R_4$—NH—C(O)—, and wherein $R_4$ is an alkyl terminated with a dipalmitoyl-S-glyceryl cysteine (Pam2Cys) or a tripalmitoyl-S-glyceryl cysteine (Pam3Cys).

11. The modified saponin of claim 2, wherein $R_3$ is $R_4$—NH—C(O)—, wherein $R_4$ is an alkyl terminated with a muramyldipeptide unit.

12. The modified saponin of claim 2, wherein $R_3$ is $R_4$—NH—C(O)—, wherein $R_4$ is an alkyl terminated with an α-Galcer unit.

13. The modified saponin of claim 2, wherein $R_3$ is $R_4$—NH—C(O)—, wherein $R_4$ is an alkyl terminated with a *Momordica* saponin I unit.

14. The modified saponin of claim 2, wherein $R_3$ is $R_4$—NH—C(O)—, wherein $R_4$ is an alkyl terminated with a *Momordica* saponin II unit.

15. The modified saponin of claim 2, wherein the modified saponin is selected from the group consisting of formulas A-E:

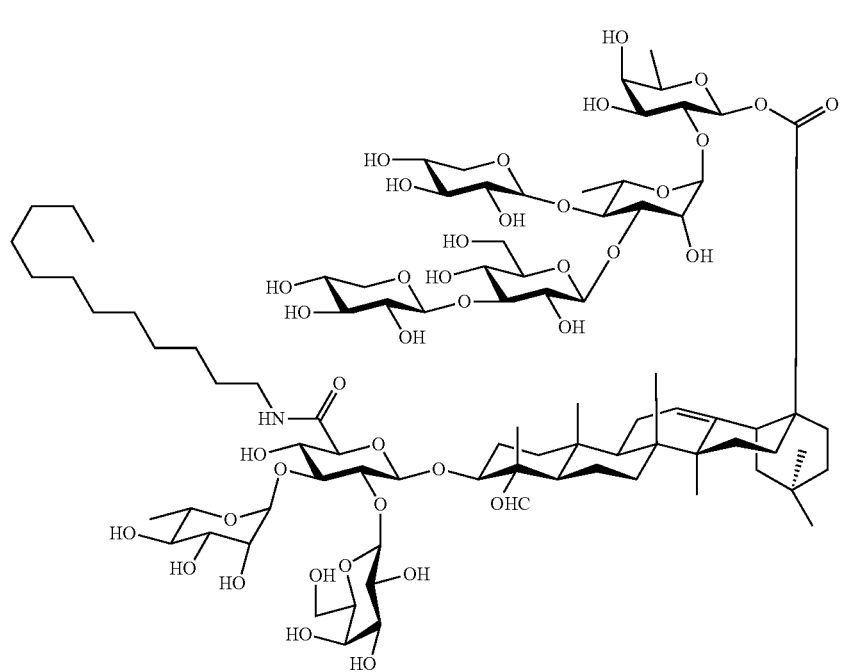
A
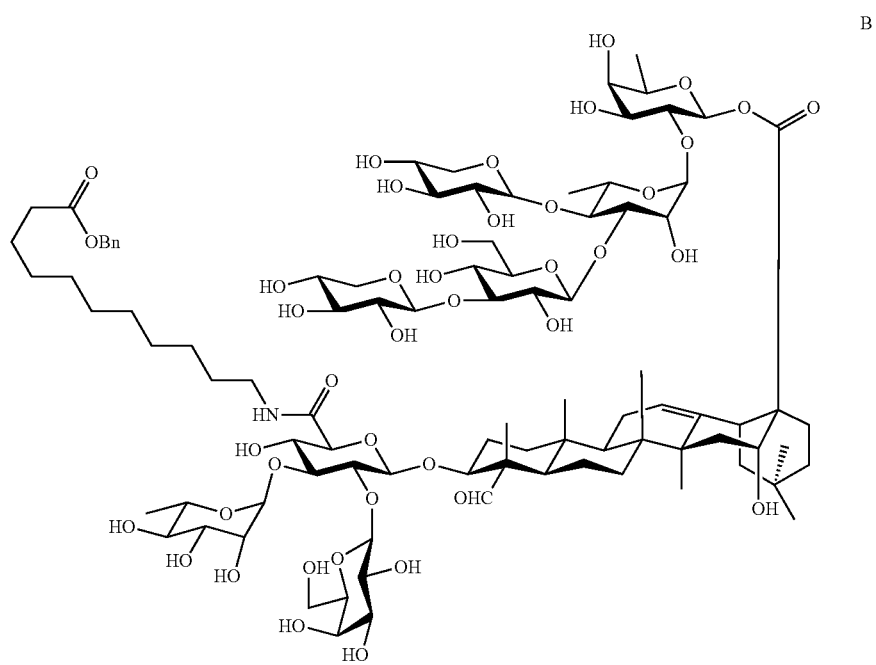
B

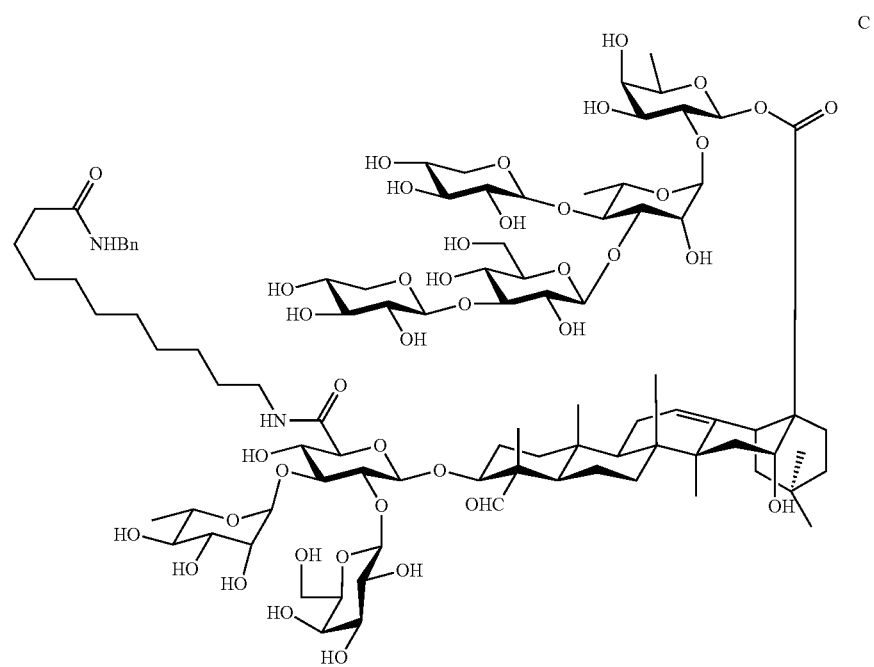
C
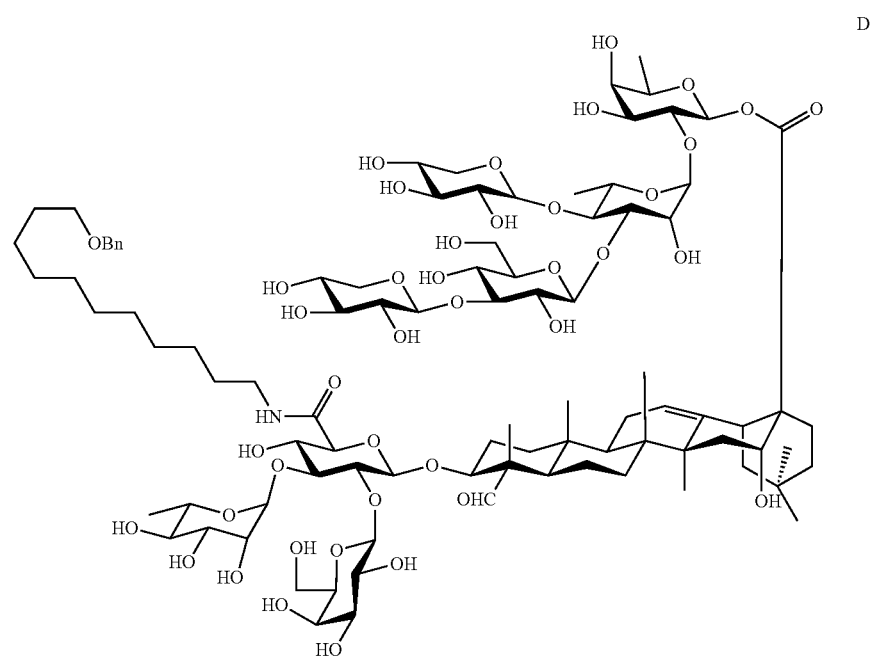
D

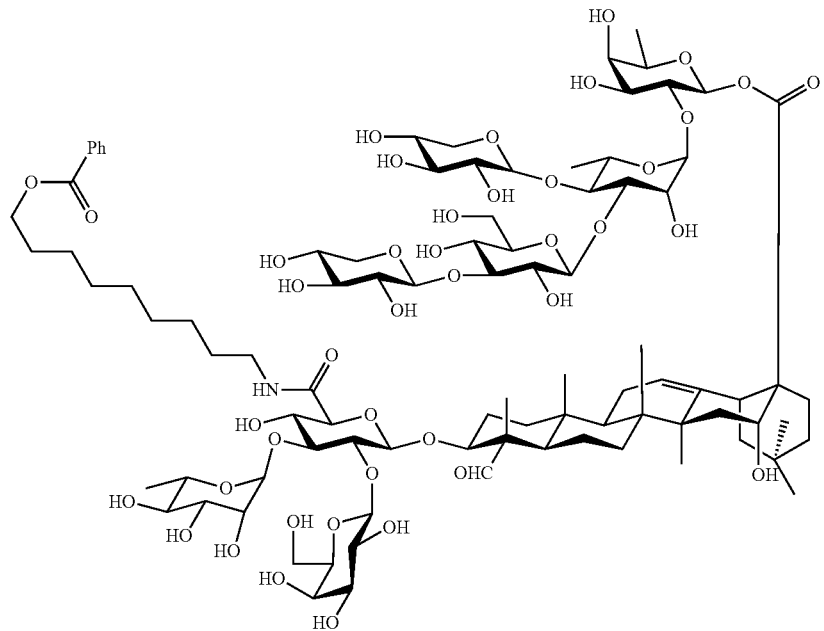

E

16. The modified saponin of claim 1, wherein ga$_5$ is an alkoxy group having the structure H$_3$C—(CH$_2$)$_{6\text{-}20}$—O—CH$_2$.

17. The modified saponin of claim 1, wherein ga$_5$ is R$_4$—NH—C(O)—, wherein R$_4$ is a long-chain alcohol having the structure HO—(CH$_2$)$_{6\text{-}20}$—.

18. The modified saponin of claim 1, wherein ga$_5$ is R$_4$—NH—C(O)— wherein R$_4$ is an terminated with a functional group selected from an ester group, an ether group, an amino group, a cyano group, a carbonyl group, an azido group, and an aromatic group.

19. The modified saponin of claim 1, wherein ga$_5$ is R$_4$—NH—C(O)—, wherein R$_4$ is an alkyl R$_6$O(CH$_2$)$_{6\text{-}20}$—, and wherein R$_6$ is selected from a saccharide unit selected from the group consisting of a monosaccharide, a disaccharide, and trisaccharide.

20. The modified saponin of claim 1, wherein ga$_5$ is R$_4$—NH—C(O)—, wherein R$_4$ is an alkyl terminated with a monophosphoryl lipid A (MPL).

21. The modified saponin of claim 1, wherein ga$_5$ is R$_4$—NH—C(O)—, and wherein R$_4$ is an alkyl terminated with a dipalmitoyl-S-glyceryl cysteine (Pam$_2$Cys) or a tripalmitoyl-S-glyceryl cysteine (Pam$_3$Cys).

22. The modified saponin of claim 1, wherein ga$_5$ is R$_4$—NH—C(O)—, wherein R$_4$ is an alkyl terminated with a muramyldipeptide unit.

23. The modified saponin of claim 1, wherein ga$_5$ is R$_4$—NH—C(O)—, wherein R$_4$ is an alkyl terminated with an α-Galcer unit.

24. The modified saponin of claim 1, wherein ga$_5$ is R$_4$—NH—C(O)—, wherein R$_4$ is an alkyl terminated with a *Momordica* saponin MS I unit.

25. The modified saponin of claim 1, wherein ga$_5$ is R$_4$—NH—C(O)—, wherein R$_4$ is an alkyl terminated with a *Momordica* saponin II unit.

26. The modified saponin of claim 1, wherein q$_2$ and q$_3$ are each independently selected from CHO, CH$_3$, CH$_2$OH, and H.

* * * * *